US009688973B2

(12) United States Patent
Otani et al.

(10) Patent No.: US 9,688,973 B2
(45) Date of Patent: *Jun. 27, 2017

(54) POLYPEPTIDES HAVING ALPHA-GLUCOSIDASE ACTIVITY AND POLYNUCLEOTIDES ENCODING SAME

(71) Applicant: NOVOZYMES, INC., Davis, CA (US)

(72) Inventors: Suzanne Otani, Elk Grove, CA (US); Haiyan Ge, Davis, CA (US); Paul Harris, Carnation, WA (US); Debbie Yaver, Davis, CA (US); Alexander Blinkovsky, Davis, CA (US)

(73) Assignee: NOVOZYMES, INC., Davis ( * ) Notice: Subject to any disclaimer, the term of this patent is extended or adjusted under 35 U.S.C. 154(b) by 0 days.

This patent is subject to a terminal disclaimer.

(21) Appl. No.: 14/104,756

(22) Filed: Dec. 12, 2013

(65) Prior Publication Data

US 2014/0227391 A1  Aug. 14, 2014

Related U.S. Application Data

(62) Division of application No. 11/171,701, filed on Jun. 29, 2005, now Pat. No. 8,633,006.

(60) Provisional application No. 60/585,336, filed on Jun. 29, 2004.

(51) Int. Cl.
| | |
|---|---|
| *C12P 21/06* | (2006.01) |
| *C12N 9/24* | (2006.01) |
| *C12N 1/20* | (2006.01) |
| *C12N 1/00* | (2006.01) |
| *C07H 21/02* | (2006.01) |
| *C12N 9/26* | (2006.01) |
| *C12C 5/00* | (2006.01) |
| *C12C 7/20* | (2006.01) |
| *C12C 11/00* | (2006.01) |
| *C12C 12/02* | (2006.01) |
| *C12N 15/82* | (2006.01) |
| *C12C 7/04* | (2006.01) |

(52) U.S. Cl.
CPC ............ *C12N 9/2408* (2013.01); *C12C 5/004* (2013.01); *C12C 7/04* (2013.01); *C12C 7/20* (2013.01); *C12C 11/00* (2013.01); *C12C 12/02* (2013.01); *C12N 9/2411* (2013.01); *C12N 15/8245* (2013.01)

(58) Field of Classification Search
USPC .............. 435/69.1, 200, 252.3, 254.3, 320.1; 536/23.1, 23.74
See application file for complete search history.

(56) References Cited

U.S. PATENT DOCUMENTS 6,461,837 B1 * 10/2002 Yaver ...................... C12N 9/20
435/198
2003/0082595 A1  5/2003 Jiang
2003/0119013 A1  6/2003 Jiang
2004/0101591 A1  5/2004 Sato

FOREIGN PATENT DOCUMENTS

WO    2004/031072 A2    4/2004

OTHER PUBLICATIONS

Kato et al Novel α-Glucosidase from Aspergillus nidulans with Strong Transglycosylation ActivityAppl Environ Microbiol. Mar. 2002; 68(3): 1250-1256.*
Score Search results for SEQ ID Nos. 1, 3 and 5 Aug. 21, 2015.*
Minetoki et al, 1995, Biosci Biotechnol Biochem 59 (8), 1516-1521.
Boase et al, 2000, UNIPROT—Access No. Q9UV08.
Ozeki et al, 1997, GENESEQ—Access No. AAW15191.
Uozumi et al, 1994, UNIPROT—Access No. AAR42212.
Minetoki et al, 1995, UNIPROT—Access No. Q12558.
Kelly et al, Microbial a-Glucosidases, Process Biochemistry, May-Jun. 1983, p. 6-12.
Nakamura et al., Cloning and sequencing of an a-glucosidase gene from Aspergillus niger and its expression in A. nidulans, 1997, J. of Biotechnology. 53: 75-84.
Rudick and Elbein, 1974, Archives of Biochemistry and Biophysics 1611: 281-290.
Olutiola, 1981, Mycologia 73: 1130.
Kato et al., 2002, Appl. Environ. Microbiol. 68: 1250-1256.
Rudick et al., 1979, Archives of Biochemistry and Biophysics 193: 509.
Leibowitz and Mechlinski, 1926, Hoppe-Seyler's Zeitschrift für Physiologische Chemie 154: 64.
Tanaka et al., 2002, Biosci. Biotechnol. Biochem. 66: 2415-2423.
Yamasaki et al., 1977, Agricultural and Biological Chemistry 41(9), 1553-1558.
Flores-Carreon and Ruiz-Herrera, 1972, Biochemica et Biophysica Acta 258: 496.
Yamasaki et al., 1976, Agricultural and Biological Chemistry 40(4), 669-676.
Yamasaki et al., 1977, Agricultural and Biological Chemistry 41(8), 1451-1458.
Bowie et al, 1990, Science 16, 1306-1310.
Faridmoayer et al, 2005, Glycobiology 15(12), 1341-1348.
Kennell, 1971, Prog Nucleic Acid Res Mol Biol 11, 259-301.
Ngo et al, 1994, The Protein Folding Problem & Tertiary Structure Prediction 492-506.
Protein SQ Searches, Feb. 2005, 1-3.
Sarfaty et al, 2007, Science 315, 525-528.
Voet et al, 1990, Biochemistry 126-128.
Yan et al, 2000, Science 290, 523-527.
Kato et al., Sequence Alignment Accession No. Q9C157 (TreEmberil) Jun. 1, 2001.
Berka et al. database GenBank No. AAF07600, Sequence Alignment Mar. 22, 2000.
Keshiri et al. 2000, Journal of Applied Microbiology 89, 825-833.
Schmoll et al. 2004, Fungal Genetics and Biology 41, 877-887.
Guo et al. 2004, PNAS 101(25), 9205-9210.
Witkowski et al. 1999, Biochemistry 38, 11643-11650.
Seffernick et al. 2001, Journal of Bacteriology 183(8), 2405-2410.

* cited by examiner

Primary Examiner — Maria Leavitt
(74) Attorney, Agent, or Firm — David Fazzolare

(57) ABSTRACT

The present invention relates to isolated polypeptides having alpha-glucosidase activity and isolated polynucleotides encoding the polypeptides. The invention also relates to nucleic acid constructs, vectors, and host cells comprising the polynucleotides as well as methods for producing and using the polypeptides.

4 Claims, 25 Drawing Sheets

```
     M  L  R  S  L  L  L  L  A  P  L  V  G  A  A  V  I  G  A  R
  1  ATGTTGAGATGCTGCTGCTGCTACTTCTGGCGCCCCTTGTGGGGGCTGCCGTGATCGGCGCCAGG
     D  H  S  Q  E  C  P  G  Y  K  A  T  N  I  R  E  G  R  D  S
 61  GACCACAGCCAGGAGTGTCCTGGTTACAAGGCCACCAATATTAGAGAGGGTCGCGATTCC
     L  T  A  D  L  T  L  A  G  K  P  C  N  T  Y  G  T  D  L  K
121  TTAACGGCGGATTTGACCTTGGCCGGTAAACCCTGCAACACTTACGGCACCGACTTGAAG
     N  L  K  L  V  E  Y  Q  T
181  AATCTGAAACTCGTTGAGTACCAGACCCGTTAAACGGCTATGAT
                                D  K  R  L  H  V  K  I  Y  D  A  E  E
241  TGTAGCTTACTTCTTTTCTAGATAAACGCCTCCATGTTAAGATCTATGACGCCGATGAGGA
     V  Y  Q  V  P  E  S  V  L  P  R  V  D  G  K  G  G  S  S  K
301  GGTTTACCAAGTCCCCGAGTCGGTTCTCCCGCGTGGATGGCAAAGGTGGCAGCAA
     K  S  A  L  K  F  D  Y  Q  A  N  P  F  S  F  K  V  K  R  G
361  GAAGTCGGCGCTCAAGTTCGACTATCAGGCGAATCCGTTCTCTTTCAAGGTCAAGAGAGG
     G  E  V  L  F  D  T  S  G  S  N  L  I  F  Q  S  Q  Y  L  S
421  CGGGGAGGTGCTCTTCGACACCTCGGGTTCGAATGATCTTCGAGTCGCAGTACCTGAG
     L  R  T  W  L  P  E  D  P  N  L  Y  G  L  G  E  H  T  D  S
481  CCTCCGCACCTGGTTGCCCGAGGATCCTAATCTCTACGGTCTTGGCGAGCACACGGATTC
     L  R  L  E  T  T  N  Y  T  R  T  L  W  N  R  D  A  Y  A  I
541  TCTTCGTCTGGAGACCACCAACTACACCCGTACTCTGTGGAACCGTGACGCGTATGCTAT
     P  E  K  T  N  L  V  G  T  H  P  V  Y  D  H  R  G  Q  H
601  TCCTGAGAAGACCAACCTGTACGGCACTCATCCCGTGTACTATGACCACCGTGGCCAACA
     G  T  H  G  V  F  L  N  S  N  G  M  D  I  K  I  D  K  T
661  CGGCACCCACGGTGTCTTCTTGCTGAACTCCAACGGCATGGACATTAAGATCGACAAGAC
```

Fig. 1A

```
         K  D  G  K  Q  Y  L  E  Y  N  T  L  G  G  V  F  D  P  Y  F
 721 CAAGGATGGCAAGCAGTACTTAGAGTACAACACTCTGGGAGGTGTCTTTGACTTTTACTT
         F  T  G  A  T  P  K  D  A  S  I  E  Y  A  K  V  G  L  P
 781 CTTTACCGGTGCCACCCCCAAGGATGCCAGCATCGAGTATGCGAAAGTCGGTCTTCC
       A  M  Q  S  Y  W  T  F  G
 841 CGCTATGCAGTCCTACTGGACGTTCGGTGTACGTTCCCTGATTCGATCTGCGGTCCTTC
                                    F  H  Q  C  R  Y  G  Y  R  D  V  P  E
 901 CGGCTAACTCTTGTCGTCTCTAGTTCCACCAATGCAGATACGGCTATCGTGATGTCTTTGAG
       V  A  E  V  V  Y  N  Y  S  Q  A  K  I  P  L  E  T  M  W  T
 961 GTCGCCGAGGTTGTCTACAACTACAGCCAGGCGAAGATTCCACTGGAGACCATGTGGACC
       D  I  D  Y  M  D  R  R  V  F  T  L  D  P  E  R  F  P  L
1021 GACATTGACTACATGGACAGACGTCGGGTGTTCACTCTTGACCCGGAGCCGATTCCCGCTC
       E  K  M  R  E  L  V  S  Y  L  H  N  H  N  Q  H  Y  I  V  M
1081 GAGAAGATGCGTGAGTTGGTGTCATATCTTCACAACCACAACTACATGCGTCATG
       V  D  P  A  V  S  V  S
1141 GTTGACCCGGCCGTCAGCGTCAGCGTGAGCGGTAAGTTTACCTTTCCAAGTATGGAGGGGTGGGT
                                    D  N  V  G  Y  N  D  G  M  E  Q  G  I  F
1201 GCATATTGACAAATGATCAGACAACGTTGGCTACAATGATGGAGCAGGGCATCTT
       L  Q  T  Q  N  G  S  L  Y  K
1261 CCTGCAGACTCAAAACGGTAGCCTCTACAAGGTCTACAAGGTAAGCCTTACCTAAAAGTACTAATGAC
                                    G  A  V  P  G  V  T  A  Y  P  D
1321 ACCCAGAATATTGACCCTATACAGGTGCCGTCTGGCGTGACTGCTTGCTGACT
       W  F  H  P  D  I  Q  K  Y  W  N  D  F  A  K  F  P  D  P
1381 GGTTCCACCCTGACATCCAAAAGTACTGGAACGACCAGTTTGCCAAATTCTTCGACCCCA
```

Fig. 1B

```
        K   T   G   V   D   I   D   G   L   W   I   D   M   N   E   A   A   N   F   C
1441  AGACCGGGCGTCGACATCGACGGTCTGTGGATCGATATGAACGAGGCCGCCAACTTCTGCC
        P   Y   P   C   S   D   P   E   G   Y   A   R   D   N   D   L   P   P   A   A
1501  CTTACCCTTGCAGTGATCCGGAGGGCTACGCTAGGGATAACGACCTGCCTCCCGCCGCTC
        P   P   V   R   P   S   N   P   R   P   L   P   G   F   P   G   D   F   Q   P
1561  CCCCCGTTCGGCCCCAGCAACCCGCGCCCGTTGCCCGGATTCCCTGGTGATTTCCAGCCCT
        S   S   S   K   R   S   T   K   G   S   K   V   G   L   P   N   R   D   L
1621  CATCCTCGTCGTCCAAGCGCTCCACCAAGGGATCTAAAGTGGACTGCCTAATCGTGACCTGA
        I   N   P   P   Y   M   I   R   N   E   A   G   S   L   S   N   K   T   I   N
1681  TCAACCCTCCGTACATGATCCGTAATGAAGCTGGCTCAGCTAAGCAACAAGACCATCAACA
        T   D   I   I   H   A   G   E   G   Y   A   E   Y   D   T   H   N   L   Y   G
1741  CCGATATCATTCATGCTGGTGAGGGATATGCCGAGTATGACACTCACAACCTTTATGGTA
                                                                                M   S   S
1801  CCAGTAAGTAGCCATCCCCTCTGAATGACGGGACAGTCTAACATTCAAAGTGATGAGTTC
        A   S   R   N   A   M   Q   H   R   R   P   G   V   R   P   L   V   I   T   R
1861  CGCTTCTGCGAATGCCATGCAACACCGCCGCCTGGGGTGCGCCCTGGTCATCACTCG
        S   T   Y   A   G   A   H   V   G   H   W
1921  CAGCACGTATGCTGGCGTCGGCCACGTTGGACACTGGTCGGTGTGCATCCATCTAGT
                                                                      L   G   D   N   I   S   E   W   S
1981  ACCTGCGAACTCTTATACTGACACTTGACAGGCTGGTGACAACATCTCCGAGTGGAGCA
        K   Y   R   I   S   I   S   Q   M   L   A   F   A   S   M   F   Q   V   P   M
2041  AGTACCGGCATTCCATCTCCGCAGATGCTTGCCTTTGCCTCGATGTTCCAGGTGCCTATGA
        I   G   S   D   V   C   G   F   G   N   T   T   E   L   C   A   R   W
2101  TCGGATCAGACGTCTGCGGGTTCGGCGGCAACACCGAGGAGCTCTGCGCTCGGCTGGG
```

Fig. 1C

```
         A  R  L  G  A  F  Y  T  F  F  R  N  H  N  E  I  T  G  I  P
2161 CGGGTCTCGGAGCCTTCTACACCTTCTTCCGCAACCACAATGAATCACCGGTATCCCGC
         Q  E  F  Y  R  W  P  T  V  A  E  S  A  R  K  A  I  D  I  R
2221 AGGAGTTCTACCGCTGGCCCACCGTTGCCGAGTCCGCTCGCAAGGCCATCGACATCCGCT
         Y  R  L  L  D  Y  I  Y  T  A  F  H  R  Q  T  Q  G  E  P
2281 ACAGGCTGCTTGACTACATCTACACAGCCTTCCACCGGCAGACCCAGGGCGAGCCCT
         F  L  Q  P  M  F  Y  L  Y  P  K  D  T  F  S  N  Q  L
2341 TCCTGCAGCCCATGTTCTACCTCTATCCCAAGGACACACTTCAGCAACCAGCTGC
         Q  F  F  Y  G  D  A  I  L  V  S  P  V  T  D  G  S  Q  T  S
2401 AGTTCTTCTACGGTGACGCCATCCTGGTCTCAGCCGTCACGGACGGGAGCCAGACTTCAG
         V  D  A  Y  F  P  D  D  I  F  Y  D  W  H  T  G  A  A  L  R
2461 TTGACGCATACTTCCCCGATGATATCTTCTACGATTGGCACACGGGCGCCGCCCTACGCG
         G  R  G  A  N  V  T  L  S  N  I  D  V  T  E  I  P  I  H  I
2521 GCCGGGGAGCCAACGTCACCCTCAGCAACATCGAGTGACTGAGATCCCCATCCACATCC
         R  G  S  I  I  P  V  R  S  E  S  A  M  T  T  T  E  L  R
2581 GCGGCCGCAGCATCATCCCCGTCCGAGTCCGAGTCCGCCATGACCACCACCGAGCTGCGCA
         K  K  G  F  E  L  I  I  A  P  G  L  D  G  T  A  S  G  S  L
2641 AGAAGGGCTTCGAGCTCATCATCGCCCCCAGGGCTTGATGGGACTGCCTCCGGGCAGTTTGT
         Y  L  D  D  G  D  S  I  E  P  R  A  T  L  E  F  T  Y
2701 ATCTCGACGACGGCGACTCCATCGAGCCGCGGGCCACCCTCGAGTTCACGTACC
         R  K  G  H  L  Q  V  K  G  K  F  G  F  R  T  E  V  K  I  N
2761 GCAAGGGCCATCTCCAGGTGAAGGGCAAGTTCGGTTTCCGCACGGAGGTCAAGATCAACG
         A  V  T  L  L  G  Q  S  A  P  A  S  K  S  A  D  V  A  S  L
2821 CCGTCACCCTGCTTGGCCAGTCTGCGCCTGCCTCCAAGTCTGCAGACGTGGCCCTCCCTTG
```

Fig. 1D

```
         D  S  G  R  Q  A  V  T  I  K  T  S  L  D  L  T  G  P  S  E
2881 ACTCTGGCCGCCAGGCAGTGACCATCAAGACGAGCCTGGATCTGACTGGTCCTTCCGAGA
         I  D  L  G  *
2941 TTGACCCTCGGCTAG
```

Fig. 1E

```
  1  ATGGCCCGGA GCAGCTCGTC TCTCTCCAGA TGGACGCTAT TGCTCGCGTT GGTTGTCATT CTCGGGTGTC
     M   A   R    S   S   S    L   S   R    W   T   L    L   L   A    L   V   V   I    L   G   C
                                                                                         L   V   P
 71  TTGTTGTACC CGGAGGTGAG CTCTATGCGC TCAACTTAAT CCAATAGTAA TGCTCGGCTT CCAAGTCTGC
     V   T   V    K   H   E    N   F   K    K   C   S   Q    S   G   F    C   K   R    N   R   A   P
                G
141  CAGTTACTGT GAAGCATGAG AACTTCAAGA AATGCTCTCA ATCGGGTTTT TGTAAGCGAA ACCGAGCTTT
     A   D   D    V   S   A    Q   G   A   S    W   I   S    P   Y   E    L   D   P   S    I   H
211  TGCAGATGAC GTTCCGCCCC AAGGCGCGTC TTGGATTTCA CCATATGAAC TCGATCCCTC CTCAATTCAC
     F   K   D    G   Q   L   Q    G   T   I    L   K   S    I   S   A   N    E   K   V    K   L   P
281  TTCAAAGATG GCCAACTGCA AGGGACAAAT CTCAAGTCCA TATCTGCCAA TGAGAAAGTC AAGCTGCCAC
     L   V   I   S    F   L   E    S   G   A    A   R   I   V    V   D   E    E   K   R    M   K   G   E
351  TTGTGATTTC TTTCCTGGAG TCTGGAGCTG CGGCCATCGT GGTCGACGAG GAGAAGCGGA TGAAGGGCGA
     I   D   L    R   H   N    S   Q   V   R    K   E   R    Y   N   E    A   E   Q   N    A   L   V
421  AATTGACCTC CGACATAACA GCCAAGTGCG CAAAGAGCGA TACAATGAAG CAGAGCAATG GGCACTGGTT
     G   G   L    E   S   S   K    T   A   A    V   D   T    E   S   E   T    G   F   T    K   V   L
491  GGTGGTTTGG AATGGAGCAA AACTGCCGCT GTGCACACAG AATCCGAGAC TGGATTCACA AAGGTACTTT
     Y   G   P   D    N   K   F    Q   A   I    I   R   H   A    P   F   S    V   D   F    Q   R   D   G
561  ACGGGCCCGA TAACAAGTTT CAGGCCAATCA TTCGCCATGC GCCGTTCAGC GTTGATTTTC AGCGCGATGG
     Q   S   H    V   R   V    N   H   K   G    P   L   N    V   E   H    W   R   P   K    V   D   V
631  CCAGAGCCAT GTCCGACTGA ATCACAAGGG CTTCCTCAAC GTGGAACACT GGCGGCCAAA GGTGGATGTC
     A   E   G    D   S   V   Q    E   K   S    I   E   Q    Q   D   E   S    T   W   N    E   B   T
701  GCAGAGGGTG ACAGTGTTCA GGAAAAAATCG ATACCTCAGC AAGATGAAAG CACTTGGTGG GAGAAACTT
     F   G   G   N    T   D   S    K   P   K    G   P   E   S    I   G   L    D   I   T    F   P   G   Y
771  TTGGTGGGAA CACCGACTCC AAGGCCAAAG GTCCCGAAAG TATCGGCCTG GACATCACAT TCCCTGGCTA
     S   H   V    F   G   I    P   E   H   A    D   S   M    S   L   K    E   T   R
841  CAGCCATGTT TTTGGGATTC CAGAGCATGC CGACTCGATG TCTCTGAAGG AAACCAGGTA GGTGTTACAT
                                                                                G   G   D    G   N   H    A   E   P
911  GTCCCTTGCCC CTCTAGAGAC GCAAAGTCGA TCAGTTTGAA GGGGCGGTGA AAACCAGTCA TGGAAATCAT GCGGAACTTT
     Y   R   M   Y    N   T   D    V   F   E    Y   E   L   N    S   P   M    T   L   Y    G   A   I   P
981  ATCGGCATGTA CAATACGGAC GTCTTTGAAT ATGAACTCAA CAGTCCCATG ACGCTCTATG GGGCCATTCC
```

Fig. 2A

```
       F  M  Q     A  H  K     K  D  S  T     V  G  V     F  W  L     N  A  A  E     T  W  V
1051  GTTCATGCAG  GCTCACAAGA  AGGACTCTAC  TGTGGGTGTC  TTCTGGCTGA  ACGGTGCGGA  GACCTGGGTC
       D  I  V     S  P  D     S  P  D     P  L  S     L  G  V  G     S  K  T     D  T  Q
1121  GACATCGTCA  AGTCGGAAATC  CTCGCCCGAC  CCTCTTTCTC  TTGGAGTAGG  TTCGAAGACA  GACACCCAAA
       T  H  W  F     S  E  S     G  R  I     D  L  F  V     P  L  G     P  T  P     Q  E  I  S
1191  CTCATTGGTT  TTCCGAGTCG  GGACGTATTG  ATTTGTTTGT  CTTCTTGGGC  CCCACTCCGC  AAGAGATCAG
       K  T  Y     G  E  L     T  G  Y  T     Q  L  P     Q  Q  F     A  I  A  Y     H  Q  C
1261  CAAAACATAC  GGTGAACTTA  CCGGCTACAC  CAATTACCT  CAACAGTTC  CTATCGCTTA  CCACCAGTGT
       R  W  N     Y  V  T  D     E  D  V     K  E  V     D  R  K  F     D  K  Y     Q  I  P
1331  CGTTGGAACT  ATGTCACGGA  CGAGGATGTC  AAGGAAGTTG  ATCGCAAGTT  TGACAAGTAT  CAGATCCCTT
       Y  D  V  I     W  L  D     I  E  Y     T  D  D  R     K  Y  F     T  W  D     P  L  S  F
1401  ACGATGTCAT  TTGGCTTGAC  ATTGAGTACA  CGGATGACCG  AAGTACTTT  ACCTGGGACC  CTCTGAGTTT
       P  D  P     K  G  M     E  E  Q  L     E  E  R  K     L  V  V  I     I  D  P
1471  TCCTGACCCG  AAGGGTATGG  AAGAGCAGCT  TGAAGACTCC  GAGCGCAAAC  TCGTTGTGAT  CATTGACCCG
       H  I  K     N  K  E  G     V  S  I     S  H  E     L  K  G  K     D  L  A     I  K  N
1541  CACATTAAAA  ACAAGGAAGG  ATACTCCATC  TCTCACGAGC  TGAAGGGCAA  TGATCTGGCT  ATTAAGAACA
       K  G  G  E     T  Y  D     G  W  C     W  P  G  S     S  H  W     V  D  C     F  N  P  E
1611  AGGGCGGGGA  GACCTACGAC  GGCTGGTGTT  GGCCTGGTTC  ATCTCACTGG  GTGGACTGCT  TCAATCCCGA
       A  I  K     W  N  T     G  L  F  K     Y  D  K     F  K  G     T  Q  P  N     V  F  I
1681  AGCAATCAAG  TGGTGGACCG  GCTTGTTCAA  GTACGACAAA  TTCAAGGCA  CCCAGCCAAA  CGTCTTTATT
       W  N  D     M  N  E  P     S  V  P     N  G  P     E  T  T  M     P  K  D     N  I  H
1751  TGGAATGACA  TGAATGAGCC  CTCTGTCTTC  AATGGACCGG  AAAACCACTAT  GCCCAAAGAC  AATATCCACT
       Y  G  N  W     B  H  R     D  V  H     N  V  N  G     L  T  P     I  N  A     T  Y  N  A
1821  ATCGCAACTG  GGAACACCGC  GACGTGCATA  ATGTCAACGG  ACTGACCTTT  ATCAACGCAA  CATACAATGC
       L  E     R  K  K     G  V  R     R  P  F     V  L  T     R  S  F  Y     A  G  A
1891  CTTACTGGAG  CGGAAGAAAG  GCGTGGTTCG  TCGGCCCTTC  GTCTTGACCC  GATCATTCTA  CGCCGGGGCT
       Q  R  V     S  A  M  W     T  G  D     N  Q  A     T  W  E  H     L  A  A     S  L  P
1961  CAACGGGTAT  CTTGCTATGT  GACGGGAGAC  AATCAAGCCA  CCTGGGAACA  TCTGGCCGCA  TCCTTGCCTA
       M  V  L  N     N  G  I     A  G  F     P  F  A  G     A  D  V     T  W  E  H     G  G  F     F  Q  N  P
```

Fig. 2B

```
2031  TGGTATTGAA TAACGGCATT GCCTGGGTTCC CGTTTGCCGG TGCCGATGTT GGCGGGTTTT TCCAGAACCC
        S  K  E   L  L  T    R  W  Y  Q    A  G  I    W  Y  P    F  F  R  A    H  A  H
2101  AAGCAAGGAA CTTTTGACCC GGTGGTATCA GGCCTGGCAT TGGTATCCCT TCTTCCGTGC CCATGCGCAC
        I  D  T   R  R  R  E   P  Y  L    I  A  E    P  F  R  S    I  I  S    Q  A  I
2171  ATTGACACTC GCAGAGAGA GCCCTACTTG ATCGCTGAGC CATTCAGGTC GATCATATCC CAGGCTATCC
        R  L  R  Y   Q  L  L    P  A  W    Y  T  A  F   H  E  A    S  V  N    G  M  P  I
2241  GTCTGAGATA TCAACTGCTG CCTGCATGGT ACACTGCTTT TCATGAAGCT TCGGTGAATG GAATGCCTAT
        V  R  P   Q  Y  Y   V  H  P  A   D  E  Q    G  F  A    I  D  D  Q    L  Y  L
2311  TGTTCCGCCC CAGTATTATG TCCCACCCGGC GGACCAACAA GGCTTTGCCA TTGATGACCA ACTCTACCTT
        G  S  T   G  L  L  A   K  P  V    V  V  E    G  A  T  T   T  D  I    Y  I  A
2381  GGATCTACTG GCCTGCTGGC CAAACCTGTG GTTGTGGAGG GTGCCACCAC TACAGATATC TACATCGCTG
        D  D  E  K   Y  Y  D    Y  Y  D    F  T  V  Y    Q  G  A    G  R  R    H  T  V  P
2451  ACGATGAGAA GTACTACGAT TACTATGATT TTACTGTCTA CCAAGGAGCG GCCAGGAGAC ATACGGTGCC
        S  P  I  E   K  V   P  L  L  M    Q  G  G    H  I  I    P  R  K  D    R  A  R
2521  TTCCCCCATT CAGAAGGTCC CATTGTTGAT GCAAGGAGGT CATATTATCC CTCGCAAGGA CCCGCCACGT
        R  S  S   G  L  M  R    W  D  P    Y  T  L    V  I  V  L    D  K  N    G  K  A
2591  CGTAGCAGCG GGCTGATGAG ATGGGATCCT TATACACTTG TGATCGTCCT CGACAAGAAC GGGAAGGCCG
        E  G  T  L   Y  V  D    D  G  E   S  F  N  Y    Q  Q  G    A  Y  I    H  R  R  F
2661  AAGGCACACT CTATGTTGAT GATGGGGAGT CGTTCAACTA CCAGCAGGGT GCATACATAC ACCGTCGCTT
        K  F  E   K  S  T    L  L  S  E   D  I  G    T  K  G    S  K  T  A    R  Y  L
2731  CAAATTTGAA AAATCTACCC TTTTCTCGGA AGACATCGGC ACCAAGGGTT CGAAGACAGC CGAATACTTG
        K  S  M   T  N  V  R    V  Q  K    V  V  V    V  D  A  P    K  E  W    Q  G  R
2801  AAGAGCATGA CGAATGTGCG GGTTCAAAAG GTGGTTGTTG TGGACGCTCC CAAGGAGTGG CAGGGAAGGA
        T  S  V  T   V  I  E    D  G  A    K  M  A  S    T  A  P    L  E  Y    H  A  Q  Q
2871  CGTCTGTGAC CGTCATCGAA GACGGTGCAA AGATGGCTTC TACCGCACCC TTGGAGTATC ACGCCCAGCA
        A  G  K   A  A  Y    A  V  V  K   K  P  D    V  G  I    G  K  T  W    K  I  E
2941  GGCCAGGCAAG GCTGCCTATG CTGTCGTGAA GAAACCCGAT GTTGGCATTG GAAAGACATG GAAGATTGAA
        F  *
3011  TTCTAA
```

Fig. 2C

```
  1 ATGGCCAGCGTCCTGGGCCTCGTCGCCAGTGCCTGGCTCCTCCCCACGGCCTATGGGGCA
    M  A  S  V  L  G  L  V  A  S  A  W  L  L  P  T  A  Y  G  A
 61 AGCCATTGCTTGCGCCTAGCACGTCCGCAACCTCAGCACAGGCGCAAATACTTACCA
    S  H  S  L  A  P  S  T  S  A  Q  A  Q  Y  T  L  P
121 TCTTCTATTGACGTTGGCGCTCACTTGGCCAACATCGACGATCCCCTTGCCGTGGAC
    S  S  I  D  V  G  A  H  L  I  A  N  I  D  D  P  L  A  V  D
181 GCGCAGTCTGTGTGTCCCGGCTACACAGCCTCAGATGCCACCAGACATCCATGGTTTC
    A  Q  S  V  C  P  G  Y  T  A  S  D  V  H  Q  T  S  H  G  F
241 ACCGCTAACCTACAGCTCGCGGGTGACCATGCAACGTGTACGGGACAGAGCGTTGATTCG
    T  A  N  L  Q  L  A  G  D  P  C  N  V  G  T  D  V  D  S
301 CTGTCTCTGACAGTGGATTATTGGCAAGGACCGCCTGAATATCCAAGTTGTTCCTACC
    L  S  L  T  V  D  Y  L  A  K  D  R  L  N  I  Q  V  V  P  T
361 CACGTGGATGCCCTCCAACGTTCTTGGTACCTCCTCTCGGAAGATTGGTGCCCGGGCT
    H  V  D  A  S  N  A  S  W  Y  L  L  S  E  D  L  V  P  R  A
421 CATGGCCCTGGCGTGTCGCCCTCAAAGCGACTTTGAAAGTGAAGTGGTCCAACGAGCCT
    H  G  P  G  V  S  A  S  Q  S  D  F  E  V  K  W  S  N  E  P
481 TCTTTCAACCTCAAGGTCATTCGCAAGGCTACTCGGAGACGTCCTCTTGATACCGAGGGC
    S  F  N  L  K  V  I  R  K  A  T  G  D  V  L  F  D  T  E  G
541 TCTGTCTTGGTCTTTGAGAACCAGTTTATCGAGTTTGTCTCTTCGTTGCCTGAGGGTTAC
    S  V  L  V  F  E  N  Q  F  I  E  F  V  S  S  L  P  E  G  Y
601 AACCTGTACGGGCTGGGAGAGAGGCATGGCCAGCGCTGGCTCTTGAGAAACGCGACCCTG
    N  L  Y  G  L  G  E  R  M  A  Q  R  L  L  R  N  A  T  L
661 ACCACCTATGCGGATGTGGGAGACCCGATTGATAGGTATGTTGCTGGCCATGGTTGA
    T  T  Y  A  A  D  V  G  D  P  I  D  R
721 AATCTAAATGTACGAAGTCGACAAGCTTACAATCGGCTCTCCACAGCAACATCTATGGACA
                       N  I  Y  G  Q
        H  P  F  Y  L  D  T  R  Y  Y  T  K  G  A  N  G  S  Y  S  L
```

Fig. 3A

```
 781  GCATCCGTTCTACCTTCGACACTCGATATACACCAAAGGCGGAATGGGTCCTACTCGCT
        V  N  A  D  E  A  D  L  S  E  D  H  E  S  F  S  H  G  V  P
 841  TGTCAACGCCGACGAGGCGGACTTGTCGGAGGATCATGAATCATTCTCCCACGGTGTCTT
        L  R  N  A  H  G  Q  E  V  L  L  Q  P  R  N  I  T  W  R  T
 901  TCTGAGAAACGCTCATGGTCAGGAAGTTCTCCTGCAGCCCCGCAACATTACCTGGCGCAC
        I  G  G  S  I  D  L  T  F  Y  S  G  P  T  Q  A  D  V  T  K
 961  AATTGGTGGTAGCATCGATCTGACTTTCTACTCCGGTCCCACGCAAGCGGACGTCACAAA
        S  Y  Q  L  S  T  I  G  L  P  A  M  Q  Q  Y  S  A  L  G  Y
1021  GAGCTACCAGCTCTCCACTATTGGACTTCCTGCAATGCAGCAGTACAGCGCCCTTGGATA
        H  Q  C  R  W  G  Y  Q  N  W  S  Q  L  E  V  N  N  F
1081  CCACCAATGCCGCTGGGGCTACCAGAATTGGTCTCAGTCTCGAGGAAGTAGTCAACAACTT
        E  R  F  E  I  P  L  E  Y  I  W             S  D  I  D  Y  M  L  G
1141  TGAGCGATTTGAGATTCCTCTGGAATACATCTGGTCAGTCGGTTTCTGAGTTTCTTACAT
        Y  R  D  F  E  N  D  P  E  R  F  S  Y  D  E  G  E  E  F  L
1201  ATTGTCCTAGTTTCTTTTATTTACCTTCCTTCCAGGAGCGACATCGATTACATGCTTGGC
        N  K  L  H  K  S  G  R  H  W  V  P  I  V  D  S  A  I  Y  I
1261  TACCGGGACTTTGAGAATGATCCCGAACGGTTCTCCTACGATGAAGGCGAGGAATTTCTG
        P  N  P  D  N  A  L  D  A
1321  AACAAACTGCACAAGTCACACGACGACACTGGGGACGACACTGGGTTGACTCGGCAATCTATATT
        Y  E  P  Y  A  R  G
1381  CCCAACCCCGACAATGCATTGGATGCTAAGTCCTTATTATCTTATCCTCCTTGTGAGAT
        A  K  D  D  V  F  I  K  N  P  D  G  T  L  Y  I  G  A  V  W
1441  GGTCAAGTTCAAGTTCTCACGAAAGTGTGAACTCCAGGTACGAGACCCTTATGCTCGGGGG

Fig. 3B
```

```
1501  CAAAGGATGACGTTTTTATCAAGAACCCTGATGGCACCCTCTACATCGGTGCAGTGTGGC
       P  G  F  T  V  F  P  D  W  H  N  P  K  A  F  D  Y  W  A  N
1561  CGGGCTTTACTGTCTTCCCCGATTGGCACAACCCAAGGCATTTGACTACTGGGCCAACG
       E  L  V  I  W  S  K  K  V  A  F  D  G  I  W  I  D  M  S  E
1621  AACTCGTCATCTGGTCAAAGAAGTTGCCTTCGATGGCATCTGGATTGATATGAGCGAAG
       V  S  F  C  V  G  S  C  G  T  G  K  L  H  L  N  P  V  H
1681  TATCCTTCTTTCTGCGGTGGGACAGGAAAGCTACATCTGACCGGTTCACC
       P  P  F  Q  L  P  G  E  P  G  N  V  G  Y  D  Y  P  E  A  F
1741  CACCATTCCAGCTTCCCGGTGAACCTGGCAATGTCGGCTACGACTACCCGGAGGCCTTCA
       N  V  T  N  S  T  E  A  A  S  A  A  S  A  S  Q  A  S
1801  ACGTGACGAACTCTACCGAAGCGGCCTCTGCCGCCAGTGCCAGTGCCCAGGCTTCGG
       A  A  S  A  T  Q  A  A  T  T  S  T  S  Y  L  R  T  T
1861  CTGCTTCTGCTACCCAAGCCGCCACGACGTCAACTACATCTACATCGTATCTGCCGACGACGC
       P  T  P  G  V  R  D  V  N  Y  P  P  Y  V  I  N  H  V  Q  E
1921  CCACGCCGGGCGTCCGCAGTCGGCGTCACTGGCCATGTTGATTAATCATGTTCAGGAGG
       G  H  D  L  A  V  H  A  I  S  P  N  S  T  H  V  D  G  V  Q
1981  GCCATGACCTTGCCGTCCACGCCATTTCTCCCAACTCCACCCATGTGGACGGGGTCCAGG
       E  Y  D  V  H  S  L  W  G  H  Q  I  L  N  A  T  Y  Y  G  L
2041  AATACGATGTTCACAGTCTGTGGGGCCACCAGATCCTCAATGCTACCTACTACGGACTGC
       R  Q  V  F  T  E  K  R  P  F  I  I  G  R  S  T  F  A  G  S
2101  GCCAGGTCTTCACTGAGAAGCGACCTTTTCATCATTGGCCGGTCTACCTTGCTGGCTCGG
       G  K  W  A  G  H  W  G  G  D  N  S  K  W  G  S  M  F  L
2161  GCAAGTGGGCCGGTCACTGGGGCGGTGATAACAACTCCAAATGGGGGTCCATGTTCCTGT
       S  I  S  Q  G  L  S  F  L  F  G  I  P  M  F  G  V  D  T
2221  CCATCTCGCAGGGTCTGTCGTTCCTCGCTATTCGGCTATTCGGGGTGGATACAT
       C  G  F  N  G  N  T  D  E  E  L  C  S  R  W  M  Q  L  S  A
```

Fig. 3C

```
2281  GCGGTTTCAACGGCAACACTGACGAGGAGCTTTGCAGCCGGTGGATGCAGCTGTCGGCCT
       F   F   P   F   Y   R   N   H   N   V   L   A   A   I   P   Q   E   P   Y   R
2341  TCTTCCCTTCTACCGCAACCACAATGTCCTTGCGGCTATCCCCAGGAACCCTACCGCT
       S   F   P   S   T   A   T   T   M   S   L   R   L   S   P   G   T   L   P   L
2401  GGGCCTCTGTCGCCCAAGCCTGCGCCGTATGAAGATCCGGCTATTCCCTCCTACCTT
       W   A   S   V   A   Q   A   S   K   A   A   M   K   I   R   Y   S   L   L   P
2461  ACTTCTACACTCTTTTTCCACCAGGCCCACACCACCGGCTCTACCGTCATGCGCTCTCG
       Y   F   Y   T   L   F   H   Q   A   H   T   T   G   S   T   V   M   R   A   L
2521  GCTTGGGAGTTCCCCACGGACCCGTCCCTGGCCGCCGTCGACACTCAGTTCATGGTCGGCC
       A   W   E   F   P   T   D   P   S   L   A   A   V   D   T   Q   F   M   V   G
2581  CTTCCATCATGGTCGTCCCCGTGCTTGAGCCCCTGGCCGATACCGTCAAGGGCGTGTTT
       P   S   I   M   V   V   P   V   L   E   P   L   A   D   T   V   K   G   V   F
2641  CAGGCCGTCGGCAAAGGCGAAGTGGATTGGTACGACTGGTACACCCAGACCGCCGTGGACCCCA
       P   G   V   G   K   G   E   V   D   W   Y   D   W   Y   T   Q   T   A   V   D   A
2701  AACCCGGCGTCAACGCCACCATTCCCGCACCGCTGGGCCACATCCCGTCTATGTCCGTG
       K   P   G   V   N   A   T   I   P   A   P   L   G   H   I   P   V   Y   V   R
2761  GAGCCAGCATCCTGCCCATGCAGGAGCCCGCTTCACGACGAGACGCCTAACACTC
       Q   E   P   A   L   T   T   R   D   A   R   N   T
2821  CCTGGTCTCTACTCGTCGCTCTGAGTGGCCACCAGACTGCCTTGGCCTCGCTGTATCTTG
       P   W   S   L   L   V   A   L   S   G   N   Q   T   A   L   G   S   L   Y   L
2881  ACGACGGAAGCAGCCTCAACCCGTCCGACTTCGATGTCGACTTCCAGGCTACAGCCT
       D   D   G   S   S   L   N   P   S   R   T   L   D   V   D   F   Q   A   T   A
2941  CGAGCATCAAGGTCTGGTCAAGGGTACCTGGGAGGAGAAGAACCGCCTGGATAAGGTGA
       S   S   I   K   V   S   V   K   G   T   W   E   E   K   N   R   L   D   K   V
       T   V   L   G   V   T   E   K   P   S   A   V   T   F   N   G   R   N   V   H
```

Fig. 3D

```
3001 CTGTCCTCCTCGGCGTGACTGAGAAGCCTTCTGCTCTGACGTTCAACGGCCGCAACGTCCACC
      P  V  L  L  G  V  T  E  K  P  S  A  L  T  F  N  G  R  N  V  H  
3061 CTGGCTCAGTGCCACTACTACAATACTACCACCAAGGTCCTGTCTGTGCAGGGATTGCACAGCA
      L  A  Q  C  H  Y  Y  N  T  T  T  K  V  L  S  V  Q  G  L  H  S  
3121 TGACTCCCCATGGGCGCTGGGCTGGAGCTGGACACTGGATTCTGAAAATGGTAG
      M  T  P  H  G  A  W  A  G  H  W  I  L  K  W  *
```

Fig. 3E

POLYPEPTIDES HAVING ALPHA-GLUCOSIDASE ACTIVITY AND POLYNUCLEOTIDES ENCODING SAME

CROSS-REFERENCE TO RELATED APPLICATIONS

This application is a divisional of U.S. application Ser. No. 11/171,701 (now U.S. Pat. No. 8,633,006) filed Jun. 29, 2005, which claims the benefit of U.S. Provisional Application No. 60/585,336 (expired), filed on Jun. 29, 2004, which application is fully incorporated herein by reference.

BACKGROUND OF THE INVENTION

Field of the Invention

The present invention relates to isolated polypeptides having alpha-glucosidase activity and isolated polynucleotides encoding the polypeptides. The invention also relates to nucleic acid constructs, vectors, and host cells comprising the polynucleotides as well as methods for producing and using the polypeptides.

Description of the Related Art

Several enzymes are involved in the degradation of starch. The enzymes include alpha-amylase, beta-amylase, amyloglucosidase, pullulanase, isoamylase, alpha-glucosidase, and cylcodextrin glycosyltransferase.

Alpha-glucosidases (EC 3.2.1.20) hydrolyze terminal, non-reducing alpha-1,4-linked glucose residues in various substrates, releasing glucose. They degrade disaccharides and oligosaccharides quickly while polysaccharides are attacked slowly if at all. Maltose, maltose derivatives, sucrose, aryl-alpha-glucosides, and alkyl-alpha-glucosides can act as substrates.

The purification and properties of an alpha-glucosidase from *Aspergillus fumigatus* has been described by Rudick and Elbein, 1974, *Archives of Biochemistry and Biophysics* 161: 281-290.

Other filamentous fungi have been reported to produce alpha-glucosidases such as *Aspergillus flavus* (Olutiola, 1981, *Mycologia* 73: 1130), *Aspergillus nidulans* (Kato et al., 2002, *Appl. Environ. Microbiol.* 68: 1250-1256), *Aspergillus niger* (Rudick et al., 1979, *Archives of Biochemistry and Biophysics* 193: 509), *Aspergillus oryzae* (Leibowitz and Mechlinski, 1926, *Hoppe-Seyler's Zeitschrift für Physiologische Chemie* 154: 64), *Mucor javanicus* (Yamasaki et al., 1978, *Berichte des Ohara Instituts für Landwirtschaftliche Biologie* 17: 123), *Mucor racemosus* (Yamasaki et al., 1977, *Agricultural and Biological Chemistry* 41: 1553), *Mucor rouxii* (Flores-Carreon and Ruiz-Herrera, 1972, *Biochemica et Biophysica Acta* 258: 496), *Penicillium pupurogenum* (Yamasaki et al., 1976, *Agricultural and Biological Chemistry* 40: 669), and *Penicillium oxalicum* (Yamasaki et al., 1977, *Agricultural and Biological Chemistry* 41: 1451).

Alpha-glucosidases can be used in combination with other starch-degrading enzymes, e.g., alpha-amylase, to achieve complete hydrolysis of starch in industrial applications where conversion to fermentable sugars is desirable. Consequently, there is a need in the art for alternative alpha-glucosidases with improved properties such as pH optimum, temperature optimum, and thermostability.

It is an object of the present invention to provide polypeptides having alpha-glucosidase activity and polynucleotides encoding the polypeptides.

SUMMARY OF THE INVENTION

The present invention relates to isolated polypeptides having alpha-glucosidase activity selected from the group consisting of:

(a) a polypeptide having an amino acid sequence which has at least 75% identity with amino acids 15 to 881 of SEQ ID NO: 2 or amino acids 30 to 967 of SEQ ID NO: 4 or at least 85% identity with amino acids 20 to 988 of SEQ ID NO: 6;

(b) a polypeptide which is encoded by a nucleotide sequence which hybridizes under medium stringency conditions with (i) nucleotides 43 to 2643 of SEQ ID NO: 1 or nucleotides 146 to 3013 of SEQ ID NO: 3, (ii) the cDNA sequence contained in nucleotides 43 to 2643 of SEQ ID NO: 1 or nucleotides 146 to 3013 of SEQ ID NO: 3, or (iii) a complementary strand of (i) or (ii), or under high stringency conditions with (i) nucleotides 58 to 3164 of SEQ ID NO: 5, (ii) the cDNA sequence contained in nucleotides 58 to 3164 of SEQ ID NO: 5, or (iii) a complementary strand of (i) or (ii); and (c) a variant comprising a conservative substitution, deletion, and/or insertion of one or more amino acids of amino acids 15 to 881 of SEQ ID NO: 2, amino acids 30 to 967 of SEQ ID NO: 4, or amino acids 20 to 988 of SEQ ID NO: 6.

The present invention also relates to isolated polynucleotides encoding polypeptides having alpha-glucosidase activity, selected from the group consisting of:

(a) a polynucleotide encoding a polypeptide having an amino acid sequence which has at least 75% identity with amino acids 15 to 881 of SEQ ID NO: 2 or amino acids 30 to 967 of SEQ ID NO: 4 or at least 85% identity with amino acids 20 to 988 of SEQ ID NO: 6;

(b) a polynucleotide having at least 75% identity with nucleotides 43 to 2643 of SEQ ID NO: 1 or nucleotides 146 to 3013 of SEQ ID NO: 3 or at least 85% identity with nucleotides 58 to 3164 of SEQ ID NO: 5; and (c) a polynucleotide which hybridizes under medium stringency conditions with (i) nucleotides 43 to 2643 of SEQ ID NO: 1 or nucleotides 146 to 3013 of SEQ ID NO: 3, (ii) the cDNA sequence contained in nucleotides 43 to 2643 of SEQ ID NO: 1 or nucleotides 146 to 3013 of SEQ ID NO: 3, or (iii) a complementary strand of (i) or (ii), or under high stringency conditions with (i) nucleotides 58 to 3164 of SEQ ID NO: 5, (ii) the cDNA sequence contained in nucleotides 58 to 3164 of SEQ ID NO: 5, or (iii) a complementary strand of (i) or (ii).

The present invention also relates to nucleic acid constructs, recombinant expression vectors, and recombinant host cells comprising the polynucleotides.

The present invention also relates to methods for producing such polypeptides having alpha-glucosidase activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the alpha-glucosidases.

The present invention further relates to nucleic acid constructs comprising a gene encoding a protein, wherein the gene is operably linked to a nucleotide sequence encoding a signal peptide, wherein the nucleotide sequence consists of nucleotides 1 to 42 of SEQ ID NO: 1, nucleotides 1 to 145 of SEQ ID NO: 3, or nucleotides 1 to 57 of SEQ ID NO: 5, and the gene is foreign to the nucleotide sequence.

BRIEF DESCRIPTION OF THE FIGURES

FIGS. 1(*a*), (*b*), (*c*), (*d*) and (*e*) show the genomic DNA sequence and the deduced amino acid sequence of an *Aspergillus fumigatus* alpha-glucosidase (Agl1) (SEQ ID NOs: 1 and 2, respectively).

FIGS. 2(a), (b) and (c) show the genomic DNA sequence and the deduced amino acid sequence of an *Aspergillus fumigatus* alpha-glucosidase (Agl2) (SEQ ID NOs: 3 and 4, respectively).

FIGS. 3(a), (b), (c), (d) and (e) show the genomic DNA sequence and the deduced amino acid sequence of an *Aspergillus fumigatus* alpha-glucosidase (Agl3) (SEQ ID NOs: 5 and 6, respectively).

FIG. 6 shows a restriction map of pBM120a.

DEFINITIONS

Figure 4:
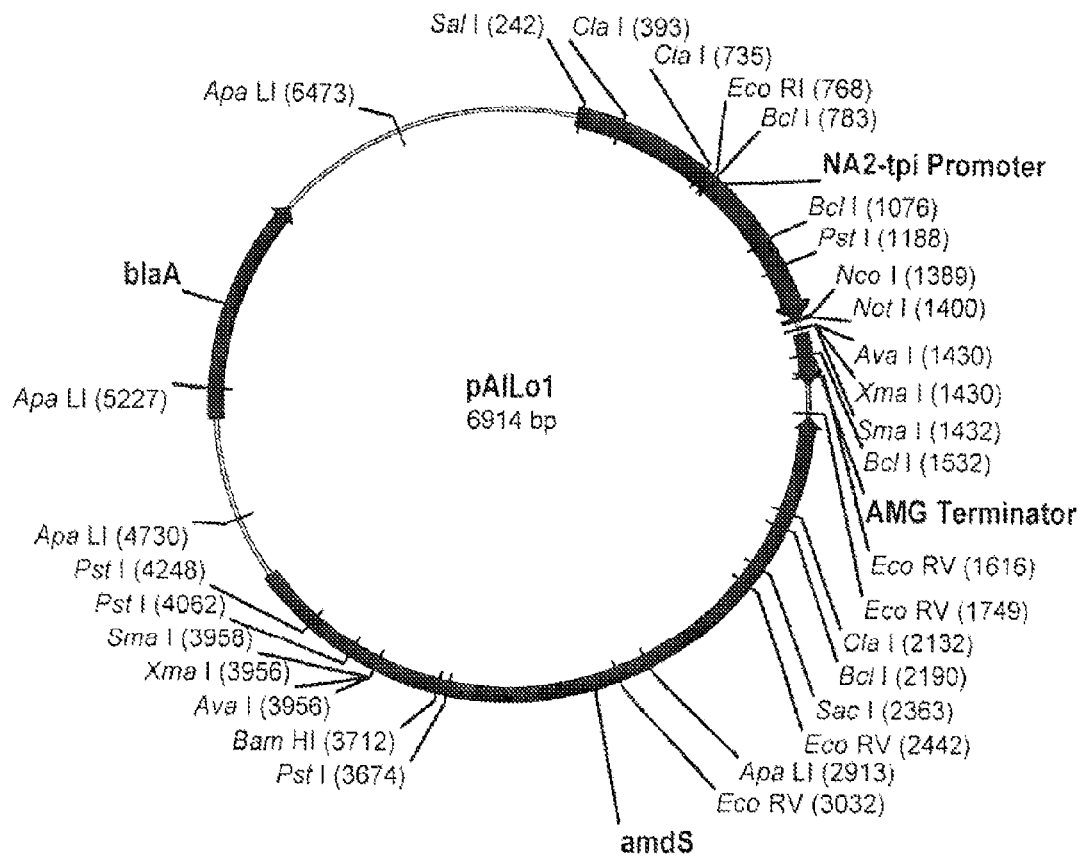
FIG. 4 shows a restriction map of pAILo1.

Alpha-glucosidase activity: The term "alpha-glucosidase activity" is defined herein as an alpha-D-glucoside glucohydrolase activity (E.C. 3.2.1.20) which catalyzes the exo-hydrolysis of terminal, non-reducing 1,4-linked alpha-D-glucose residues with the release of alpha-D-glucose. Natural substrates of the enzyme activity include, for example, maltose, maltotriose, maltotetraose, maltopentaose, starch (soluble), amylose, amylopectin, isomaltose, Kojibiose, sucrose, nigerose, turanose, melizitose, and glycogen. For purposes of the present invention, alpha-glucosidase activity is determined with maltose as substrate in 0.1 M sodium acetate buffer pH 4.3 at 25° C. One unit of alpha-glucosidase activity is defined as 1.0 mmole of glucose produced per minute at 25° C., pH 4.3 from maltose as substrate in sodium acetate buffer.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the alpha-glucosidase activity of the polypeptide consisting of the amino acid sequence shown as amino acids 15 to 881 of SEQ ID NO: 2, amino acids 30 to 967 of SEQ ID NO: 4, or amino acids 20 to 988 of SEQ ID NO: 6.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively or recombinantly associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment: The term "polypeptide fragment" is defined herein as a polypeptide having one or more amino acids deleted from the amino and/or carboxyl terminus of an amino acid sequence or a homologue thereof, wherein the fragment has alpha-glucosidase activity. In a preferred aspect, a fragment contains at least 770 amino acid residues, more preferably at least 800 amino acid residues, and most preferably at least 830 amino acid residues of SEQ ID NO: 2 or a homologue thereof. In another preferred aspect, a fragment contains at least 820 amino acid residues, more preferably at least 860 amino acid residues, and most preferably at least 900 amino acid residues of SEQ ID NO: 4 or a homologue thereof. In another preferred aspect, a fragment contains at least 820 amino acid residues, more preferably at least 860 amino acid residues, and most preferably at least 900 amino acid residues of SEQ ID NO: 6 or a homologue thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively or recombinantly associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Subsequence: The term "subsequence" is defined herein as a nucleotide sequence having one or more nucleotides deleted from the 5' and/or 3' end of a polynucleotide or a homologue thereof, wherein the subsequence encodes a polypeptide fragment having alpha-glucosidase activity. In a preferred aspect, a subsequence contains at least 2310 nucleotides, more preferably at least 2400 nucleotides, and most preferably at least 2490 nucleotides of SEQ ID NO: 1 or a homologue thereof. In another preferred aspect, a subsequence contains at least 2460 nucleotides, more preferably at least 2580 nucleotides, and most preferably at least 2700 nucleotides of SEQ ID NO: 3 or a homologue thereof. In another preferred aspect, a subsequence contains at least 2460 nucleotides, more preferably at least 2580 nucleotides, and most preferably at least 2700 nucleotides of SEQ ID NO: 5 or a homologue thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TM, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the amino acids 15 to 881 of SEQ ID NO: 2, amino acids 30 to 967 of SEQ ID NO: 4, or amino acids 20 to 988 of SEQ ID NO: 6, or a homologous sequence thereof, as well as genetic manipulation of the DNA encoding that polypeptide. The modification can be substitutions, deletions and/or insertions of one or more amino acids as well as replacements of one or more amino acid side chains.

Artificial variant: When used herein, the term "artificial variant" means a polypeptide having alpha-glucosidase activity produced by an organism expressing a modified nucleotide sequence of SEQ ID NO: 1, SEQ ID NO: 3, or SEQ ID NO: 5. The modified nucleotide sequence is obtained through human intervention by modification of the nucleotide sequence disclosed in SEQ ID NO: 1, SEQ ID NO: 3, or SEQ ID NO:5.

DETAILED DESCRIPTION OF THE INVENTION

Polypeptides Having Alpha-Glucosidase Activity

In a first aspect, the present invention relates to isolated polypeptides having an amino acid sequence which has a degree of identity to amino acids 15 to 881 of SEQ ID NO: 2 or amino acids 30 to 967 of SEQ ID NO: 4 (i.e., the mature polypeptide) of at least 75%, preferably at least 80%, more preferably at least 85%, even more preferably at least 90%, most preferably at least 95%, and even most preferably at least 97%, which have alpha-glucosidase activity, or to amino acids 20 to 988 of SEQ ID NO: 6 (i.e., the mature polypeptide) of at least 85%, preferably at least 90%, more preferably at least 95%, and most preferably at least 97%, which have alpha-glucosidase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 15 to 881 of SEQ ID NO: 2, amino acids 30 to 967 of SEQ ID NO: 4, or amino acids 20 to 988 of SEQ ID NO: 6.

A polypeptide of the present invention preferably comprises the amino acid sequence of SEQ ID NO: 2, or an allelic variant thereof; or a fragment thereof that has alpha-glucosidase activity. In a preferred aspect, a polypeptide comprises the amino acid sequence of SEQ ID NO: 2. In another preferred aspect, a polypeptide comprises amino acids 15 to 881 of SEQ ID NO: 2, or an allelic variant thereof; or a fragment thereof that has alpha-glucosidase activity. In another preferred aspect, a polypeptide comprises amino acids 15 to 881 of SEQ ID NO: 2. In another preferred aspect, a polypeptide consists of the amino acid sequence of SEQ ID NO: 2 or an allelic variant thereof; or a fragment thereof that has alpha-glucosidase activity. In another preferred aspect, a polypeptide consists of the amino acid sequence of SEQ ID NO: 2. In another preferred aspect, a polypeptide consists of amino acids 15 to 881 of SEQ ID NO: 2 or an allelic variant thereof; or a fragment thereof that has alpha-glucosidase activity. In another preferred aspect, a polypeptide consists of amino acids 15 to 881 of SEQ ID NO: 2.

A polypeptide of the present invention preferably comprises the amino acid sequence of SEQ ID NO: 4, or an allelic variant thereof; or a fragment thereof that has alpha-glucosidase activity. In a preferred aspect, a polypeptide comprises the amino acid sequence of SEQ ID NO: 4. In another preferred aspect, a polypeptide comprises amino acids 30 to 967 of SEQ ID NO: 4, or an allelic variant thereof; or a fragment thereof that has alpha-glucosidase activity. In another preferred aspect, a polypeptide comprises amino acids 30 to 967 of SEQ ID NO: 4. In another preferred aspect, a polypeptide consists of the amino acid sequence of SEQ ID NO: 4 or an allelic variant thereof; or a fragment thereof that has alpha-glucosidase activity. In another preferred aspect, a polypeptide consists of the amino acid sequence of SEQ ID NO: 4. In another preferred aspect, a polypeptide consists of amino acids 30 to 967 of SEQ ID NO: 4 or an allelic variant thereof; or a fragment thereof that has alpha-glucosidase activity. In another preferred aspect, a polypeptide consists of amino acids 30 to 967 of SEQ ID NO: 4.

A polypeptide of the present invention preferably comprises the amino acid sequence of SEQ ID NO: 6, or an allelic variant thereof; or a fragment thereof that has alpha-glucosidase activity. In a preferred aspect, a polypeptide comprises the amino acid sequence of SEQ ID NO: 6. In another preferred aspect, a polypeptide comprises amino acids 20 to 988 of SEQ ID NO: 6, or an allelic variant thereof; or a fragment thereof that has alpha-glucosidase activity. In another preferred aspect, a polypeptide comprises amino acids 20 to 988 of SEQ ID NO: 6. In another preferred aspect, a polypeptide consists of the amino acid sequence of SEQ ID NO: 6 or an allelic variant thereof; or a fragment thereof that has alpha-glucosidase activity. In another preferred aspect, a polypeptide consists of the amino acid sequence of SEQ ID NO: 6. In another preferred aspect, a polypeptide consists of amino acids 20 to 988 of SEQ ID NO: 6 or an allelic variant thereof; or a fragment thereof that has alpha-glucosidase activity. In another preferred aspect, a polypeptide consists of amino acids 20 to 988 of SEQ ID NO: 6.

In a second aspect, the present invention relates to isolated polypeptides having alpha-glucosidase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 43 to 2643 of SEQ ID NO: 1, nucleotides 146 to 3013 of SEQ ID NO: 3, or nucleotides 58 to 3164 of SEQ ID NO: 5 (ii) the cDNA sequence contained in nucleotides 43 to 2643 of SEQ ID NO: 1, nucleotides 146 to 3013 of SEQ ID NO: 3, or nucleotides 58 to 3164 of SEQ ID NO: 5, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has alpha-glucosidase activity.

The nucleotide sequence of SEQ ID NO: 1, SEQ ID NO: 3, or SEQ ID NO: 5; or subsequence thereof, as well as the amino acid sequence of SEQ ID NO: 2, SEQ ID NO: 4, or SEQ ID NO: 6; or fragments thereof, may be used to design a nucleic acid probe to identify and clone DNA encoding polypeptides having alpha-glucosidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having alpha-glucosidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, SEQ ID NO: 3, or SEQ ID NO: 5, or subsequences thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, SEQ ID NO: 3, or SEQ ID NO: 5, their complementary strands, or subsequences thereof, under very low to very high stringency conditions. Molecules to which the nucleic acid probe hybridizes under these conditions can be detected using X-ray film.

In a preferred aspect, the nucleic acid probe is nucleotides 43 to 2643 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the mature polypeptide coding region of SEQ ID NO: 1. In another preferred aspect, the nucleic acid probe is the polynucleotide sequence contained in plasmid pSMO216 which is contained in E. coli NRRL B-30751, wherein the polynucleotide sequence thereof encodes a polypeptide having alpha-glucosidase activity. In another preferred aspect, the nucleic acid probe is the mature polypeptide coding region contained in plasmid pSMO216 which is contained in E. coli NRRL B-30751.

In another preferred aspect, the nucleic acid probe is nucleotides 146 to 3013 of SEQ ID NO: 3. In another preferred aspect, the nucleic acid probe is a polynucleotide sequence which encodes the polypeptide of SEQ ID NO: 4, or a subsequence thereof. In another preferred aspect, the nucleic acid probe is SEQ ID NO: 3. In another preferred aspect, the nucleic acid probe is the mature polypeptide coding region of SEQ ID NO: 3. In another preferred aspect, the nucleic acid probe is the polynucleotide sequence contained in plasmid pHyGe011 which is contained in E. coli NRRL B-30750, wherein the polynucleotide sequence thereof encodes a polypeptide having alpha-glucosidase activity. In another preferred aspect, the nucleic acid probe is the mature polypeptide coding region contained in plasmid pHyGe011 which is contained in E. coli NRRL B-30750.

In another preferred aspect, the nucleic acid probe is nucleotides 58 to 3164 of SEQ ID NO: 5. In another preferred aspect, the nucleic acid probe is a polynucleotide sequence which encodes the polypeptide of SEQ ID NO: 6, or a subsequence thereof. In another preferred aspect, the nucleic acid probe is SEQ ID NO: 5. In another preferred aspect, the nucleic acid probe is the mature polypeptide coding region of SEQ ID NO: 5. In another preferred aspect, the nucleic acid probe is the polynucleotide sequence contained in plasmid pJSF9b which is contained in E. coli NRRL B-30856, wherein the polynucleotide sequence thereof encodes a polypeptide having alpha-glucosidase activity. In another preferred aspect, the nucleic acid probe is the mature polypeptide coding region contained in plasmid pJSF9b which is contained in E. coli NRRL B-30856.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

In a third aspect, the present invention relates to isolated polypeptides having alpha-glucosidase activity having the following physicochemical properties: a pH optimum in the range of about 3.5 to about 4.5, preferably about 3.8 to about 4.5, more preferably about 4.0 to about 4.5, most preferably about 4.0 to about 4.3, and even most preferably about pH 4.1 in 50 mM acetate buffer/50 mM phosphate buffer at 37° C., a temperature optimum in the range of about 60° C. to about 63° C. in 50 mM sodium acetate pH 5.0, and thermostability up to about 67° C. to about 70° C. (approximately 80% residual activity) in 50 mM sodium acetate pH 5.0 for 5 minutes. In a preferred aspect, the isolated polypeptide having alpha-glucosidase activity has thermostability up to about 67° C. (approximately 80% residual activity) in 50 mM sodium acetate pH 5.0 for 5 minutes. In another preferred aspect, the isolated polypeptide having alpha-glucosidase activity has thermostability up to about 70° C. (approximately 80% residual activity) in 50 mM sodium acetate pH 5.0 for 5 minutes In a fourth aspect, the present invention relates to artificial variants comprising a conservative substitution, deletion, and/or insertion of one or more amino acids of SEQ ID NO: 2, SEQ ID NO: 4, or SEQ ID NO: 6; or the mature polypeptides thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethyl proline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., alpha-glucosidase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46: 145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 15 to 881 of SEQ ID NO: 2, amino acids 30 to 967 of SEQ ID NO: 4, or amino acids 20 to 988 of SEQ ID NO: 6 is 10, preferably 9, more preferably 8, more preferably 7, more preferably at most 6, more preferably at most 5, more preferably 4, even more preferably 3, most preferably 2, and even most preferably 1.

Sources of Polypeptides Having Alpha-Glucosidase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a cell in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulars, Bacillus coagulans, Bacillus lautos, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomy-* ces, *Penicillium, Piromyces, Schizophyllum, Talaromyces, Thermoascus, Thielavia, Tolypocladium*, or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having alpha-glucosidase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium tfichothecioides, Fusarium venenatum, Humicola insolens, Humicola lanuginosa, Mucor miehei, Myceliophthora thermophila, Neurospora crassa*, or *Penicillium purpurogenum, Trichoderma harzianum, Trichoderma koningii, Trichoderma longibrachiatum, Trichoderma reesei*, or *Trichoderma viride* polypeptide having alpha-glucosidase activity.

In a more preferred aspect, the polypeptide is an *Aspergillus fumigatus* polypeptide, e.g., the polypeptide of SEQ ID NO: 2, SEQ ID NO: 4, or SEQ ID NO: 6, or the mature polypeptides thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention.

In a preferred aspect, the nucleotide sequence is set forth in SEQ ID NO: 1. In another more preferred aspect, the nucleotide sequence is the sequence contained in plasmid pSMO216 which is contained in *E. coli* NRRL B-30751. In another preferred aspect, the nucleotide sequence is the mature polypeptide coding region of SEQ ID NO: 1. In another more preferred aspect, the nucleotide sequence is the mature polypeptide coding region contained in plasmid pSMO216 which is contained in *E. coli* NRRL B-30751. The present invention also encompasses nucleotide sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have alpha-glucosidase activity.

In another preferred aspect, the nucleotide sequence is set forth in SEQ ID NO: 3. In another more preferred aspect, the nucleotide sequence is the sequence contained in plasmid pHyGe011 which is contained in *E. coli* NRRL B-30750. In another preferred aspect, the nucleotide sequence is the mature polypeptide coding region of SEQ ID NO: 3. In another more preferred aspect, the nucleotide sequence is the mature polypeptide coding region contained in plasmid pHyGe011 which is contained in *E. coli* NRRL B-30750. The present invention also encompasses nucleotide sequences which encode a polypeptide having the amino acid sequence of SEQ ID NO: 4 or the mature polypeptide thereof, which differ from SEQ ID NO: 3 by virtue of the degeneracy of the genetic code. The present invention also relates to subsequences of SEQ ID NO: 3 which encode fragments of SEQ ID NO: 4 that have alpha-glucosidase activity.

In another preferred aspect, the nucleotide sequence is set forth in SEQ ID NO: 5. In another more preferred aspect, the nucleotide sequence is the sequence contained in plasmid pJSF9b which is contained in *E. coli* NRRL B-30856. In another preferred aspect, the nucleotide sequence is the mature polypeptide coding region of SEQ ID NO: 5. In another more preferred aspect, the nucleotide sequence is the mature polypeptide coding region contained in plasmid pJSF9b which is contained in *E. coli* NRRL B-30856. The present invention also encompasses nucleotide sequences which encode a polypeptide having the amino acid sequence of SEQ ID NO: 6 or the mature polypeptide thereof, which differ from SEQ ID NO: 5 by virtue of the degeneracy of the genetic code. The present invention also relates to subsequences of SEQ ID NO: 5 which encode fragments of SEQ ID NO: 6 that have alpha-glucosidase activity.

The present invention also relates to mutant polynucleotides comprising at least one mutation in the mature polypeptide coding sequence of SEQ ID NO: 1, in which the mutant nucleotide sequence encodes a polypeptide which consists of amino acids 15 to 881 of SEQ ID NO: 2.

The present invention also relates to mutant polynucleotides comprising at least one mutation in the mature polypeptide coding sequence of SEQ ID NO: 3, in which the mutant nucleotide sequence encodes a polypeptide which consists of amino acids 30 to 967 of SEQ ID NO: 4.

The present invention also relates to mutant polynucleotides comprising at least one mutation in the mature polypeptide coding sequence of SEQ ID NO: 5, in which the mutant nucleotide sequence encodes a polypeptide which consists of amino acids 20 to 988 of SEQ ID NO: 6.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a cell of *Aspergillus*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 (i.e., nucleotides 142 to 2943) of at least 75%, preferably at least 80%, more preferably at least 85%, more preferably at least 90%, even more preferably at least 95%, and most preferably at least 97% identity, which encode an active polypeptide.

The present invention also relates to polynucleotides having nucleotide sequences which have a degree of identity to the mature polypeptide coding sequence of SEQ ID NO: 3 (i.e., nucleotides 142 to 2943) of at least 75%, preferably at least 80%, more preferably at least 85%, more preferably at least 90%, even more preferably at least 95%, and most preferably at least 97% identity, which encode an active polypeptide.

The present invention also relates to polynucleotides having nucleotide sequences which have a degree of identity to the mature polypeptide coding sequence of SEQ ID NO: 5 (i.e., nucleotides 142 to 2943) of at least 85%, preferably at least 90%, more preferably at least 95%, and most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, SEQ ID NO: 3, or SEQ ID NO: 5, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. See, e.g., Ford et al., 1991, *Protein Expression and Purification* 2: 95-107 for a general description of nucleotide substitution.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for alpha-glucosidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 43 to 2643 of SEQ ID NO: 1, nucleotides 146 to 3013 of SEQ ID NO: 3, or nucleotides 58 to 3164 of SEQ ID NO: 5, (ii) the cDNA sequence contained in nucleotides 43 to 2643 of SEQ ID NO: 1, nucleotides 146 to 3013 of SEQ ID NO: 3, or nucleotides 58 to 3164 of SEQ ID NO: 5 or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) nucleotides 43 to 2643 of SEQ ID NO: 1, nucleotides 146 to 3013 of SEQ ID NO: 3, or nucleotides 58 to 3164 of SEQ ID NO: 5 (ii) the cDNA sequence contained in nucleotides 43 to 2643 of SEQ ID NO: 1, nucleotides 146 to 3013 of SEQ ID NO: 3, or nucleotides 58 to 3164 of SEQ ID NO: 5, or (iii) a complementary strand of (i) or (ii); and (b) isolating the hybridizing polynucleotide, which encodes a polypeptide having alpha-glucosidase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophllus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for Aspergillus oryzae TAKA amylase, Rhizomucor miehei aspartic proteinase, Aspergillus niger neutral alpha-amylase, Aspergillus niger acid stable alpha-amylase, Aspergillus niger or Aspergillus awamori glucoamylase (glaA), Rhizomucor miehei lipase, Aspergillus oryzae alkaline protease, Aspergillus oryzae triose phosphate isomerase, Aspergillus nidulans acetamidase, Fusarium venenatum amyloglucosidase (WO 00/56900), Fusarium venenatum Daria (WO 00/56900), Fusarium venenatum Quinn (WO 00/56900), Fusarium oxysporum trypsin-like protease (WO 96/00787), Trichoderma reesei beta-glucosidase, Trichoderma reesei cellobiohydrolase I, Trichoderma reesei endoglucanase I, Trichoderma reesei endoglucanase II, Trichoderma reesei endoglucanase III, Trichoderma reesei endoglucanase IV, Trichoderma reesei endoglucanase V, Trichoderma reesei xylanase I, Trichoderma reesei xylanase II, Trichoderma reesei beta-xylosidase, as well as the NA2-tpi promoter (a hybrid of the promoters from the genes for Aspergillus niger neutral alpha-amylase and Aspergillus oryzae triose phosphate isomerase); and mutant, truncated, and hybrid promoters thereof.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1,ADH2/GAP), Saccharomyces cerevisiae triose phosphate isomerase (TPI), Saccharomyces cerevisiae metallothionine (CUP1), and Saccharomyces cerevisiae 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for Aspergillus oryzae TAKA amylase, Aspergillus niger glucoamylase, Aspergillus nidulans anthranilate synthase, Aspergillus niger alpha-glucosidase, and Fusarium oxysporum trypsin-like protease.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for Aspergillus oryzae TAKA amylase, Aspergillus niger glucoamylase, Aspergillus nidulans anthranilate synthase, Fusarium oxysporum trypsin-like protease, and Aspergillus niger alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, Bacillus stearothermophilus alpha-amylase, Bacillus licheniformis subtilisin, Bacillus licheniformis beta-lactamase, Bacillus stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred aspect, the signal peptide coding region is nucleotides 1 to 42 of SEQ ID NO: 1 which encode amino acids 1 to 14 of SEQ ID NO: 2.

In another preferred aspect, the signal peptide coding region is nucleotides 1 to 145 of SEQ ID NO: 3 which encode amino acids 1 to 29 of SEQ ID NO: 4.

In another preferred aspect, the signal peptide coding region is nucleotides 1 to 57 of SEQ ID NO: 5 which encode amino acids 1 to 19 of SEQ ID NO: 6.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in E. coli, and pUB110, pE194, pTA1060, and pAMIβ1 permitting replication in Bacillus.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI. (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophllus*, *Bacillus amyloliquefaciens*, *Bacillus brevis*, *Bacillus circulans*, *Bacillus clausii*, *Bacillus coagulans*, *Bacillus lautos*, *Bacillus lentus*, *Bacillus licheniformis*, *Bacillus megaterium*, *Bacillus stearothermophllus*, *Bacillus subtilis*, and *Bacillus thuringiensis*, or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophllus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, for example, Young and Spizizen, 1961, *Journal of Bacteriology* 81: 823-829, or Dubnau and Davidoff-Abelson, 1971, *Journal of Molecular Biology* 56: 209-221), electroporation (see, for example, Shigekawa and Dower, 1988, *Biotechniques* 6: 742-751), or conjugation (see, for example, Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Fllibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*,

*Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatom, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatom, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Aspergillus*, and more preferably *Aspergillus fumigatus*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 1, SEQ ID NO: 3, or SEQ ID NO: 5, wherein the mutant nucleotide sequence encodes a polypeptide which consists of amino acids 15 to 881 of SEQ ID NO: 2, amino acids 30 to 967 of SEQ ID NO: 4, or amino acids 20 to 988 of SEQ ID NO: 6, respectively, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having alpha-glucosidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica* napes, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omiruleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding a polypeptide having alpha-glucosidase activity of the present invention under conditions conducive for production of the polypeptide; and (b) recovering the polypeptide.

Removal or Reduction of Alpha-Glucosidase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred embodiment, the nucleotide sequence is disrupted with a selectable marker such as those described herein.

Alternatively, modification or inactivation of the nucleotide sequence may be performed by established anti-sense techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of alpha-glucosidase activity by fermentation of a cell which produces both a polypeptide of the present invention as well as the protein product of interest by adding an effective amount of an agent capable of inhibiting alpha-glucosidase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of alpha-glucosidase activity by cultivating the cell under conditions permitting the expression of the product, subjecting the resultant culture broth to a combined pH and temperature treatment so as to reduce the alpha-glucosidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a alpha-glucosidase inhibitor.

In accordance with this aspect of the invention, it is possible to remove at least 60%, preferably at least 75%, more preferably at least 85%, still more preferably at least 95%, and most preferably at least 99% of the alpha-glucosidase activity. Complete removal of alpha-glucosidase activity may be obtained by use of this method.

The combined pH and temperature treatment is preferably carried out at a pH in the range of 4-5 and a temperature in the range of 70-80° C. for a sufficient period of time to attain the desired effect, where typically, 30 to 60 minutes is sufficient.

The methods used for cultivation and purification of the product of interest may be performed by methods known in the art.

The methods of the present invention for producing an essentially alpha-glucosidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The alpha-glucosidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from alpha-glucosidase activity which is produced by a method of the present invention.

Compositions

The present invention also relates to compositions comprising a polypeptide of the present invention. Preferably, the compositions are enriched in such a polypeptide. The term "enriched" indicates that the alpha-glucosidase activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridiodes*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecloides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatom*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having alpha-glucosidase activity.

The polypeptides of the present invention may be used in the production of alcohol from cereal grains according to DE 2944483.

The polypeptides of the present invention may also be used to produce fermented malt drinks, e.g., (low-caloric) beer, according to WO 2002/55652 (published U.S. Patent Application 20040101591). Fermented malt beverages with reinforced filling taste and fullness of mouthfeel can be produced by addition of a polypeptide having alpha-glucosidase activity prior to heat treatment in a wort production process in the course of manufacturing fermented malt beverages. Low-calorie beers can be manufactured in which a polypeptide having alpha-glucosidase activity is added in the fermentation process in the brewing of beer. Production of acetic acid can be reduced by addition of a polypeptide having alpha-glucosidase activity in the fermentation process in the high gravity brewing of beer.

In manufacturing beers, starch derived from ingredients including malt is hydrolyzed by hydrolases (e.g., alpha-amylase, beta-amylase) and fermentable sugars such as glucose, maltose, and maltotriose, which a brewer's yeast can metabolize, oligosaccharides larger than maltotetraose, and dextrin are produced. The fermentable sugars are then metabolized by brewer's yeast (or other yeast) and converted to various components of beer such as alcohol. Oligosaccharides larger than maltotetraose and dextrin may remain in the beer without being metabolized and may participate in filling taste and fullness of mouthfeel of the beverages.

In a preferred aspect, the method relates to producing a fermented malt beverage, wherein a polypeptide having alpha-glucosidase activity of the present invention is added prior to heat treatment of wort in a wort production process for manufacturing a fermented malt beverage. In another more preferred aspect, the amount of the polypeptide having alpha-glucosidase activity used is 50-400 ppm per the amount of the malt. In another preferred aspect, the polypeptide having alpha-glucosidase activity is added simultaneously with ground malt. In another preferred aspect, the polypeptide having alpha-glucosidase activity is added to the mash prior to the heat treatment in the wort production process. In another preferred aspect, the polypeptide having alpha-glucosidase activity is added in the malting process. In another preferred aspect, only malt is used as an ingredient. In another preferred aspect, malt and adjuncts are used as sugar ingredients.

In another preferred aspect, the method relates to producing a beer, wherein a polypeptide having alpha-glucosidase activity of the present invention is added to the fermentation process in the brewing of the beer. In a more preferred aspect, the beer is a low-calorie beer or light beer. In another preferred aspect, the addition of the polypeptide having alpha-glucosidase activity reduces acetic acid production. In another more preferred aspect, the concentration of original extract of wort is over 10 and not more than 30 weight %.

In another more preferred aspect, the amount of the polypeptide having alpha-glucosidase activity used is 50-400 ppm per the amount of the malt.

Signal Peptide

The present invention also relates to nucleic acid constructs comprising a gene encoding a protein operably linked to a nucleotide sequence consisting of nucleotides 1 to 42 of SEQ ID NO: 1, nucleotides 1 to 145 of SEQ ID NO: 3, or nucleotides 1 to 57 of SEQ ID NO: 5 encoding a signal peptide consisting of amino acids 1 to 14 of SEQ ID NO: 2, amino acids 1 to 29 of SEQ ID NO: 4, or amino acids 1 to 19 of SEQ ID NO: 6, respectively, wherein the gene is foreign to the nucleotide sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Aspergillus oryzae* BECh2 strain (Δalp, Δamy, CPA-, KA-, Δnp1) was used for expression of the *Aspergillus fumigatus* alpha-glucosidases. *Aspergillus fumigatus* PaHa34 was used as the source of the alpha-glucosidases.

Media

Potato dextrose medium was composed per liter of 24 grams of potato dextrose broth.

Cove plates were composed per liter of 342.3 g of sucrose, 20 ml of Cove salt solution, 10 ml of 1 M acetamide, 10 ml of 1.5 M $CsCl_2$, and 25 g of Noble agar.

Cove salt solution was composed per liter of 26 g of KCl, 26 g of $MgSO_4.7H_2O$, 76 g of $KH_2PO_4$, and 50 ml of COVE trace metals solution.

Cove trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

MY25 medium was composed per liter of 25 g of maltodextrin, 2 g of $MgSO_4.7H_2O$, 10 g of $KH_2PO_4$, 2 g of citric acid, 2 g of $K_2SO_4$, 2 g of urea, 10 g of yeast extract, and 1.5 ml AMG trace metals solution, adjusted to pH 6.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

LB medium was composed per liter of 10 g of tryptone, 5 g of yeast extract, and 5 g of NaCl.

2×YT medium was composed per liter of 16 g of tryptone, 10 g of yeast extract, and 5 g of NaCl. 2×YT plates were composed per liter of 16 g of tryptone, 10 g of yeast extract, 5 g of NaCl and 15 g of Noble agar.

SOC medium was composed per liter of 20 g of tryptone, 5 g of yeast extract, 2 ml of 5M NaCl, and 2.5 ml of 1M KCl.

TAE buffer was composed of 40 mM Tris base, 20 mM sodium acetate, and 1 mM disodium EDTA pH 7.2.

Example 1

Identification of Alpha-glucosidase Genes in the Genomic Sequence of *Aspergillus Fumigatus*

A tfasty search (Pearson, W. R., 1999, in *Bianformatics Methods and Protocols*, S. Misener and S. A. Krawetz, ed., pp. 185-219) of the *Aspergillus fumigatus* partial genome sequence (The Institute for Genomic Research, Rockville, Md.) was carried out using as query an alpha-glucosidase protein sequence from *Aspergillus nidulans* (Accession No. Q9UV08). Several genes were identified as putative homologs based upon similarity to the query sequence at the amino acid level. Three genomic regions of approximately 3000 bp with 34.9, 51.4, and 77.5% identity to the query sequence at the amino acid level were identified.

Example 2

*Aspergillus Fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in TE (10 mM Tris-1 mM EDTA), and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase-free RNase A was added at a concentration of 20 mg/liter and the lysate was incubated at 37° C. for 30 minutes. Cellular debris was removed by centrifugation, and DNA was isolated by using Qiagen Maxi 500 columns (QIAGEN Inc., Valencia, Calif.). The columns were equilibrated in 10 ml of QBT washed with 30 ml of QC, and eluted with 15 ml of QF (all buffers from QIAGEN Inc., Valencia, Calif.). DNA was precipitated in isopropanol, washed in 70% ethanol, and recovered by centrifugation. The DNA was resuspended in TE buffer.

Example 3

Construction of pAILo1 Expression Vector

Expression vector pAILo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using Big-Dye™ terminator chemistry as described. Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor™ in vitro Site-Directed Mutagenesis Kit (Promega, Madison, Wis.) according to the manufacturer's instructions using the following primers (underlined nucleotide represents the changed base):

```
AMDS3NcoMut (2050):
                              (SEQ ID NO: 7)
5'-GTGCCCCATGATACGCCTCCGG-3'

AMDS2NcoMut (2721):
                              (SEQ ID NO: 8)
5'-GAGTCGTATTTCCAAGGCTCCTGACC-3'

AMDS1NcoMut (3396):
                              (SEQ ID NO: 9)
5'-GGAGGCCATGAAGTGGACCAACGG-3'
```

A plasmid comprising all three expected sequence changes was then submitted to site-directed mutagenesis, using a QuickChange™ Site-Directed Mutagenesis Kit (Stratagene, La Jolla, Calif.), to eliminate the Nco I restriction site at the end of the AMG terminator at position 1643. The following primers (underlined nucleotide represents the changed base) were used for mutagenesis:
Upper Primer to mutagenize the AMG terminator sequence:

```
                              (SEQ ID NO: 10)
5'-CACCGTGAAAGCCATGCTCTTTCCTTCGTGTAGAAGACCAGACAG-3'
```

Lower Primer to mutagenize the AMG terminator sequence:

```
                              (SEQ ID NO: 11)
5'-CTGGTCTTCTACACGAAGGAAAGAGCATGGCTTTCACGGTGTCTG-3'
```

The last step in the modification of pBANe6 was the addition of a new Nco I restriction site at the beginning of the polylinker using a QuickChange™ Site-Directed Mutagenesis Kit and the following primers (underlined nucleotides represent the changed bases) to yield pAILo1 (FIG. 4).
Upper Primer to mutagenize the NA2-tpi promoter:

```
                              (SEQ ID NO: 12)
5'-CTATATACACAACTGGATTTACCATGGGCCCGCGGCCGCAGATC-3'
```

Lower Primer to mutagenize the NA2-tpi promoter:

```
                              (SEQ ID NO: 13)
5'-GATCTGCGGCCGCGGGCCCATGGTAAATCCAGTTGTGTATATAG-3'
```

Example 4

Construction of pBM120a Expression Vector

Plasmid pBM120a was constructed to obtain a plasmid containing the double NA2 (NA2-NA2-tpi) promoter for driving gene expression in *Aspergillus* species, and containing the ampicillin resistance gene for selection in *E. coli*.

Primers were designed to PCR amplify the double NA2 promoter from pJaL721 (WO 03/008575). Restriction enzyme sites Sal I and Nco I (underlined) were added for cloning the double promoter into the *Aspergillus* expression plasmid pAILo1.

```
                              (SEQ ID NO: 14)
5'-GTCGACATGGTGTTTTGATCATTTTA-3'

(SEQ ID NO: 15)
5'-CCATGGCCAGTTGTGTATATAGAGGA-3'
```

The fragment of interest was amplified by PCR using the Expand High Fidelity PCR System (Roche Diagnostics, Mannheim, Germany). The PCR amplification reaction mixture contained 1 µl of 0.09 µg of pJaL721 per µl, 1 µl of each of the primers (50 pmol/µl), 5 µl of 10×PCR buffer with 15 mM MgCl$_2$, 1 µl of dNTP mix (10 mM each), 37.25 µl water, and 0.75 µl (3.5 U/µl) DNA polymerase mix. An Eppendorf Mastercycler thermocycler (Hamburg, Germany) was used to amplify the fragment with the following settings: 1 cycle at 94° C. for 2 minutes; 10 cycles each at 94° C. for 15 seconds, 55° C. for 30 seconds, 72° C. for 1.25 minutes; 15 cycles each at 94° C. for 15 seconds, 55° C. for 30 seconds, 72° C. for 1.25 minutes plus 5 second elongation at each successive cycle; 1 cycle at 72° C. for 7 minutes; and 10° C. hold. Ten microliters of this PCR reaction was mixed with 1 µl of 10×DNA loading dye (25% glycerol, 10 mM Tris pH 7.0, 10 mM EDTA, 0.025% bromophenol blue, 0.025% xylene cyanol) and run on a 1.0% (w/v) agarose gel using 40 mM Tris base-20 mM sodium acetate-1 mM disodium EDTA (TAE) buffer. The 1128 bp PCR product was observed with UV light on a Nucleotech gel visualization system (Nucleotech, San Mateo, Calif.). The PCR product was directly ligated into pPC2.1-TOPO (Invitrogen, Carlsbad, Calif.) according to the manufacturer's instructions. A 1 µl volume of fresh PCR product, 3 µl of double-distilled water, and 1 µl of the TOPO cloning vector were mixed with a pipette and incubated on the bench top for 5 minutes.

After the incubation, 2 µl of the mixture was used to transform OneShot competent *E. coli* cells (Invitrogen, Carlsbad, Calif.). A 2 µl volume of the ligation mixture was added to the *E. coli* cells and incubated on ice for 5 minutes. Subsequently, the cells were heat shocked for 30 seconds at 42° C., and then placed on ice for 2 minutes. A 250 µl volume of SOC medium was added to these cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Eight colonies that grew on the plates were picked with a sterile toothpick and grown overnight at 37° C., 250 rpm in a 15 ml Falcon tube containing 3 ml of LB medium supplemented with 100 μg of ampicillin per ml. The plasmids were isolated using a BioRobot 9600 (QIAGEN Inc., Valencia, Calif.).

Figure 5:
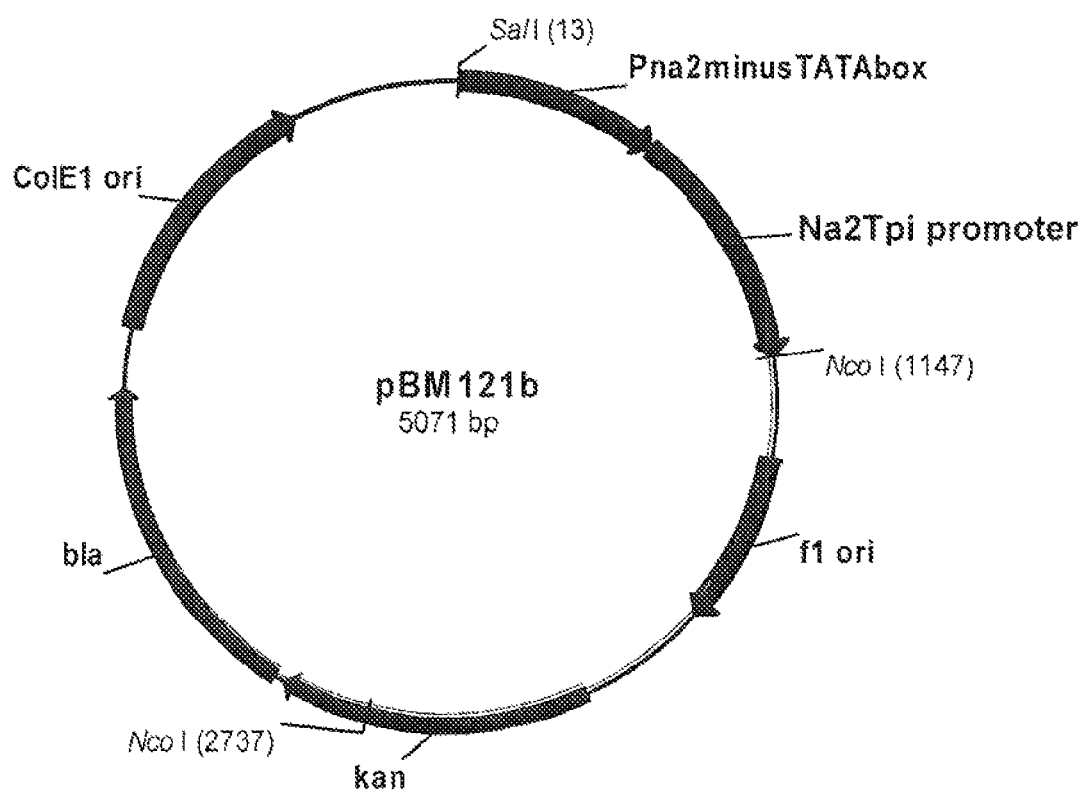
FIG. 5 shows a restriction map of pBM121b.

Four μl volumes of the resulting plasmid minipreps were digested with Eco RI. The digestion reactions were analyzed by agarose gel chromatography and UV analysis as previously described for the PCR reaction. Isolated plasmids containing an insert were sequenced using 1 μl of plasmid template, 1.6 ng M13 primer (forward or reverse) (MWG Biotech; High Point; NC), and water to 6 μl. DNA sequencing was performed with an Applied Biosystems Model 377 Sequencer XL using dye-terminator chemistry. The resulting plasmid was designated pBM121b (FIG. 5).

Figure 6:
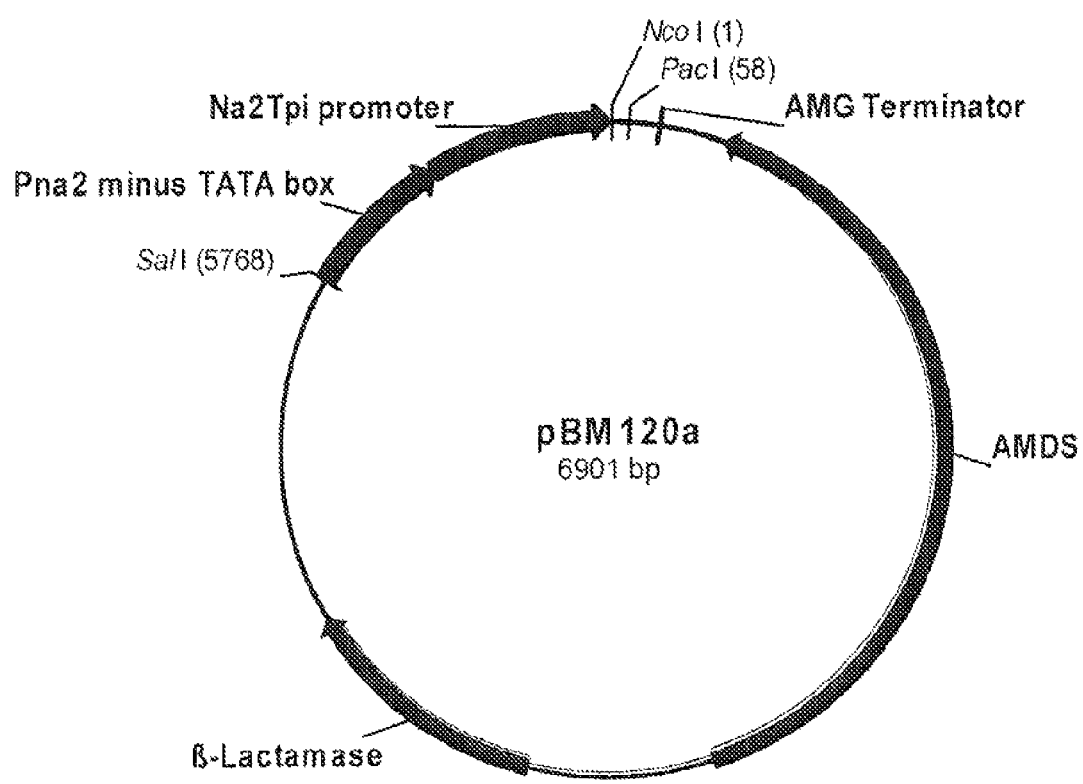

A 5 μl volume of pBM121b was digested with Sal I and Nco I. The digestion reactions were analyzed by agarose gel electrophoresis as described above, and ligated to the vector pAILo1, which had been previously cleaved with Sal I and Nco I. The resulting expression plasmid was designated pBM120a (FIG. 6).

Example 5

Cloning of an *Aspergillus Fumigatus* Alpha-glucosidase Gene Agl1

Two synthetic oligonucleotide primers shown below were designed to PCR amplify an *Aspergillus fumigatus* gene designated agl1 encoding an alpha-glucosidase gene from the genomic DNA prepared in Example 2.

```
Forward primer:
                                            (SEQ ID NO: 16)
5'-TACACAACTGGCCATGTTGAGATCGCTGC-3'

Reverse primer:
                                            (SEQ ID NO: 17)
5'-GTCACCTCTAGTTAATTAACTAGCTGAGGTCAATCTCGG-3'
```

Bold letters represent coding sequence. The remaining sequence was added for cloning sites.

The fragment of interest was amplified by PCR using the Expand High Fidelity PCR System. Fifty picomoles of each of the primers above were used in a PCR reaction containing 200 ng of *Aspergillus fumigatus* genomic DNA. The PCR amplification reaction mixture also contained 1×PCR buffer with 1.5 mM $MgCl_2$, 1 μl of dNTP mix (10 mM each), and 0.75 μl (3.5 U/μl) DNA polymerase mix (Roche Diagnostics, Mannheim, Germany) in a final volume of 50 μl. An Eppendorf Mastercycler thermocycler was used to amplify the fragment with the following settings: 1 cycle at 94° C. for 2 minutes; 10 cycles each at 94° C. for 15 seconds, 58.1° C. for 30 seconds, 72° C. for 2 minutes and 5 seconds; 15 cycles each at 94° C. for 15 seconds, 58.1° C. for 30 seconds, and 72° C. for 2 minutes and 5 seconds plus a 5 second elongation at each successive cycle; 1 cycle at 72° C. for 7 minutes; and 10° C. hold.

The reaction products were isolated on a 1.0% agarose gel using TAE buffer and an approximately 3.0 kb product band was excised from the gel and purified using a QIAquick Gel Extraction Kit (QIAGEN Inc., Valencia, Calif.) according to the manufacturer's instructions.

The fragment was then cloned into pBM120a using an InFusion Cloning Kit (BD Biosciences, Palo Alto, Calif.). The vector was digested with Nco I and Pac I. Both the digested vector and PCR fragment were purified by gel electrophoresis and QIAquick gel extraction as previously described. The gene fragment and digested vector were ligated together in a reaction resulting in the expression plasmid pSMO216mu in which transcription of the alpha-glucosidase gene was under the control of the tandem NA2-tpi promoter. The ligation reaction (20 μl) was composed of 1× InFusion Buffer (BD Biosciences, Palo Alto, Calif.), 1×BSA (BD Biosciences, Palo Alto, Calif.), 1 μl of Infusion enzyme (diluted 1:10) (BD Biosciences, Palo Alto, Calif.), 40 ng of pBM120a digested with Nco I and Pac I, and 25 ng of the *Aspergillus fumigatus* alpha-glucosidase purified PCR product. The reaction was incubated at room temperature for 30 minutes. Two μl of the reaction was used to transform *E. coli* One shot competent cells (Invitrogen Life Technologies, Carlsbad, Calif.). An *E. coli* transformant containing pSMO216mu was detected by restriction digestion and plasmid DNA was prepared using a BioRobot 9600.

Example 6

Characterization of the *Aspergillus Fumigatus* Genomic Sequence Encoding an Alpha-glucosidase Agl1 Gene DNA sequencing of the *Aspergillus fumigatus* alpha-glucosidase agl1 gene from pSMO216mu was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

Sequence analysis of pSMO216mu revealed a 1 base-pair change from the predicted sequence. Translation of the DNA sequence to protein resulted in 1 amino acid change at position 367. Site-directed mutagenesis was used to change the amino acid back to predicted sequence.

Example 7

Site-Directed Mutagenesis of the *Aspergillus Fumigatus* Alpha-glucosidase Agl1 Gene To change the amino acid mutation at position 367, synthetic oligonucleotide primers shown below were designed to PCR amplify the *Aspergillus fumigatus* alpha-glucosidase agl1 gene using a QuikChange Site-Directed Mutagenesis Kit (Stratagene, La Jolla, Calif.)

```
                                            (SEQ ID NO: 18)
5'-GCATGGAGCAGGGCATCTTCCTGCAGACTC-3'

(SEQ ID NO: 19)
5'-GAGTCTGCAGGAAGATGCCCTGCTCCATGC-3'
```

Figure 7:
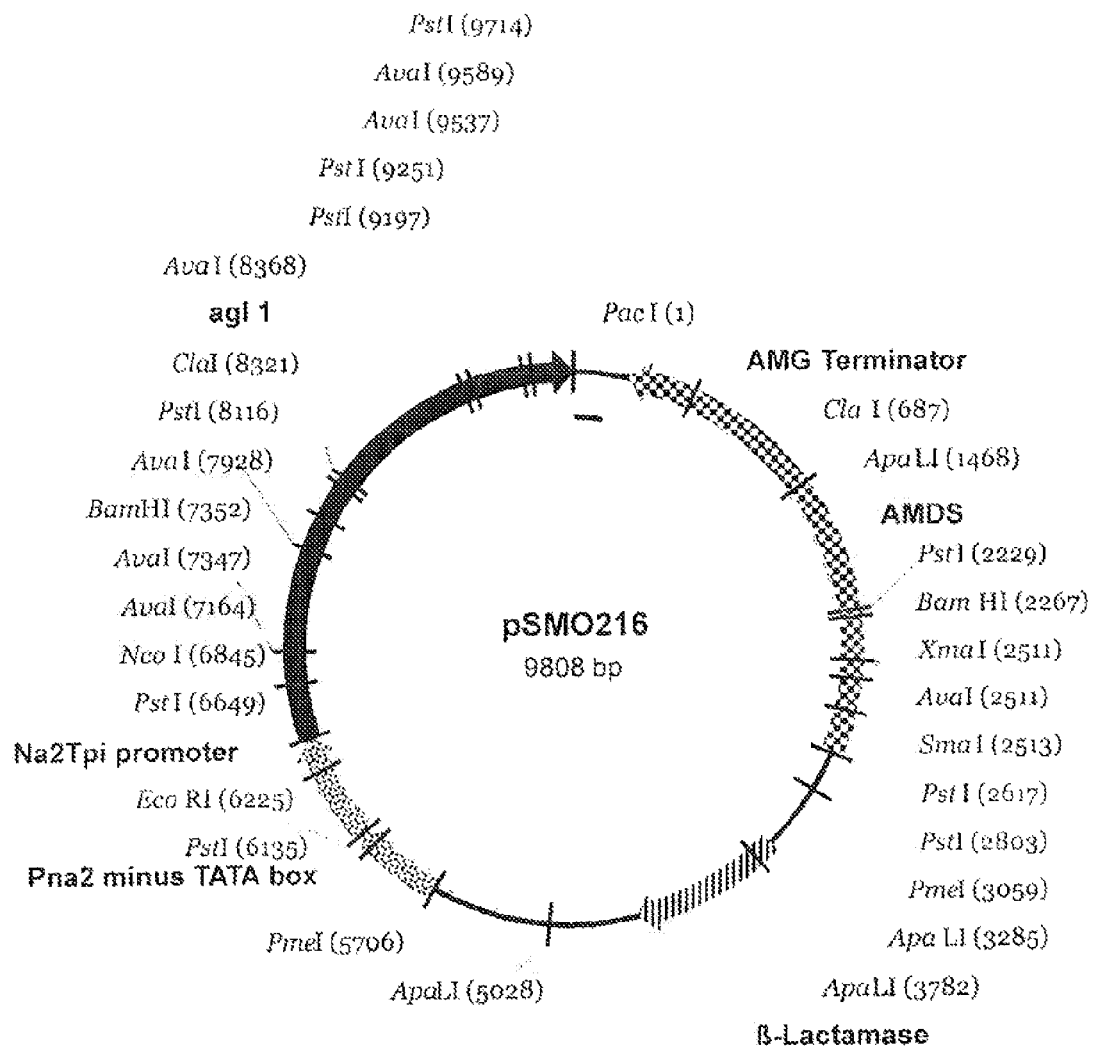
FIG. 7 shows a restriction map of pSMO216.

One hundred nanogram of each of the primers above were used in a PCR reaction containing 10 ng of pSMO216mu, 1× QuikChange reaction buffer (Stratagene, La Jolla, Calif.), 3 μl of QuikSolution (Stratagene, La Jolla, Calif.), 1 μl of 10 mM blend of dATP, dTTP, dGTP and dCTP, and 1 μl of 2.5 U/μl Pfu Ultra enzyme (Stratagene, La Jolla, Calif.), in a final volume of 50 μl. An Eppendorf Mastercycler thermocycler was used with the following settings: one cycle at 95° C. for 1 minute; 30 cycles each at 95° C. for 1 minute, 55° C. for 1 minute, and 65° C. for 14 minutes. The heat block then went to a 10° C. soak cycle. One microliter of Dpn I was directly added to the amplification reaction and incubated at 37° C. for 1 hour. A 2 μl volume of the Dpn I digested reaction was used to transform *E. coli* X10-Gold Ultracompetent Cells (Stratagene, La Jolla, Calif.). An *E. coli* transformant containing the plasmid pSMO216 was detected by restriction digestion and plasmid DNA was prepared using a BioRobot 9600. Sequence analysis verified the by changes resulting in plasmid pSMO216 (FIG. 7).

*E. coli* XL10-Gold Ultracompetent cells containing pSMO216 were deposited with the Agricultural Research Service Patent Culture Collection, Northern Regional Research Center, 1815 University Street, Peoria, Ill., 61604, as NRRL B-30751, with a deposit date of Jun. 17, 2004.

Gene models for the sequences were constructed based on the tfasty output and alignment with homologous genes from *Aspergillus oryzae*. The nucleotide sequence (SEQ ID NO: 1) and deduced amino acid sequence (SEQ ID NO: 2) are shown in FIGS. 1A-1E. The genomic fragment encodes a polypeptide of 881 amino acids, interrupted by 6 introns of 49 bp (nucleotides 211 to 260), 52 bp (nucleotides 820 to 872), 54 bp (nucleotides 1063 to 1117), 51 bp (nucleotides 1135 to 1186), 49 bp (nucleotides 1592 to 1643), and 51 bp (nucleotides 1702 to 1753). The % G+C content of the agl1 gene is 57.4%. Using the SignalP software program (Nielsen et al., 1997, *Protein Engineering* 10:1-6), a signal peptide of 14 residues was predicted. The predicted mature protein contains 867 amino acids with a molecular mass of 98.8 kDa.

A comparative alignment of alpha-glucosidase sequences was determined using the Clustal W method (Higgins, 1989, *CABIOS* 5: 151-153) using the LASERGENE™ MEGA-LIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* alpha-glucosidase (Agl1) shares 67% identity to the deduced amino acid sequence of the *Aspergillus nidulans* alpha-glucosidase (EMBL AB057788).

Example 8

Expression of the *Aspergillus Fumigatus* Alpha-glucosidase Agl1 Gene in *Aspergillus Oryzae* BECh2

*Aspergillus oryzae* BECh2 protoplasts were prepared according to the method of Christensen et al., 1988, *Bio/Technology* 6: 1419-1422. A total of 5 μg of pSMO216 was used to transform *Aspergillus oryzae* BECh2.

The transformation of *Aspergillus oryzae* BECh2 with pSMO216 yielded 20 transformants. The 20 transformants were transferred to individual Cove plates. Spores of the transformants were collected in 4 ml of 0.01% Tween 20 and 200 μl of the spore suspension was inoculated separately into 25 ml of MY25 medium in 125 ml plastic shake flasks and incubated at 34° C., 250 rpm. Three and five days after inoculation, culture supernatants were assayed for alpha-glucosidase activity as described below.

Culture supernatants of 100 μl were diluted in 0.1 M sodium acetate buffer pH 4.3. An AMG standard obtained from Novozymes A/S, Bagsærd, Denmark, was diluted using 2-fold steps starting with a 0.033 AGU/ml concentration and ending with a 0.0042 AGU/ml concentration in 0.1 M sodium acetate buffer pH 4.3. One hundred micro-liters of a 20 mg/ml maltose solution was added to each well then incubated at 25° C. for 180 minutes. Upon completion of the incubation step 200 μl of a 0.06 N NaOH solution was added to each well to quench the reaction. A total of 30 μl of the quenched reaction was transferred from each well and placed into a new 96-well plate followed by the addition of 200 μl of liquid glucose (oxidase) reagent (Pointe Scientific, Inc, Lincoln Park, Mich., USA) to each well and incubated at room temperature for 18 minutes. Upon completion of the incubation, the absorbance at 505 nm was measured for the 96-well plate using a Spectra Max 349 (Molecular Devices, Sunnyvale, Calif.). Sample concentrations were determined by extrapolation from the generated standard curve. The glucose content present in the medium was normalized by independently measuring glucose in the sample broth by the Liquid Glucose Reagent without addition of maltose. The absorbance was subtracted from the value from reagents in which maltose substrate was added.

The results of the assays demonstrated that about half of the transformants expressed alpha-glucosidase activity. One transformant designated *Aspergillus oryzae* SMO17 was cultivated as described above in MY25 medium to supply enzyme for purification and characterization.

Example 9

Cloning of an *Aspergillus Fumigatus* Alpha-glucosidase Agl2 Gene

Two synthetic oligonucleotide primers shown below were designed to PCR amplify an *Aspergillus fumigatus* gene designated agl2 encoding an alpha-glucosidase from the genomic DNA prepared in Example 2.

```
Forward primer:
                                        (SEQ ID NO: 20)
5'-ACACAACTGGCCATGGCCCGGAGCAGCTCGTC-3'

Reverse primer:
                                        (SEQ ID NO: 21)
5'-AGTCACCTCTAGTTAATTAATTAGAATTCAATCTTCCATG-3'
```

Bold letters represent coding sequence. The remaining sequence is added for cloning sites.

The fragment of interest was amplified by PCR using the Expand High Fidelity PCR System. Fifty picomoles of each of the primers above were used in a PCR reaction containing 200 ng of *Aspergillus fumigatus* genomic DNA. The PCR amplification reaction mixture also contained 1×PCR buffer with 1.5 mM $MgCl_2$, 1 μl of dNTP mix (10 mM each), and 0.75 μl (3.5 U/μl) DNA polymerase mix in a final volume of 50 μl. An Eppendorf Mastercycler thermocycler was used to amplify the fragment with the following settings: 1 cycle at 94° C. for 2 minutes; 10 cycles each at 94° C. for 15 seconds, 58.1° C. for 30 seconds, 72° C. for 2 minutes and 5 seconds; 15 cycles each at 94° C. for 15 seconds, 58.1° C. for 30 seconds, 72° C. for 2 minutes and 5 seconds plus 5 second elongation at each successive cycle; 1 cycle at 72° C. for 7 minutes; and 10° C. hold.

The reaction products were isolated on a 1.0% agarose gel using TAE buffer and an approximately 3.0 kb product band was excised from the gel and purified using a QIAquick Gel Extraction Kit according to the manufacturer's instructions.

The fragment was then cloned into the pCR2.1-TOPO vector (Invitrogen Life Technologies, Carlsbad, Calif.). The gene fragment was purified by a PCR Clean Up Kit (QIAGEN Inc., Valencia, Calif.). The fragment and pCR2.1-TOPO vector were ligated by using conditions specified by the manufacturer resulting in plasmid pHyGe011mu. Two μl of the reaction was used to transform *E. coli* One Shot competent cells. An *E. coli* transformant containing the plasmid pHyGe011mu was detected by restriction digestion and plasmid DNA was prepared using a BioRobot 9600.

Example 10

Characterization of the *Aspergillus Fumigatus* Genomic Sequence Encoding an Alpha-glucosidase Agl2 Gene DNA sequencing of the *Aspergillus fumigatus* alpha-glucosidase agl2 gene from pHyGe011mu was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, Journal of Virology Methods 38: 47-60) and primer walking strategy. Nucleotide sequence data were scrutinized for quality and all sequences were compared to each other with assistance of PHRED/PHRAP software (University of Washington, Seattle, Wash.).

Sequence analysis of pHyGe011mu revealed 7 base-pair changes from the predicted sequence. Translation of the DNA sequence to protein resulted in 3 amino acid changes at positions 140, 530 and 941. Site-directed mutagenesis was used to change the three amino acids back to predicted sequence.

Example 11

Site-Directed Mutagenesis of the *Aspergillus Fumigatus* Alpha-glucosidase Agl2 Gene To change the three amino acid mutations at positions 140, 530 and 941, three synthetic oligonucleotide primers shown below were designed to PCR amplify the *Aspergillus fumigatus* alpha-glucosidase agl2 gene containing five base pair changes using a QuikChange Site-Directed Mutagenesis Kit.

```
                                              (SEQ ID NO: 22)
5'-CGCGCAGCTCCAGACTCCAGGAAAGAAATCAC-3'

(SEQ ID NO: 23)
5'-GTACTTGAACAAGCCGGTCCACCATTTGATTG-3'

(SEQ ID NO: 24)
5'-GCCTGCCTGCTGGGCGTGATACTCCAAGGGTG-3'
```

Figure 8:
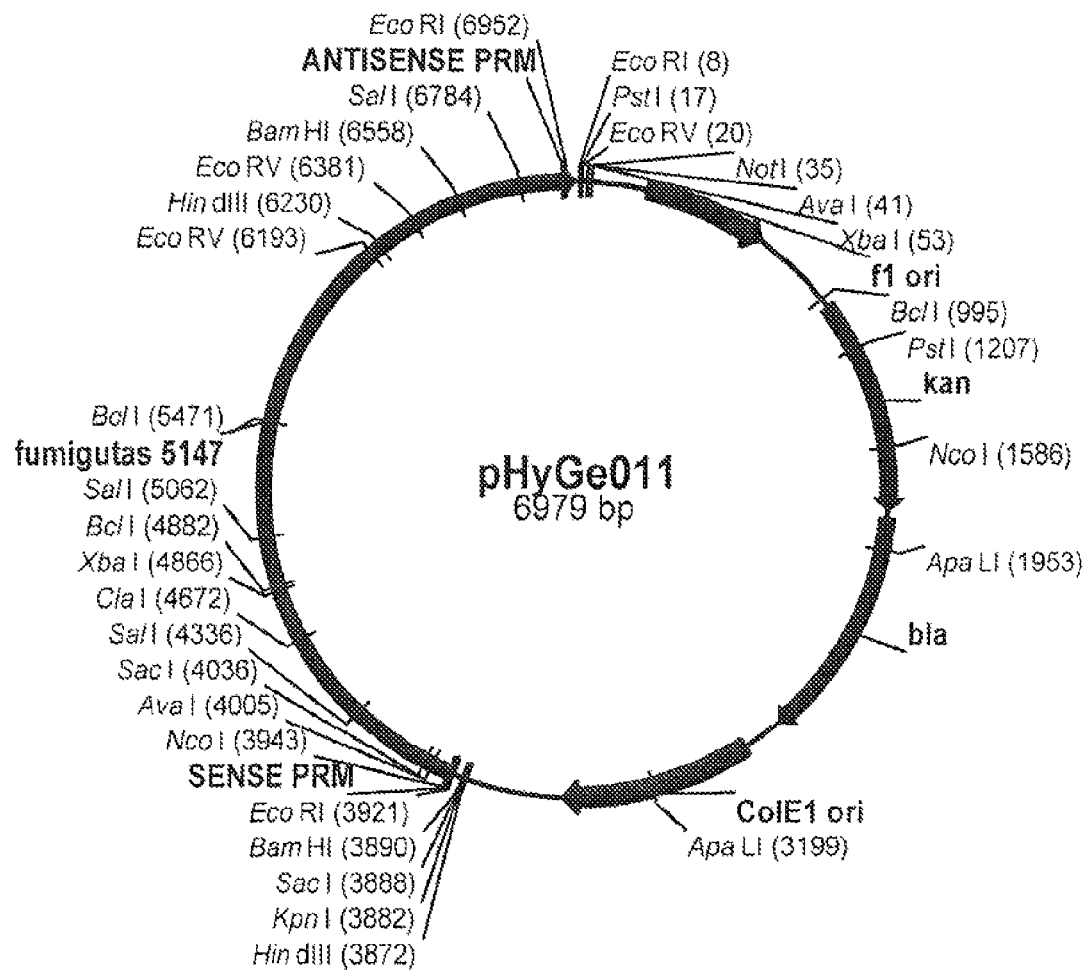
FIG. 8 shows a restriction map of pHyGe011.

One hundred nanogram of each of the primers above were used in a PCR reaction containing 100 ng of pHyGe011mu, 1× QuikChange reaction buffer, 0.75 µl of QuikSolution, 1 µl of 10 mM blend of dATP, dTTP, dGTP and dCTP, 1 µl of QuikChange Multi enzyme blend, in a final volume of 50 µl. An Eppendorf Mastercycler thermocycler was used with the following settings: one cycle at 95° C. for 1 minute; 30 cycles each at 95° C. for 1 minute, 55° C. for 1 minute, and 65° C. for 14 minutes. The heat block then went to a 10° C. soak cycle. One microliter of Dpn I was directly added to the amplification reaction and incubated at 37° C. for 1 hour. A 2 µl volume of the Dpn I digested reaction was used to transform to *E. coli* XL10-Gold Ultracompetent Cells. An *E. coli* transformant containing the plasmid pHyGe011 was detected by restriction digestion and plasmid DNA was prepared using a BioRobot 9600. Sequence analysis verified the by changes resulting in plasmid pHyGe011 (FIG. 8).

*E. coli* XL10-Gold containing plasmid pHyGe011 was deposited with the Agricultural Research Service Patent Culture Collection, Northern Regional Research Center, 1815 University Street, Peoria, Ill., 61604, as NRRL B-30750, with a deposit date of Jun. 10, 2004.

Gene models for the sequences were constructed based on the tfasty output and alignment with homologous genes from *Aspergillus oryzae*. The nucleotide sequence (SEQ ID NO: 3) and deduced amino acid sequence (SEQ ID NO: 4) are shown in FIGS. 2A-2C. The genomic fragment encodes a polypeptide of 967 amino acids, interrupted by 2 introns of 58 (nucleotides 85 to 142) and 54 bp (nucleotides 899 to 952). The % G+C content of the gene is 51.2%. Using the SignalP software program (Nielsen et al., 1997, *Protein Engineering* 10:1-6), a signal peptide of 29 residues was predicted. The predicted mature protein contains 938 amino acids with a molecular mass of 106.5 kDa.

A comparative alignment of alpha-glucosidase sequences was determined using the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* alpha-glucosidase (Agl2) shared 71% identity to the deduced amino acid sequences of a putative alpha-glucosidase from *Neurospora crassa* (accession number SWALL Q8NIY3).

Example 12

Construction of an *Aspergillus Oryzae* Expression Vector for the *Aspergillus Fumigatus* Alpha-glucosidase Agl2 Gene The *Aspergillus fumigatus* alpha-glucosidase agl2 gene was cloned into the expression vector pBM120a. The gene fragment was released from pHyGe011 by digestion with Nco I and Pac I and then purified by gel electrophoresis and Qiaquick gel purification as previously described. The pBM120a vector was digested with Nco I and Pac I. The gene fragment and the digested vector were ligated together using a Rapid DNA Ligation Kit (Boehringer Mannheim, Germany) resulting in expression plasmid pHyGe002 in which transcription of the *Aspergillus fumigatus* alpha-glucosidase gene was under the control of the tandem NA2-tpi promoter. Five microliter of the reaction was used to transform *E. coli* XL1-Blue Subcloning-Grade Competent Cells (Stratagene, La Jolla, Calif.). An *E. coli* transformant containing the pHyGe002 plasmid was detected by restriction digestion and plasmid DNA was prepared using a BioRobot 9600.

Example 13

Expression of the *Aspergillus Fumigatus* Alpha-glucosidase Agl2 Gene in *Aspergillus Oryzae* BECh2

*Aspergillus oryzae* BECh2 protoplasts were prepared according to the method of Christensen et al., 1988, supra. A total of 7.3 µg of pHyGe002 was used to transform *Aspergillus oryzae* BECh2.

The transformation of *Aspergillus oryzae* BECh2 with pHyGe002 yielded 24 transformants. The 24 transformants were transferred to individual Cove plates. Spores of the 24 transformants were collected in 4 ml of 0.01% Tween 20 and 200 µl of the spore suspension was inoculated separately into 25 ml of MY25 medium in 125 ml plastic shake flasks and incubated at 34° C., 250 rpm. Three and five days after inoculation, culture supernatants were assayed for alpha-glucosidase activity as described in Example 8.

The results of the assays demonstrated that about half of the transformants expressed alpha-glucosidase activity.

Example 14

Cloning of an *Aspergillus Fumigatus* Alpha-glucosidase Agl3 Gene

Two synthetic oligonucleotide primers shown below were designed to PCR amplify an *Aspergillus fumigatus* gene designated agl3 encoding an alpha-glucosidase from the genomic DNA prepared in Example 2.

```
Forward primer:
                                     (SEQ ID NO: 25)
5'-TACACAACTGGCCATGGCCAGCGTCCTGGGCCTCGTCGC-3'

Reverse primer:
                                     (SEQ ID NO: 26)
5'-GTCACCTCTAGTTAATTAACTACCATTTCAGAATCCAGTGTCC-3'
```

Bold letters represent coding sequence. The remaining sequence was added for cloning sites.

The fragment of interest was amplified by PCR using the Expand High Fidelity PCR System. Fifty picomoles of each of the primers above were used in a PCR reaction containing 200 ng of *Aspergillus fumigatus* genomic DNA. The PCR amplification reaction mixture also contained 1×PCR buffer with 1.5 mM $MgCl_2$, 1 µl of dNTP mix (10 mM each), and 0.75 µl (3.5 U/µl) DNA polymerase mix (Roche Diagnostics, Mannheim, Germany) in a final volume of 50 µl. An Eppendorf Mastercycler thermocycler was used to amplify the fragment with the following settings: 1 cycle at 94° C. for 2 minutes; 10 cycles each at 94° C. for 15 seconds, 60° C. for 30 seconds, 72° C. for 2 minutes and 30 seconds; 20 cycles each at 94° C. for 15 seconds, 60° C. for 30 seconds, and 72° C. for 2 minutes and 30 seconds plus a 5 second elongation at each successive cycle; 1 cycle at 72° C. for 7 minutes; and 10° C. hold.

The reaction products were isolated on a 1.0% agarose gel using TAE buffer and an approximately 3.15 kb product band was excised from the gel and purified using a QIAquick Gel Extraction Kit according to the manufacturer's instructions.

Figure 9:
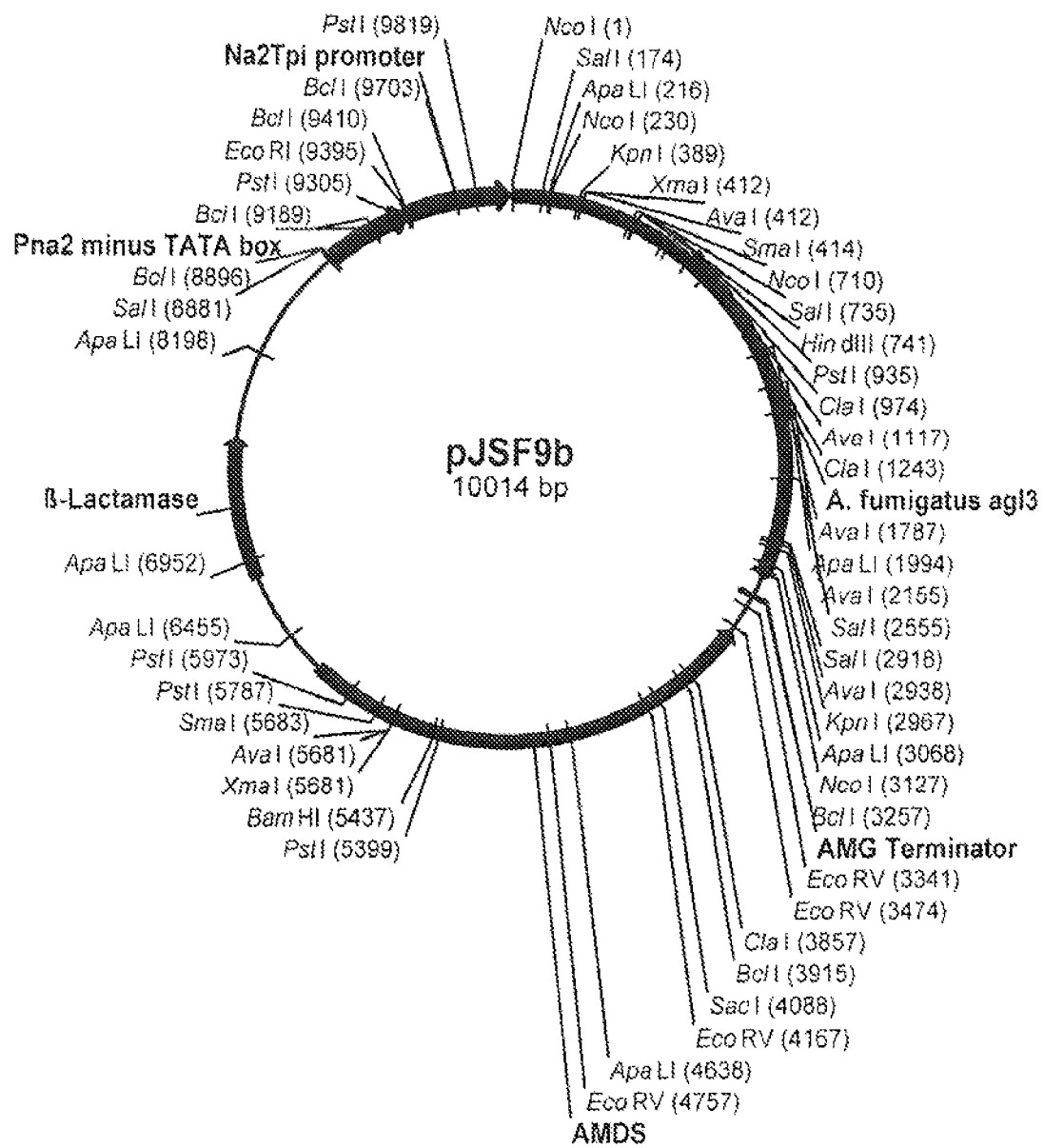
FIG. 9 shows a restriction map of pJSF9b.

The fragment was then cloned into pBM120a using an InFusion Cloning Kit. The vector was digested with Nco I and Pac I. Both the digested vector and PCR fragment were purified by gel electrophoresis and QIAquick gel extraction as previously described. The gene fragment and digested vector were ligated together in a reaction resulting in the expression plasmid pJSF9b (FIG. 9) in which transcription of the alpha-glucosidase gene was under the control of the tandem NA2-tpi promoter. The ligation reaction (20 µl) was composed of 1× InFusion Buffer, 1×BSA (BD Biosciences, Palo Alto, Calif.), 1 µl of Infusion enzyme (diluted 1:10), 90 ng of pBM120a digested with Nco I and Pac I, and 84 ng of the *Aspergillus fumigatus* alpha-glucosidase purified PCR product. The reaction was incubated at room temperature for 30 minutes. One and a half µl of the reaction was used to transform *E. coli* Solopac Gold supercompetent cells (Stratagene, La Jolla, Calif.) according to the manufacturer's instructions. An *E. coli* transformant containing pJSF9b was detected by restriction digestion and plasmid DNA was prepared using a BioRobot 9600.

Example 15

Characterization of the *Aspergillus Fumigatus* Genomic Sequence Encoding an Alpha-glucosidase Agl3 Gene DNA sequencing of the *Aspergillus fumigatus* alpha-glucosidase agl3 gene from pJSF9b was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.). Sequence analysis of pJSF9b confirmed the clone contained an alpha-glucosidase.

*E. coli* XL10-Gold containing plasmid pJSF9b was deposited with the Agricultural Research Service Patent Culture Collection, Northern Regional Research Center, 1815 University Street, Peoria, Ill., 61604, as NRRL B-30856, with a deposit date of Jun. 23, 2005.

The nucleotide sequence (SEQ ID NO: 5) and deduced amino acid sequence (SEQ ID NO: 6) are shown in FIGS. 3A-3E. The genomic fragment encodes a polypeptide of 988 amino acids, interrupted by 3 introns of 766 bp (nucleotides 700 to 765), 61 bp (nucleotides 1174 to 1235), and 70 bp (nucleotides 1407 to 1477). The % G+C content of the gene is 56.4%. Using the SignalP software program (Nielsen et al., 1997, supra), a signal peptide of 19 residues was predicted. The predicted mature protein contains 969 amino acids with a molecular mass of 108.6 kDa.

A comparative alignment of alpha-glucosidase sequences was determined using the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* alpha-glucosidase (Agl3) shares 81% identity to the deduced amino acid sequences of an alpha-glucosidase from *Aspergillus oryzae* (accession number Swissprot Q12558).

Example 16

Expression of the *Aspergillus Fumigatus* Alpha-glucosidase Agl3 Gene in *Aspergillus Oryzae* BECh2

*Aspergillus oryzae* BECh2 protoplasts were prepared according to the method of Christensen et al., 1988, supra. A total of 7.3 µg of pJSF9b was used to transform *Aspergillus oryzae* BECh2.

The transformation of *Aspergillus oryzae* BECh2 with pJSF9b yielded 20 transformants. The 20 transformants were transferred to individual Cove plates. Spores of the transformants were collected in 4 ml of 0.01% Tween 20 and 200 µl of the spore suspension was inoculated separately into 25 ml of MY25 medium in 125 ml plastic shake flasks and incubated at 34° C., 250 rpm. Three and five days after inoculation, culture supernatants were assayed for alpha-glucosidase activity as described in Example 8.

The results of the assays demonstrated that about half of the transformants expressed alpha-glucosidase activity. One transformant designated *Aspergillus oryzae* SMO24 was cultivated as described above in MY25 medium to supply enzyme for purification and characterization Example 17

Purification of *Aspergillus Fumigatus* Agl1 Alpha-glucosidase

The *Aspergillus fumigatus* Agl1 alpha-glucosidase expressed in *Aspergillus oryzae* BECH$_2$ as described in Example 8 was purified using the protocol described below.

Alpha-glucosidase activity was measured using maltose as the substrate. Maltose (1.1%; 375 µl) was incubated 5 minutes in a water bath at 37° C. An aliquot of the enzyme sample (25 µl) diluted in 50 mM sodium acetate pH 5.0 containing 0.01% Triton-X100 was mixed with the substrate. The reaction was terminated after 10 minutes incubation by adding 100 µl of 1 M Tris solution and immediate boiling for 3 minutes.

Protein concentration was determined using a BCA protein assay kit (Pierce, Rockford, Ill.) according to its "Microplate procedure".

SDS-PAGE analysis of samples from fractions and pooled fractions was performed by mixing the samples with Laemmli sample buffer (Bio-Rad, Hercules, Calif.) in a 1:1 ratio. After boiling for 2 minutes, the samples were loaded onto 8-16% SDS-PAGE gel (Bio-Rad, Hercules, Calif.) along with 10-15 µl of the molecular weight marker (Precision Plus Protein Standards, Bio-Rad, Hercules, Calif.). Gels were run in 1× Tris-Glycine-SDS running buffer (Bio-Rad, Hercules, Calif.) at 200 V for 1 hour. The gels were then rinsed 3 times with water for 5 minutes each, and stained with Bio-Safe Coomassie Stain (Bio-Rad, Hercules, Calif.) for 1 hour followed by destaining with water for more than 1 hour.

Shake flask cultures (MY25 medium) were centrifuged at 1000×g and the supernatant removed. The supernatant was filtered using a Stericup® 0.22 µm vacuum filter (Millipore, Billerica, Mass.).

The supernatant contained substantial amount of brownish pigment. To remove the pigment, 105 ml of supernatant (diluted 2.5-fold with 100 mM Tris pH 8.5) was loaded onto a 30×2.5 cm column containing Q-Sepharose Big Beads resin (Amersham Biosciences, Uppsala, Sweden) pre-equilibrated with 0.1 M Tris pH 8.5. The alpha-glucosidase was eluted with a 0.1 M sodium acetate pH 4.0 buffer wash without fractionating. The "wash-out" solution (300 ml) was collected and assayed for alpha-glucosidase activity. Fifty nine percent of the alpha-glucosidase activity was recovered. Most of the brownish pigment remained bound to the Q-Sepharose. The serine protease inhibitor, PMSF, was added at 0.5 mM to the solution after the Q-Sepharose column sodium acetate wash step in order to prevent potential proteolysis. This solution was concentrated and re-buffered (100 mM Tris pH 8.5) using a stirred 250 ml ultrafiltration cell (Amicon, Beverly, Mass.).

The alpha-glucosidase from the Q-Sepharose column step was next loaded onto a Mono Q 16/10 column (Pharmacia Biotech AB, Uppsala, Sweden) pre-equilibrated with 50 mM Tris pH 8.5. The enzyme was eluted using 0 to 0.55 M NaCl 20 column volume gradient in 50 mM Tris pH 8.5. Fractions of 10 ml were collected, assayed for alpha-glucosidase activity, and pooled based on specific activity and purity (SDS-PAGE).

The alpha-glucosidase from the Mono Q column step was finally loaded onto a Mono S 16/10 column (Pharmacia Biotech AB, Uppsala, Sweden) pre-equilibrated with 50 mM acetate, pH 4.5. The alpha-glucosidase was eluted using 0 to 0.5 M NaCl 20 column volume gradient in 50 mM acetate pH 4.5. Fractions of 10 ml were collected, assayed for alpha-glucosidase activity, and pooled based on purity (SDS-PAGE).

The purification is summarized below in Table 1.

TABLE 1

Purification of *Aspergillus fumigatus* Agl1 alpha-glucosidase

| | Volume (ml) | Fold Purification | Recovery (%) |
|---|---|---|---|
| Initial supernatant | 105 | 1 | 100 |
| Acetate wash on Q-Sepharose (pigment removal) | 35 | 3.17 | 59 |
| Mono Q column chromatography | 34 | 20.9 | 40 |
| Mono S column chromatography | 6 | 27.6 | 29 |

Example 18

Purification of *Aspergillus Fumigatus* Agl3 Alpha-glucosidase

The *Aspergillus fumigatus* Agl3 alpha-glucosidase expressed in *Aspergillus oryzae* BECH$_2$ as described in Example 16 was purified using the protocol described below.

Alpha-glucosidase activity was measured as described in Example 17. Protein concentration was determined as described in Example 17. SDS-PAGE analysis was preformed as described in Example 17.

Shake flask cultures (MY25 medium) were centrifuged at 1000×g and the supernatant removed. The supernatant was filtered using a Millipore 0.22 µm Stericup® vacuum filter.

The supernatant contained substantial amount of brownish pigment. To remove the pigment, 250 ml of supernatant (diluted 2.5-fold with 100 mM Tris pH 8.5) was loaded onto a 30×2.5 cm column containing Q-Sepharose Big Beads resin pre-equilibrated with 0.1 M Tris pH 8.5. The alpha-glucosidase was eluted with a 0.1 M sodium acetate pH 4.0 buffer wash without fractionating. The "wash-out" solution (300 ml) was collected and assayed for alpha-glucosidase activity. Sixty-eight percent of the alpha-glucosidase activity was recovered. Most of the brownish pigment remained bound to the Q-Sepharose. The serine protease inhibitor, PMSF, was added at 0.5 mM to the solution after the Q-Sepharose column sodium acetate wash step in order to prevent potential proteolysis. This solution was concentrated and re-buffered (100 mM Tris pH 8.5) using a stirred 250 ml Amicon ultrafiltration cell.

The alpha-glucosidase from the Q-Sepharose column step was next loaded onto a Mono Q 16/10 column pre-equilibrated with 50 mM Tris pH 8.5. The enzyme was eluted using a 0 to 0.5 M NaCl 20 column volume gradient in 50 mM Tris pH 8.5. Fractions of 10 ml were collected, assayed for alpha-glucosidase activity, and pooled based on specific activity and purity (SDS-PAGE).

The alpha-glucosidase from the MonoQ column step was finally loaded onto a Phenyl Sepharose HR 16/10 column (Pharmacia Biotech AB, Uppsala, Sweden) pre-equilibrated with 1.7 M (NH$_4$)$_2$SO$_4$-50 mM Tris pH 8.5. The alpha-glucosidase was eluted with a 20 column volume gradient from 1.7 M (NH$_4$)$_2$SO$_4$-50 mM Tris pH 8.5 to 50 mM Tris pH 8.5. Fractions of 10 ml were collected, assayed for alpha-glucosidase activity, and pooled based on purity (SDS-PAGE).

The purification is summarized below in Table 2.

TABLE 2

Purification of *Aspergillus fumigatus* Agl3 alpha-glucosidase

|  | Volume (ml) | Fold Purification | Recovery (%) |
| --- | --- | --- | --- |
| Initial supernatant | 250 | 1.0 | 100 |
| Acetate wash on Q-Sepharose (pigment removal) | 75 | 4.1 | 68 |
| MonoQ column chromatography | 61 | 8.2 | 34 |
| Phenyl Superose column chromatography | 9 | 11.8 | 12 |

Example 19

Characterization of *Aspergillus Fumigatus* Alpha-glucosidases

SDS-PAGE Analysis. The purified *Aspergillus fumigatus* Agl1 and Agl3 alpha-glucosidases were analyzed by SDS-PAGE as described above. Although the predicted molecular weight of the mature Agl1 alpha-glucosidase is 98.8 kDa, the SDS-PAGE results showed two bands of approximately 40 and 60 kDa. While the predicted molecular weight of the mature Agl3 alpha-glucosidase is 108.6 kDa, the SDS-PAGE results showed one band of approximately 110 kDa.

MALDI-TOF MS Analysis. MALDI-TOF MS analysis of the 40 and 60 kDa bands showed that they were from the Agl1 alpha-glucosidase and the 110 kDa band was from the Agl3 alpha-glucosidase as described below.

A MultiPROBE® II Liquid Handeling Robot (PerkinElmer Life and Analytical Sciences, Boston, Mass.) was used to perform in-gel digestions. The 40 and 60 kDa bands observed in the purified *Aspergillus fumigatus* Agl1 and the 110 kDa band from the Agl3 alpha-glucosidase were excised from the SDS-PAGE gel. The gel bands were reduced with 50 µl of 10 mM DTT in 100 mM ammonium bicarbonate pH 8.0 for 30 minutes. Following reduction, the gel pieces were alkylated with 50 µl of 55 mM iodoacetamide in 100 mM ammonium bicarbonate pH 8.0 buffer for 20 minutes. The dried gel pieces were allowed to swell in a trypsin digestion solution composed of 6 ng of sequencing grade trypsin (Princeton Separations, Adelphia, N.J.) per µl of 50 mM ammonium bicarbonate pH 8 buffer for 30 minutes at room temperature, followed by an 8 hour digestion at 40° C. Each of the reaction steps described was followed by numerous washes and pre-washes with the appropriate solutions following the manufacturer's standard protocol. Fifty µl of acetonitrile was used to de-hydrate the gel between reactions and gel pieces were air dried between steps. Peptides were extracted twice with 1% formic acid/2% acetonitrile in HPLC grade water for 30 minutes. Peptide extraction solutions were transferred to a 96 well skirted PCR type plate (ABGene, Rochester, N.Y.) that had been cooled to 10-15° C. and covered with a 96-well plate lid (PerkinElmer Life and Analytical Sciences, Boston, Mass.) to prevent evaporation. Plates were further stored at 4° C. until mass spectrometry analysis could be performed.

The 40 and 60 kDa protein bands and the 110 kDa band were in-gel digested with trypsin as described above. Recovered peptides were analyzed by peptide mass fingerprinting analysis for protein verification. A Maldi™-LR Time of Flight mass spectrometer was used (Waters Micromass® MS Technologies, Milford, Mass.). Re-crystallized alpha-cyano-4-hydroxycinnamic acid was prepared by washing milligram amounts of the alpha-cyano-4-hydroxycinnamic acid (Sigma Chemical Co., St. Louis, Mo.) with 100% acetonitrile (E.M. Science, Gibbstown, N.J.) and mixed thoroughly and centrifuged to form a matrix pellet. The acetonitrile solution was removed and discarded. HPLC grade water (Fisher Chemicals, Fairlawn, N.J.,) was added followed by a slow addition of ammonium hydroxide (J. T. Baker, Phillipsburg, N.J.) until almost all of the pellet was dissolved. Un-dissolved pellet was discarded. Concentrated HCl water (Fisher Chemicals, Fairlawn, N.J.,) was slowly added to the matrix solution until a large amount of matrix had re-crystallized. The crystallized matrix was removed by filtration and washed several times with 0.1 M HCl and allowed to dry completely. The final matrix solution consisted of a 10 mg/ml solution of re-crystallized alpha-cyano-4-hydroxycinnamic acid in 50% acetonitrile/50% aqueous 0.1% TFA. One µl of the peptide extraction solution obtained from the protein in-gel digestion was mixed with 1 µl of the re-crystallized matrix solution and spot dried on a stainless steel MALDI-TOF target plate (Waters Micromass® MS Technologies, Milford, Mass.). The mass spectrometer was operated in reflectron and positive ion mode using an acceleration voltage of +15 kV, pulse voltage of 2535 volts, and reflectron voltage of 2000 volts. The data acquisition mass range was set from 640 to 3000 m/z. A lock mass calibration standard consisting of 1 µl of 200 fmols/µl of ACTH (Adenocorticotrophic Hormone Clip 18-39 MW=2,465.1989) (Sigma Chemical Co, St. Louis, Mo.) and 1 µl of re-crystallized matrix solution was used for internal standard and spotted to adjacent lock mass target well. Data acquisition was performed using a Windows NT controlled microprocessor workstation using Masslynx 4.0 mass spectrometry software (Waters Micromass® MS Technologies, Milford, Mass.). The acquired spectra were combined, smoothed, and centered, and a peak list of peptide ion masses generated. This peak list was searched against databases using ProteinLynx™ Global Server 2.05 software (Waters Micromass® MS Technologies, Milford, Mass.).

The results from the peptide mass fingerprinting analysis indicated that the 40 and 60 kDa protein band was verified as the *Aspergillus fumigatus* Agl1 alpha-glucosidase and the 110 kDa protein band was verified as the *Aspergillus fumigatus* Agl3 alpha-glucosidase.

pH Optmum. Specific activity of the purified *Aspergillus fumigatus* Agl1 and Agl3 alpha-glucosidases was measured at different pH values in 50 mM acetate buffer/50 mM phosphate buffer at 37° C. using the activity assay described above.

Figure 10:
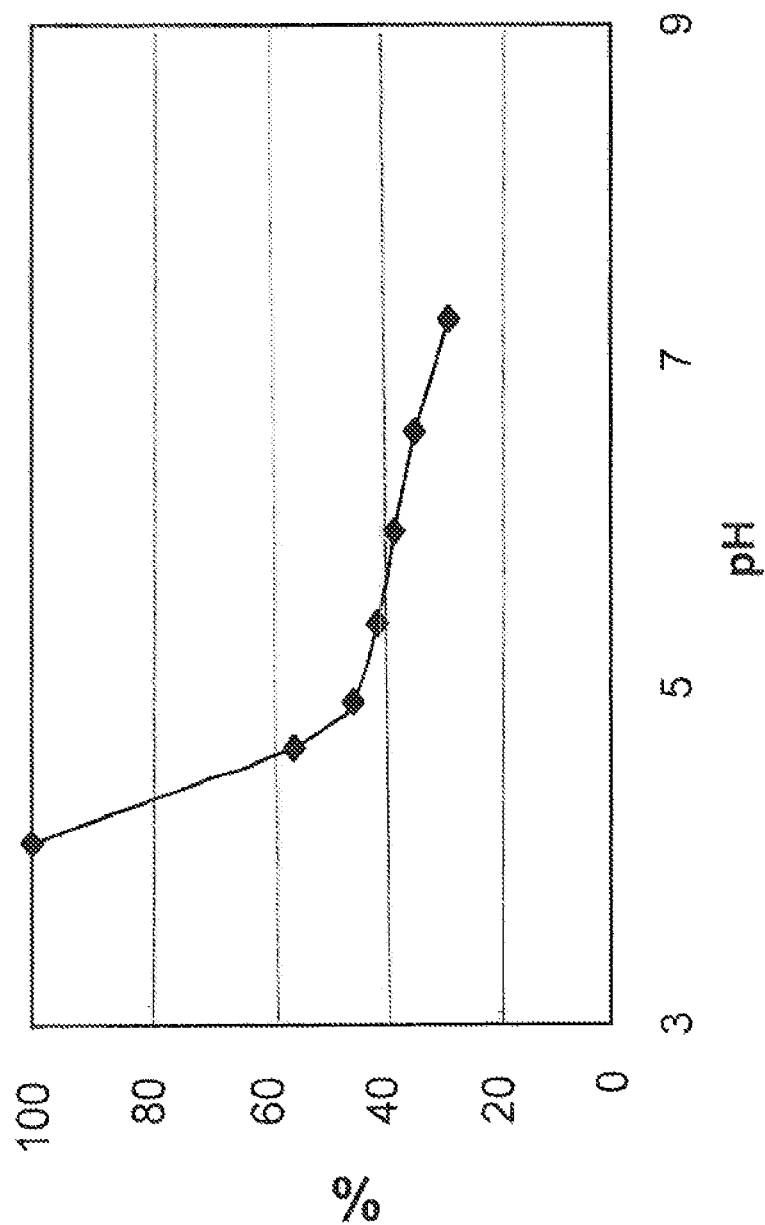
FIG. 10 shows the pH-dependence of the activity of the purified *Aspergillus fumigatus* Agl1 alpha-glucosidase in 50 mM acetate buffer/50 mM phosphate buffer at 37° C.
Figure 13:
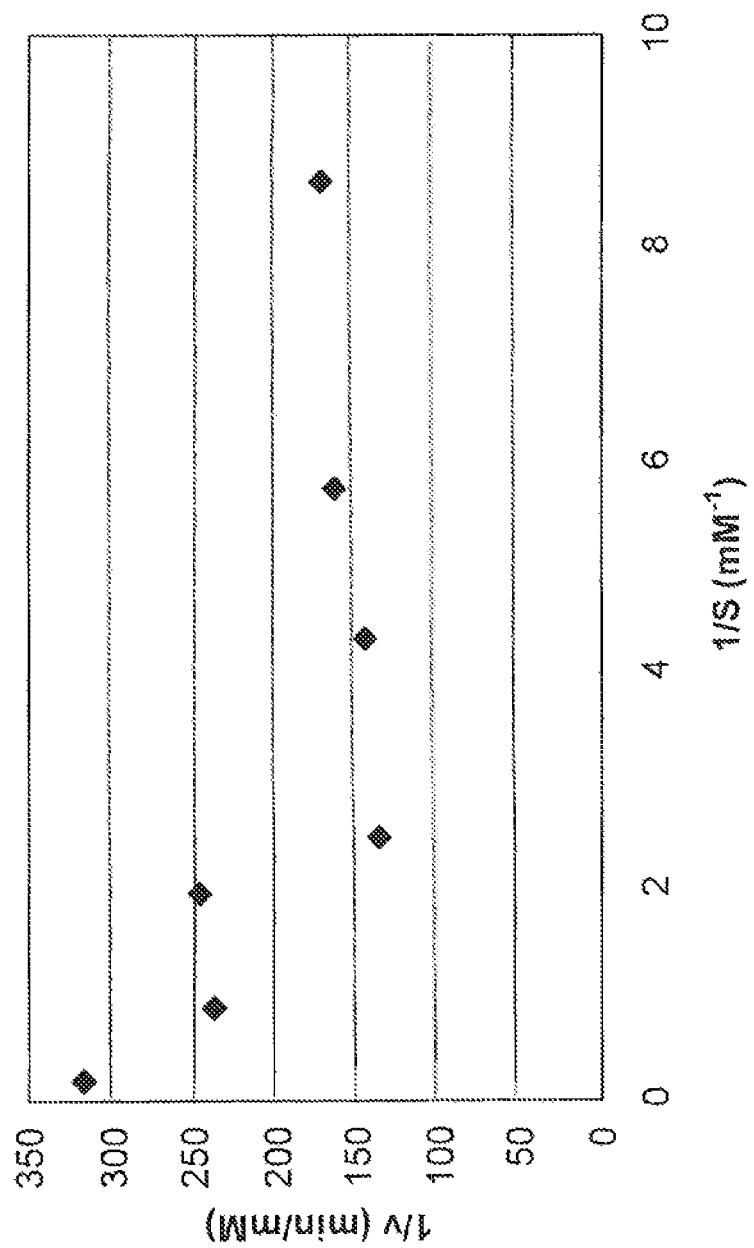
FIG. 13 shows the pH-dependence of the activity of the purified *Aspergillus fumigatus* Agl3 alpha-glucosidase in 50 mM acetate buffer/50 mM phosphate buffer at 37° C.

The Agl1 alpha-glucosidase has an acidic pH optimum of activity at pH 4.1 as shown in FIG. 10. The Agl3 alpha-glucosidase has an acidic pH optimum of activity in the range of pH 4.0-4.5 as shown in FIG. 13.

Thermostability. The thermostability of the purified *Aspergillus fumigatus* Agl1 and Agl3 alpha-glucosidases was determined by incubating each of the alpha-glucosidases in 50 mM sodium acetate pH 5.0 for 5 minutes in a water bath at a chosen temperature. Maltose as a substrate (1.1%; 375 µl) was incubated for 5 minutes in a water bath at 37° C. An aliquot of the enzyme sample was mixed with the substrate and specific activity was measured at 37° C.

Figure 11:
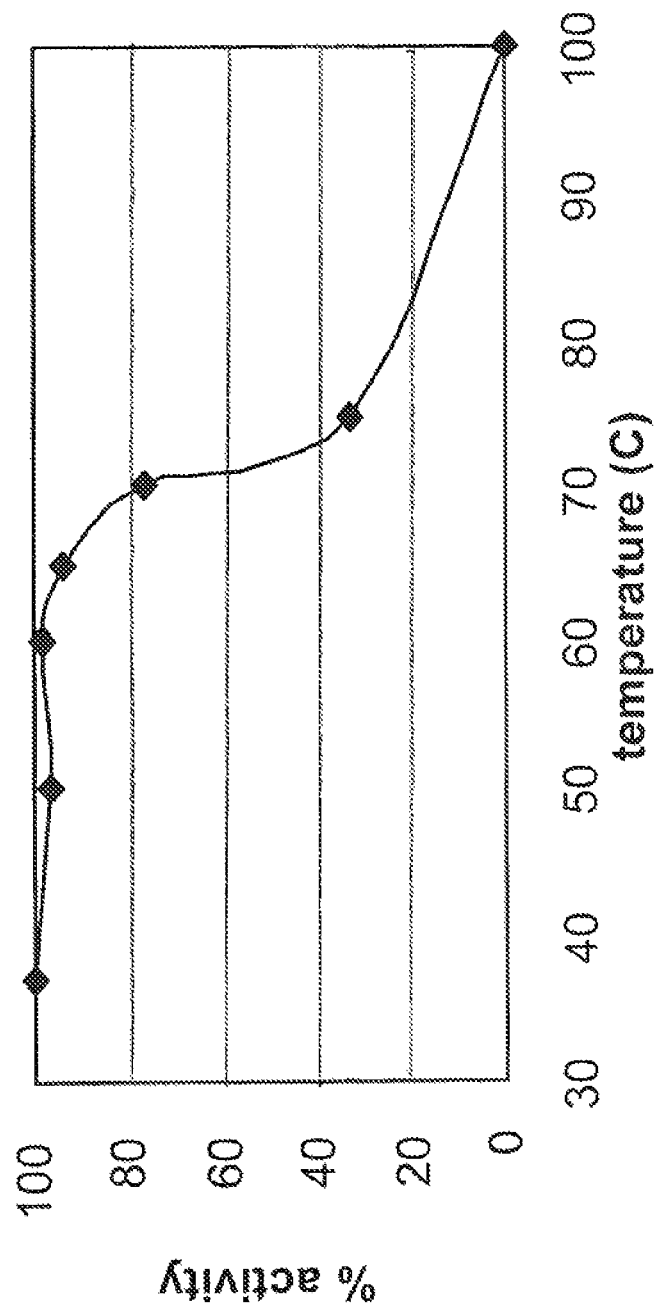
FIG. 11 shows the thermostability of the purified *Aspergillus fumigatus* Agl1 alpha-glucosidase after incubation in 0.05 M sodium acetate pH 5.0 for 5 minutes at different temperatures.

The *Aspergillus fumigatus* Agl1 alpha-glucosidase has good thermostability (approximately 80% residual) up to about 70° C. as shown in FIG. 11. The enzyme loses only 22% activity after 5 minutes in 50 mM acetate buffer pH 5.0 at this temperature and loses all activity at 100° C.

Figure 14:
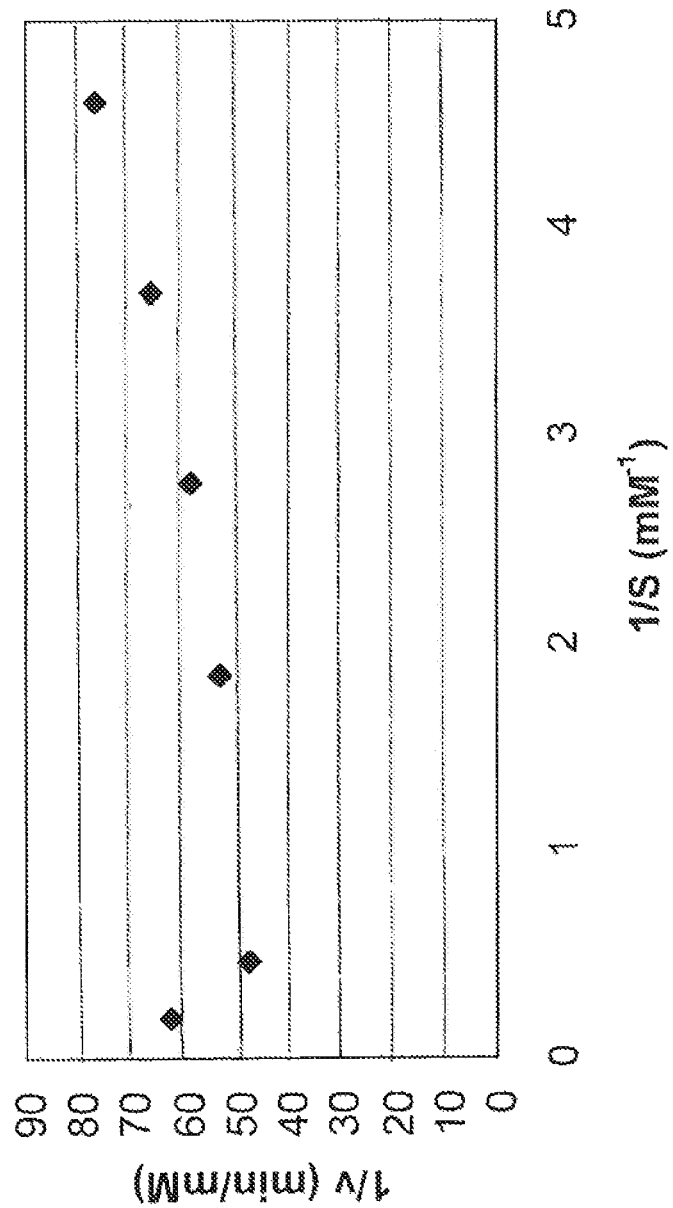
FIG. 14 shows the thermostability of the purified *Aspergillus fumigatus* Agl3 alpha-glucosidase after incubation in 50 mM sodium acetate pH 5.0 for 5 minutes at different temperatures.

The *Aspergillus fumigatus* Agl3 alpha-glucosidase has good thermostability (approximately 80% residual) up to about 67° C. as shown in FIG. 14. The enzyme loses 33% activity after 5 minutes in 50 mM acetate buffer pH 5.0 at 70° C. and loses all activity at 100° C.

Temperature Optimum. The specific activity of the purified *Aspergillus fumigatus* Agl1 and Agl3 alpha-glucosidases was measured at different temperature values in 50 mM sodium acetate pH 5.0. Maltose as a substrate (1.1%; 375 µl) was incubated 5 minutes in a water bath at a chosen temperature. An aliquot of the enzyme sample (25 µl) diluted in 50 mM sodium acetate pH 5.0 containing 0.01% Triton-X100 was mixed with the substrate. The reaction was terminated after 10 minute incubation at the same temperature by adding 1 M Tris solution (100 µl) and immediately boiling for 3 minutes.

Figure 12:
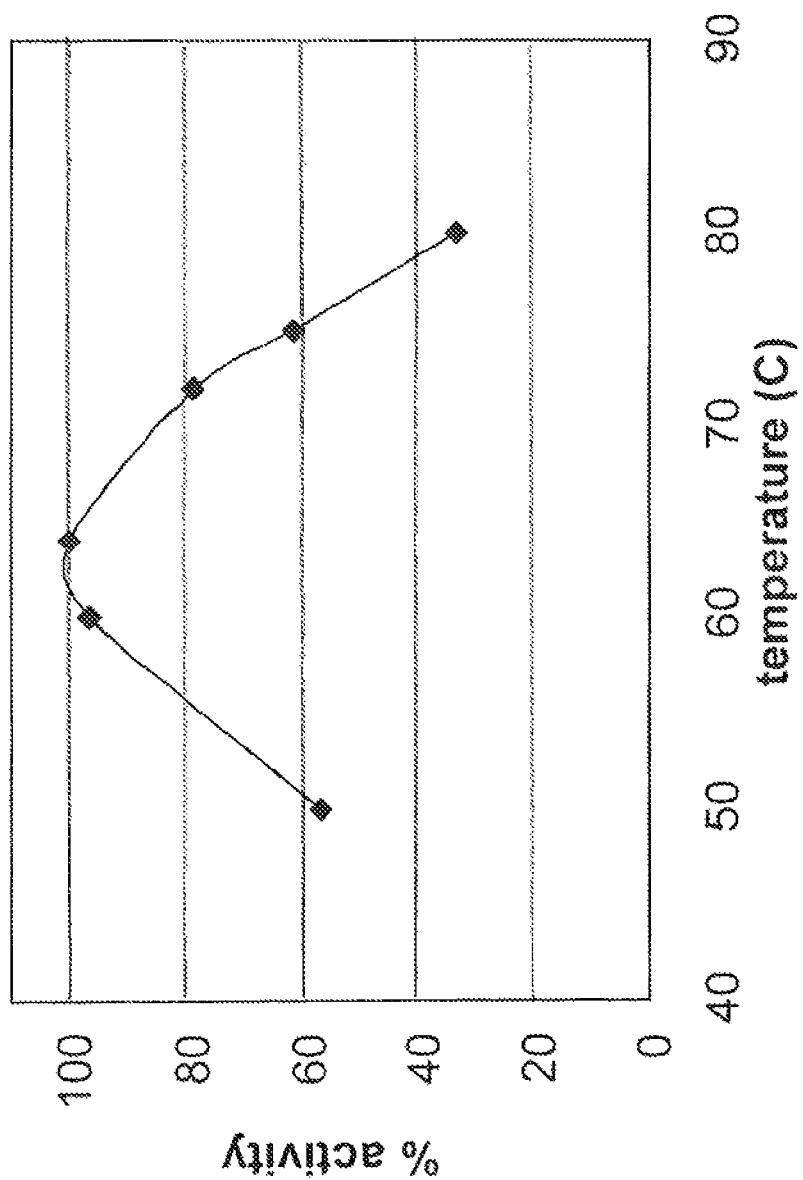
FIG. 12 shows the temperature-dependence of the activity of the purified *Aspergillus fumigatus* Agl1 alpha-glucosidase in 50 mM sodium acetate pH 5.0.
Figure 15:
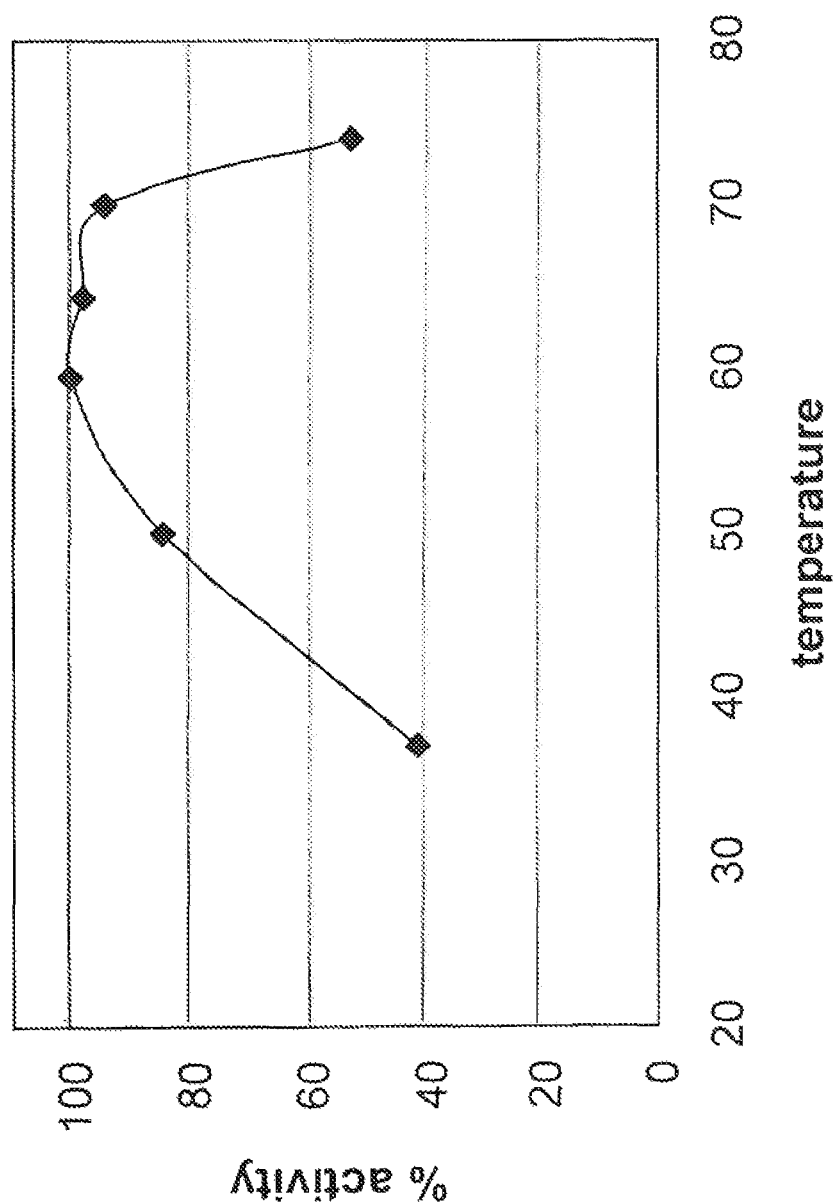
FIG. 15 shows the temperature-dependence of the activity of the purified *Aspergillus fumigatus* Agl3 alpha-glucosidase in 50 mM sodium acetate pH 5.0.

The temperature optimum for the Agl1 enzyme was around 63° C. as shown in FIG. 12. The temperature optimum for the Agl3 enzyme was around 60° C. as shown in FIG. 15.

Kinetic Parameters. The kinetic parameters for the specific hydrolysis of maltose by the purified *Aspergillus fumigatus* Agl1 and Agl3 alpha-glucosidases were determined.

A Dionex BioLC HPLC device equipped with CarboPac PA10 4×250 mm column and ED50 Electrochemical detector (Sunnyvale, Calif.) was used to detect glucose quantitatively from the hydrolysis of maltose. Sodium hydroxide solution (200 mM) was applied as a liquid phase. This method provides precise determination at the level of around 0.01 mM glucose. The calibration curve was linear between 0 mM and 1.2 mM glucose.

The incubation mixture contained 10 ml of maltose solution in the range of 0.19-4.61 mM at 37° C. The enzymatic reaction was initiated by adding 10 µl of alpha-glucosidase solution. The enzymatic reaction was terminated by placing 1 ml aliquot into boiling water for 2.5 minutes and then into ice for at least 30 minutes.

Values of $k_{cat}$ were calculated using molecular masses of 98.8 kDa and 108.6 kDa for the *Aspergillus fumigatus* alpha-glucosidases Agl1 and Agl3, respectively.

The reciprocal plots, commonly used for determining kinetic parameters, were not linear for either enzyme. At elevated maltose concentrations, the velocity of the hydrolysis reaction (accumulation of glucose) was significantly decreased. This effect was especially pronounced for the *Aspergillus fumigatus* Agl1 alpha-glucosidase where the decreased reaction velocity was observed starting from 0.58 mM maltose.

The observed decreased velocity in alpha-glucosidase-catalyzed hydrolysis of maltose may be caused by substrate inhibition (Segel, I. H. Enzyme Kinetics. Behavior and Analysis of Rapid Equilibrium and Steady-State Enzyme Systems. 1975, John Wiley & Sons), or may alternatively be the result of a competitive utilization of glucose in a transglycosylation reaction. As concentrations of maltose are increased, it becomes an acceptor for the glucose molecule. The transglycosylation reaction between the glucose and maltose leads to panose (6-O-alpha-D-glucosylmaltose). The probability of interaction between two glucose molecules, that results in maltose and isomaltose, was low due to the low concentration of maltose at the "initial rate" regime. The CarboPac PA10 column allows separation of glucose from oligosaccharides, but does not separate maltose and panose.

Kinetic parameters for the alpha-glucosidases were estimated from the plots. At pH 5.0 and 37° C., the $K_m$ for the *Aspergillus fumigatus* Agl1 alpha-glucosidase was 0.04 mM and $k_{cat}$ was 48 s$^{-1}$ (substrate interval 0.12 mM-0.41 mM). At pH 5.0 and 37° C., the $K_m$ for the *Aspergillus fumigatus* Agl3 alpha-glucosidase was 0.34 mM and the $k_{cat}$ was 237 s$^{-1}$ (substrate interval 0.14 mM-0.55 mM).

As indicated above, the substrate intervals were not always optimal. At the same time the detection limit did not allow the application of lower substrate concentrations. Both alpha-glucosidases demonstrated strong "substrate inhibition" that can likely be attributed to the transglycosylation activity.

Example 20

Purification of *Aspergillus Fumigatus* Agl2 Alpha-glucosidase

The *Aspergillus fumigatus* Agl2 alpha-glucosidase expressed in *Aspergillus oryzae* BECH$_2$ as described in Example 13 was purified using the protocol described below.

Alpha-glucosidase activity was measured as described in Example 17. Protein concentration was determined as described in Example 17. SDS-PAGE analysis was preformed as described in Example 17.

Shake flask cultures (MY25 medium) were centrifuged at 1000×g and the supernatant removed. The supernatant was filtered using a Millipore 0.22 µm Stericup® vacuum filter.

The supernatant was diluted with 100 mM Tris and the pH adjusted to 8.5. The diluted supernatant contained brownish pigment. To remove the pigment, 250 ml of supernatant (diluted 2.5-fold with 100 mM Tris pH 8.5) was loaded onto a 30×2.5 cm column (Pharmacia Biotech AB, Uppsala, Sweden) containing Q-Sepharose Big Beads resin (Amersham Biosciences, Uppsala, Sweden) pre-equilibrated with 0.1 M Tris pH 8.5. The alpha-glucosidase was eluted with a 0.1 M sodium acetate pH 4.0 buffer wash without fractionating. The "wash-out" solution (300 ml) was collected and assayed for alpha-glucosidase activity. Ninety percent of the alpha-glucosidase activity was recovered. Most of the brownish pigment remained bound to the Q-Sepharose. The serine protease inhibitor, PMSF, was added at 0.5 mM to the solution after the Q-Sepharose column sodium acetate wash step in order to prevent potential proteolysis. This solution was concentrated and re-buffered (100 mM Tris pH 8.5) using a stirred 250 ml ultrafiltration cell (Amicon, Beverly, Mass.).

The alpha-glucosidase from the Q-Sepharose column step was next loaded onto a Mono Q 16/10 column pre-equilibrated with 50 mM Tris pH 8.5. The enzyme was eluted using a 0 to 0.5 M NaCl 20 column volume gradient in 50 mM Tris pH 8.5. Fractions of 10 ml were collected, assayed for alpha-glucosidase activity, and pooled based on specific activity and purity (SDS-PAGE).

The purification is summarized below in Table 3.

TABLE 3

Purification of *Aspergillus fumigatus* Agl2 alpha-glucosidase

| | Volume (ml) | Fold purification | Recovery (%) |
|---|---|---|---|
| Initial supernatant | 1700 | 1 | 100 |
| Q-Sepharose column chromatography | 520 | 2.5 | 90 |
| Mono Q column chromatography | 90 | 6.2 | 63 |
| Precipitation | 40 | 72 | 28 |

The purified preparation gives four bands on SDS-PAGE with molecular weights of 33, 36, 75, and 105 kDa. Based on the predicted mass of the *Aspergillus fumigatus* Agl3 alpha-glucosidase, the 105 kDa band corresponds to the alpha-glucosidase.

Deposit of Biological Material

The following biological materials have been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* XL10-Gold (pSMO216) | NRRL B-30751 | Jun. 17, 2004 |
| *E. coli* XL10-Gold (pHyGe011) | NRRL B-30750 | Jun. 10, 2004 |
| *E. coli* XL10-Gold (pJSF9b) | NRRL B-30856 | Jun. 23, 2005 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A nucleic acid construct comprising a gene encoding a protein operably linked to a nucleotide sequence encoding a signal peptide selected from the group consisting of: nucleotides 1 to 42 of SEQ ID NO: 1, nucleotides 1 to 145 of SEQ ID NO: 3, and nucleotides 1 to 57 of SEQ ID NO: 5, wherein the gene is heterologous to the nucleotide sequence encoding the signal peptide.

2. A recombinant expression vector comprising the nucleic acid construct of claim 1.

3. A recombinant host cell comprising the nucleic acid construct of claim 1.

4. A method for producing a protein comprising (a) cultivating the recombinant host cell of claim 3 under conditions conducive for production of the protein; and (b) recovering the protein.

* * * * *

SEQUENCE LISTING

<160> NUMBER OF SEQ ID NOS: 26

<210> SEQ ID NO 1
<211> LENGTH: 2954
<212> TYPE: DNA
<213> ORGANISM: Aspergillus fumigatus

<400> SEQUENCE: 1

```
atgttgagat cgctgctact tcttgcgccc cttgtgggcg ctgccgtgat cggcgccagg      60
gaccacagcc aggagtgtcc tggttacaag gccaccaata ttagagaggg tcgcgattcc     120
ttaacggcgg atttgacctt ggccggtaaa ccgtgcaaca cttacggcac cgacttgaag     180
aatctgaaac tccttgttga gtaccagacc ggtacgtttt cagcgttaaa cggctatgat     240
tgtagcttac ttctttctag ataaacgcct ccatgttaag atctatgacg ccgatgagga     300
ggtttaccaa gtccccgagt cggttctccc tcgcgtggat ggcaaaggtg gatcgagcaa     360
gaagtcggcg ctcaagttcg actatcaggc gaatccgttc tctttcaagg tcaagagagg     420
cggcgaggtg ctcttcgaca cctccggttc gaatctgatc ttccagtcgc agtacctgag     480
cctccgcacc tggttgcccg aggatcctaa tctctacggt cttggcgagc acacggattc     540
tcttcgtctg gagaccacca actacacgcg tactctgtgg aaccgtgacg cgtatgctat     600
tcctgagaag accaacctgt acggcactca tcccgtgtac tatgaccacc gtggccaaca     660
cggcacccac ggtgtcttct tgctgaactc caacggcatg gacattaaga tcgacaagac     720
caaggatggc aagcagtact tagagtacaa cactctggga ggtgtctttg acttttactt     780
ctttaccggt gccacccca aggatgccag catcgagtat gcgaaagtcg tcggtcttcc     840
cgctatgcag tcctactgga cgttcggtgt acgtttccct gattcgatct gcggtccttc     900
```

```
cggctaactc ttgtcgtcta gttccaccaa tgcagatacg gctatcgtga tgtctttgag    960
gtcgccgagg ttgtctacaa ctacagccag gcgaagattc cactggagac catgtggacc   1020
gacattgact acatggacag acgtcgggtg ttcactcttg acccgagcg attcccgctc    1080
gagaagatgc gtgagttggt gtcatatctt cacaaccaca accaacacta catcgtcatg   1140
gttgacccgg ccgtcagcgt gagcggtaag tttacctttc caagtatgga ggggtgggt    1200
gcatattgac aaatgatcag acaacgttgg ctacaatgat ggcatggagc agggcatctt   1260
cctgcagact caaaacggta gcctctacaa gggtaagcct tacctaaaag tactaatgac   1320
acccagaata ttgaccctat acaggtgccg tctggcctgg tgtgactgcg tatcctgact   1380
ggttccaccc tgacatccaa aagtactgga acgaccagtt tgccaaattc ttcgacccca   1440
agaccggcgt cgacatcgac ggtctgtgga tcgatatgaa cgaggccgcc aacttctgcc   1500
cttacccttg cagtgatccc gagggctacg ctagggataa cgacctgcct cccgccgctc   1560
cccccgttcg gcccagcaac ccgcgcccgt tgcccggatt ccctggtgat tccagcccct   1620
catcctcgtc gaagcgctcc accaagggat ctaaagttgg actgcctaat cgtgacctga   1680
tcaaccctcc gtacatgatc cgtaatgaag ctggctcgct cagcaacaag accatcaaca   1740
ccgatatcat tcatgctggt gagggatatg ccgagtatga cactcacaac ctttatggta   1800
ccagtaagta ggcatccctc tgaatgacgg ggacagtcta acattcaaag tgatgagttc   1860
cgcttctcgc aatgccatgc aacaccgccg ccctggggtg cggccattgg tcatcactcg   1920
cagcacgtat gctggtgctg gcgcccacgt tggacactgg tcggtgtgca tccatctagt   1980
acctgcgaac tcttatactg acacttgaca ggctcggtga caacatctcc gagtggagca   2040
agtaccgcat ctccatctcg cagatgcttg cgtttgcctc gatgttccag gtgcctatga   2100
tcggatcaga cgtctgcggg ttcggcggca acaccaccga ggagctctgc gctcgctggg   2160
cgcgtctcgg agccttctac accttcttcc gcaaccacaa tgaaatcacc ggtatcccgc   2220
aggagttcta ccgctggccc accgttgccg agtccgctcg caaggccatc gacatccgct   2280
acaggctgct tgactacatc tacacagcct tccaccggca gacccagacc ggcgagccct   2340
tcctgcagcc catgttctac ctctatccca aggacaagga caccttcagc aaccagctgc   2400
agttcttcta cggtgacgcc atcctggtca gccctgtcac cgacgggagc cagacttcag   2460
ttgacgcata cttccccgat gatatcttct acgattggca cacgggcgcc gccctacgcg   2520
gccgcggagc caacgtcacc ctcagcaaca tcgacgtgac tgagatcccc atccacatcc   2580
gcggcggcag catcatcccc gtccggtccg agtccgccat gaccaccacc gagctgcgca   2640
agaagggctt cgagctcatc atcgccccag ggcttgatgg gactgcctcg ggcagtttgt   2700
atctcgacga cggcgactcc atcgagccgc gcgcgaccct cgagctggag ttcacgtacc   2760
gcaagggcca tctccaggtg aagggcaagt tcggtttccg cacggaggtc aagatcaacg   2820
ccgtcaccct gcttggccag tctgcgcctg cctccaagtc tgcagacgtg gcctcccttg   2880
actctggccg ccaggcagtg accatcaaga cgagcctgga tctgactggt ccttccgaga   2940
ttgacctcgg ctag                                                    2954
```

<210> SEQ ID NO 2
<211> LENGTH: 880
<212> TYPE: PRT
<213> ORGANISM: Aspergillus fumigatus

<400> SEQUENCE: 2

Met Leu Arg Ser Leu Leu Leu Leu Ala Pro Leu Val Gly Ala Ala Val

```
  1               5                    10                      15
Ile Gly Ala Arg Asp His Ser Gln Glu Cys Pro Gly Tyr Lys Ala Thr
            20                  25                  30

Asn Ile Arg Glu Gly Arg Asp Ser Leu Thr Ala Asp Leu Thr Leu Ala
            35                  40                  45

Gly Lys Pro Cys Asn Thr Tyr Gly Thr Asp Leu Lys Asn Leu Lys Leu
        50                  55                  60

Leu Val Glu Tyr Gln Thr Asp Lys Arg Leu His Val Lys Ile Tyr Asp
 65                 70                  75                  80

Ala Asp Glu Glu Val Tyr Gln Val Pro Glu Ser Val Leu Pro Arg Val
                85                  90                  95

Asp Gly Lys Gly Gly Ser Lys Lys Ser Ala Leu Lys Phe Asp Tyr
            100                 105                 110

Gln Ala Asn Pro Phe Ser Phe Lys Val Lys Arg Gly Gly Glu Val Leu
            115                 120                 125

Phe Asp Thr Ser Gly Ser Asn Leu Ile Phe Gln Ser Gln Tyr Leu Ser
        130                 135                 140

Leu Arg Thr Trp Leu Pro Glu Asp Pro Asn Leu Tyr Gly Leu Gly Glu
145                 150                 155                 160

His Thr Asp Ser Leu Arg Leu Glu Thr Thr Asn Tyr Thr Arg Thr Leu
                165                 170                 175

Trp Asn Arg Asp Ala Tyr Ala Ile Pro Glu Lys Thr Asn Leu Tyr Gly
            180                 185                 190

Thr His Pro Val Tyr Tyr Asp His Arg Gly Gln His Gly Thr His Gly
        195                 200                 205

Val Phe Leu Leu Asn Ser Asn Gly Met Asp Ile Lys Ile Asp Lys Thr
        210                 215                 220

Lys Asp Gly Lys Gln Tyr Leu Glu Tyr Asn Thr Leu Gly Gly Val Phe
225                 230                 235                 240

Asp Phe Tyr Phe Phe Thr Gly Ala Thr Pro Lys Asp Ala Ser Ile Glu
            245                 250                 255

Tyr Ala Lys Val Val Gly Leu Pro Ala Met Gln Ser Tyr Trp Thr Phe
            260                 265                 270

Gly Phe His Gln Cys Arg Tyr Gly Tyr Arg Asp Val Phe Glu Val Ala
        275                 280                 285

Glu Val Val Tyr Asn Tyr Ser Gln Ala Lys Ile Pro Leu Glu Thr Met
        290                 295                 300

Trp Thr Asp Ile Asp Tyr Met Asp Arg Arg Val Phe Thr Leu Asp
305                 310                 315                 320

Pro Glu Arg Phe Pro Leu Glu Lys Met Arg Glu Leu Val Ser Tyr Leu
            325                 330                 335

His Asn His Asn Gln His Tyr Ile Val Met Val Asp Pro Ala Val Ser
            340                 345                 350

Val Ser Asp Asn Val Gly Tyr Asn Asp Gly Met Glu Gln Gly Ile Phe
        355                 360                 365

Leu Gln Thr Gln Asn Gly Ser Leu Tyr Lys Gly Ala Val Trp Pro Gly
        370                 375                 380

Val Thr Ala Tyr Pro Asp Trp Phe His Pro Asp Ile Gln Lys Tyr Trp
385                 390                 395                 400

Asn Asp Gln Phe Ala Lys Phe Phe Asp Pro Lys Thr Gly Val Asp Ile
            405                 410                 415
```

```
Asp Gly Leu Trp Ile Asp Met Asn Glu Ala Ala Asn Phe Cys Pro Tyr
            420                 425                 430

Pro Cys Ser Asp Pro Glu Gly Tyr Ala Arg Asp Asn Leu Pro Pro
        435                 440                 445

Ala Ala Pro Pro Val Arg Pro Ser Asn Pro Arg Pro Leu Pro Gly Phe
450                 455                 460

Pro Gly Asp Phe Gln Pro Ser Ser Ser Lys Arg Ser Thr Lys Gly
465                 470                 475                 480

Ser Lys Val Gly Leu Pro Asn Arg Asp Leu Ile Asn Pro Pro Tyr Met
                485                 490                 495

Ile Arg Asn Glu Ala Gly Ser Leu Ser Asn Lys Thr Ile Asn Thr Asp
            500                 505                 510

Ile Ile His Ala Gly Glu Gly Tyr Ala Glu Tyr Asp Thr His Asn Leu
        515                 520                 525

Tyr Gly Thr Met Ser Ser Ala Ser Arg Asn Ala Met Gln His Arg Arg
530                 535                 540

Pro Gly Val Arg Pro Leu Val Ile Thr Arg Ser Thr Tyr Ala Gly Ala
545                 550                 555                 560

Gly Ala His Val Gly His Trp Leu Gly Asp Asn Ile Ser Glu Trp Ser
                565                 570                 575

Lys Tyr Arg Ile Ser Ile Ser Gln Met Leu Ala Phe Ala Ser Met Phe
            580                 585                 590

Gln Val Pro Met Ile Gly Ser Asp Val Cys Gly Phe Gly Gly Asn Thr
        595                 600                 605

Thr Glu Glu Leu Cys Ala Arg Trp Ala Arg Leu Gly Ala Phe Tyr Thr
610                 615                 620

Phe Phe Arg Asn His Asn Glu Ile Thr Gly Ile Pro Gln Glu Phe Tyr
625                 630                 635                 640

Arg Trp Pro Thr Val Ala Glu Ser Ala Arg Lys Ala Ile Asp Ile Arg
                645                 650                 655

Tyr Arg Leu Leu Asp Tyr Ile Tyr Thr Ala Phe His Arg Gln Thr Gln
            660                 665                 670

Thr Gly Glu Pro Phe Leu Gln Pro Met Phe Tyr Leu Tyr Pro Lys Asp
        675                 680                 685

Lys Asp Thr Phe Ser Asn Gln Leu Gln Phe Phe Tyr Gly Asp Ala Ile
690                 695                 700

Leu Val Ser Pro Val Thr Asp Gly Ser Gln Thr Ser Val Asp Ala Tyr
705                 710                 715                 720

Phe Pro Asp Asp Ile Phe Tyr Asp Trp His Thr Gly Ala Ala Leu Arg
                725                 730                 735

Gly Arg Gly Ala Asn Val Thr Leu Ser Asn Ile Asp Val Thr Glu Ile
            740                 745                 750

Pro Ile His Ile Arg Gly Gly Ser Ile Ile Pro Val Arg Ser Glu Ser
        755                 760                 765

Ala Met Thr Thr Thr Glu Leu Arg Lys Lys Gly Phe Glu Leu Ile Ile
770                 775                 780

Ala Pro Gly Leu Asp Gly Thr Ala Ser Gly Ser Leu Tyr Leu Asp Asp
785                 790                 795                 800

Gly Asp Ser Ile Glu Pro Arg Ala Thr Leu Glu Leu Glu Phe Thr Tyr
                805                 810                 815

Arg Lys Gly His Leu Gln Val Lys Gly Lys Phe Gly Phe Arg Thr Glu
            820                 825                 830
```

-continued

| | | | | | | | | | | |
|---|---|---|---|---|---|---|---|---|---|---|
| Val | Lys | Ile | Asn | Ala | Val | Thr | Leu | Leu | Gly | Gln | Ser | Ala | Pro | Ala | Ser |
| | | | 835 | | | | | 840 | | | | 845 | | | |

Lys Ser Ala Asp Val Ala Ser Leu Asp Ser Gly Arg Gln Ala Val Thr
    850                 855                 860

Ile Lys Thr Ser Leu Asp Leu Thr Gly Pro Ser Glu Ile Asp Leu Gly
865                 870                 875                 880

<210> SEQ ID NO 3
<211> LENGTH: 3016
<212> TYPE: DNA
<213> ORGANISM: Aspergillus fumigatus

<400> SEQUENCE: 3

```
atggcccgga gcagctcgtc tctctccaga tggacgctat tgctcgcgtt ggttgtcatt      60
ctcgggtgtc ttgttgtacc cggaggtgag ctctatgcgc tcaacttaat ccaatagtaa     120
cgccatctga ccaagtctgc cagttactgt gaagcatgag aacttcaaga aatgctctca     180
atcgggtttt tgtaagcgaa accgagcttt gcagatgacg tctccgccc aaggcgcgtc      240
ttggatttca ccatatgaac tcgatccctc ctcaattcac ttcaaagatg ccaactgca      300
agggacaatt ctcaagtcca tatctgccaa tgagaaagtc aagctgccac ttgtgatttc     360
tttcctggag tctggagctg cgcgcatcgt ggtcgacgaa gagaagcgga tgaagggcga     420
aattgacctc cgacataaca gccaagtgcg caaagagcga taatgaag cagagcaatg       480
ggcactggtt ggtggtttgg aatcgagcaa aactgccgct gtggacacag atccgagac     540
tggattcaca aagtactttt acgggccgga taacaagttt caggcaatca ttcgccatgc    600
gccgttcagc gttgattttc agcgcgatgg ccagagccat gtccgagtga atcacaaggg    660
cttcctcaac gtggaacact gcggccaaa ggtggatgtg cagagggtg acagtgttca      720
ggaaaaatcg ataccctcagc aagatgaaag cacttggtgg gaggaaactt tggtgggaa    780
caccgactcc aagccaaaag gtcccgaaag tatcggcctg gacatcacat tccctggcta    840
cagccatgtt tttgggattc agagcatgc cgactcgatg tctctgaagg aaaccaggta    900
ggtgttacat gtccctgccc ctctagagac gcaaagctga tcagtttgaa ggggcggtga    960
tggaaatcat gcggaacctt atcgcatgta caatacggac gtcttgaat atgaactcaa    1020
cagtcccatg acgctctatg ggccattcc gttcatgcag gctcacaaga aggactctac    1080
tgtgggtgtc ttctggctga acgctgcgga gacctgggtc gacatcgtca agtcgaaatc    1140
ctcgcccgac cctctttctc ttggagtagg ttcgaagaca gacacccaaa ctcattggtt    1200
ttccgagtcg ggacgtattg atttgtttgt cttcttgggc cccactccgc aagagatcag    1260
caaaacatac ggtgaactta ccggctacac tcaattacct caacagttcg ctatcgctta    1320
ccaccagtgt cgttggaact atgtcacgga cgaggatgtc aaggaagttg atcgcaagtt    1380
tgacaagtat cagatcccctt acgatgtgat ttggcttgac attgagtaca cggatgaccg    1440
gaagtacttt acctgggacc ctctgagttt tcctgacccg aagggtatgg aagagcagct    1500
tgatgactcc gagcgcaaac tcgttgtgat cattgacccg cacattaaaa acaaggaagg    1560
atactccatc tctgaagagc tgaagggcaa ggatctggct attaagaaca agggcgggga    1620
gacctacgac ggctggtgtt ggcctggttc atctcactgg gtggactgct caatcccga    1680
agcaatcaaa tggtggaccg gcttgttcaa gtacgacaaa ttcaagggca cccagccaaa    1740
cgtctttatt tggaatgaca tgaatgagcc ctctgtcttc aatggaccgg aaaccactat    1800
gcccaaagac aatatccact atggcaactg ggaacaccgc gacgtgcata atgtcaacgg    1860
```

-continued

```
actgaccttt atcaacgcaa catacaatgc cttactggag cggaagaaag gcgtggttcg    1920 tcggccttc gtcttgaccc gatcattcta cgccggggct caacgggtat ctgctatgtg     1980
gacgggagac aatcaagcca cctgggaaca tctggccgca tccttgccta tggtattgaa    2040
taacggcatt gccgggttcc cgtttgccgg tgccgatgtt ggcgggtttt tccagaaccc    2100
aagcaaggaa cttttgaccc ggtggtatca ggccggcatt tggtatccct tcttccgtgc    2160
ccatgcgcac attgacactc gcagacgaga gccctacttg atcgctgagc cattcaggtc    2220
gatcatatcc caggctatcc gtctgagata tcaactgctg cctgcatggt acactgcttt    2280
tcatgaagct tcggtgaatg gaatgcctat tgttcggccc cagtattatg tccacccggc    2340
ggacgaacaa ggctttgcca ttgatgacca actctacctt ggatctactg gcctgctggc    2400
caaacctgtg gttgtggagg gtgccaccac tacagatatc tacatcgctg acgatgagaa    2460
gtactacgat tactatgatt ttactgtcta ccaaggagcg ggcaggagac atacggtgcc    2520
ttcccccatt gagaaggtcc cattgttgat gcaaggaggt catattatcc ctcgcaagga    2580
ccgcgcacgt cgtagcagcg ggctgatgag atgggatcct tatacacttg tgatcgtcct    2640
cgacaagaac gggaaggccg aaggcacact ctatgttgat gatggggagt cgttcaacta    2700
ccagcagggt gcatacatac accgtcgctt caaatttgaa aaatctaccc ttttgtcgga    2760
agacatcggc accaagggtt cgaagacagc cgaatacctg aagagcatga cgaatgtgcg    2820
ggttcaaaag gtggttgttg tcgacgctcc caaggagtgg cagggaagga cgtctgtgac    2880
cgtcatcgaa gacggtgcaa agatggcttc taccgcaccc ttggagtatc acgcccagca    2940
ggcaggcaag gctgcgtatg ctgtcgtgaa gaaacccgat gttggcattg gaaagacatg    3000
gaagattgaa ttctaa                                                    3016
```

<210> SEQ ID NO 4
<211> LENGTH: 967
<212> TYPE: PRT
<213> ORGANISM: Aspergillus fumigatus

<400> SEQUENCE: 4

```
Met Ala Arg Ser Ser Ser Leu Ser Arg Trp Thr Leu Leu Leu Ala
1               5                   10                  15

Leu Val Val Ile Leu Gly Cys Leu Val Val Pro Gly Val Thr Val Lys
                20                  25                  30

His Glu Asn Phe Lys Lys Cys Ser Gln Ser Gly Phe Cys Lys Arg Asn
            35                  40                  45

Arg Ala Phe Ala Asp Asp Val Ser Ala Gln Gly Ala Ser Trp Ile Ser
        50                  55                  60

Pro Tyr Glu Leu Asp Pro Ser Ser Ile His Phe Lys Asp Gly Gln Leu
65                  70                  75                  80

Gln Gly Thr Ile Leu Lys Ser Ile Ser Ala Asn Glu Lys Val Lys Leu
                85                  90                  95

Pro Leu Val Ile Ser Phe Leu Glu Ser Gly Ala Ala Arg Ile Val Val
            100                 105                 110

Asp Glu Glu Lys Arg Met Lys Gly Glu Ile Asp Leu Arg His Asn Ser
        115                 120                 125

Gln Val Arg Lys Glu Arg Tyr Asn Glu Ala Glu Gln Trp Ala Leu Val
    130                 135                 140

Gly Gly Leu Glu Ser Ser Lys Thr Ala Ala Val Asp Thr Glu Ser Glu
145                 150                 155                 160
```

```
Thr Gly Phe Thr Lys Val Leu Tyr Gly Pro Asp Asn Lys Phe Gln Ala
            165                 170                 175

Ile Ile Arg His Ala Pro Phe Ser Val Asp Phe Gln Arg Asp Gly Gln
        180                 185                 190

Ser His Val Arg Val Asn His Lys Gly Phe Leu Asn Val Glu His Trp
        195                 200                 205

Arg Pro Lys Val Asp Val Ala Glu Gly Asp Ser Val Gln Glu Lys Ser
        210                 215                 220

Ile Pro Gln Gln Asp Glu Ser Thr Trp Trp Glu Thr Phe Gly Gly
225                 230                 235                 240

Asn Thr Asp Ser Lys Pro Lys Gly Pro Glu Ser Ile Gly Leu Asp Ile
            245                 250                 255

Thr Phe Pro Gly Tyr Ser His Val Phe Gly Ile Pro Glu His Ala Asp
            260                 265                 270

Ser Met Ser Leu Lys Glu Thr Arg Gly Gly Asp Gly Asn His Ala Glu
        275                 280                 285

Pro Tyr Arg Met Tyr Asn Thr Asp Val Phe Glu Tyr Glu Leu Asn Ser
        290                 295                 300

Pro Met Thr Leu Tyr Gly Ala Ile Pro Phe Met Gln Ala His Lys Lys
305                 310                 315                 320

Asp Ser Thr Val Gly Val Phe Trp Leu Asn Ala Ala Glu Thr Trp Val
            325                 330                 335

Asp Ile Val Lys Ser Lys Ser Ser Pro Asp Pro Leu Ser Leu Gly Val
            340                 345                 350

Gly Ser Lys Thr Asp Thr Gln Thr His Trp Phe Ser Glu Ser Gly Arg
        355                 360                 365

Ile Asp Leu Phe Val Phe Leu Gly Pro Thr Pro Gln Glu Ile Ser Lys
        370                 375                 380

Thr Tyr Gly Glu Leu Thr Gly Tyr Thr Gln Leu Pro Gln Gln Phe Ala
385                 390                 395                 400

Ile Ala Tyr His Gln Cys Arg Trp Asn Tyr Val Thr Asp Glu Asp Val
            405                 410                 415

Lys Glu Val Asp Arg Lys Phe Asp Lys Tyr Gln Ile Pro Tyr Asp Val
            420                 425                 430

Ile Trp Leu Asp Ile Glu Tyr Thr Asp Asp Arg Lys Tyr Phe Thr Trp
        435                 440                 445

Asp Pro Leu Ser Phe Pro Asp Pro Lys Gly Met Glu Glu Gln Leu Asp
        450                 455                 460

Asp Ser Glu Arg Lys Leu Val Val Ile Asp Pro His Ile Lys Asn
465                 470                 475                 480

Lys Glu Gly Tyr Ser Ile Ser Glu Glu Leu Lys Gly Lys Asp Leu Ala
            485                 490                 495

Ile Lys Asn Lys Gly Gly Glu Thr Tyr Asp Gly Trp Cys Trp Pro Gly
            500                 505                 510

Ser Ser His Trp Val Asp Cys Phe Asn Pro Glu Ala Ile Lys Trp Trp
        515                 520                 525

Thr Gly Leu Phe Lys Tyr Asp Lys Phe Lys Gly Thr Gln Pro Asn Val
        530                 535                 540

Phe Ile Trp Asn Asp Met Asn Glu Pro Ser Val Phe Asn Gly Pro Glu
545                 550                 555                 560

Thr Thr Met Pro Lys Asp Asn Ile His Tyr Gly Asn Trp Glu His Arg
            565                 570                 575
```

Asp Val His Asn Val Asn Gly Leu Thr Phe Ile Asn Ala Thr Tyr Asn
            580                 585                 590
Ala Leu Leu Glu Arg Lys Lys Gly Val Val Arg Arg Pro Phe Val Leu
        595                 600                 605
Thr Arg Ser Phe Tyr Ala Gly Ala Gln Arg Val Ser Ala Met Trp Thr
    610                 615                 620
Gly Asp Asn Gln Ala Thr Trp Glu His Leu Ala Ala Ser Leu Pro Met
625                 630                 635                 640
Val Leu Asn Asn Gly Ile Ala Gly Phe Pro Phe Ala Gly Ala Asp Val
                645                 650                 655
Gly Gly Phe Phe Gln Asn Pro Ser Lys Glu Leu Leu Thr Arg Trp Tyr
            660                 665                 670
Gln Ala Gly Ile Trp Tyr Pro Phe Phe Arg Ala His Ala His Ile Asp
        675                 680                 685
Thr Arg Arg Arg Glu Pro Tyr Leu Ile Ala Glu Pro Phe Arg Ser Ile
    690                 695                 700
Ile Ser Gln Ala Ile Arg Leu Arg Tyr Gln Leu Leu Pro Ala Trp Tyr
705                 710                 715                 720
Thr Ala Phe His Glu Ala Ser Val Asn Gly Met Pro Ile Val Arg Pro
                725                 730                 735
Gln Tyr Tyr Val His Pro Ala Asp Glu Gln Gly Phe Ala Ile Asp Asp
            740                 745                 750
Gln Leu Tyr Leu Gly Ser Thr Gly Leu Leu Ala Lys Pro Val Val Val
        755                 760                 765
Glu Gly Ala Thr Thr Asp Ile Tyr Ile Ala Asp Asp Glu Lys Tyr
    770                 775                 780
Tyr Asp Tyr Tyr Asp Phe Thr Val Tyr Gln Gly Ala Gly Arg Arg His
785                 790                 795                 800
Thr Val Pro Ser Pro Ile Glu Lys Val Pro Leu Leu Met Gln Gly Gly
                805                 810                 815
His Ile Ile Pro Arg Lys Asp Arg Ala Arg Arg Ser Ser Gly Leu Met
            820                 825                 830
Arg Trp Asp Pro Tyr Thr Leu Val Ile Val Leu Asp Lys Asn Gly Lys
        835                 840                 845
Ala Glu Gly Thr Leu Tyr Val Asp Asp Gly Glu Ser Phe Asn Tyr Gln
    850                 855                 860
Gln Gly Ala Tyr Ile His Arg Arg Phe Lys Phe Glu Lys Ser Thr Leu
865                 870                 875                 880
Leu Ser Glu Asp Ile Gly Thr Lys Gly Ser Lys Thr Ala Glu Tyr Leu
                885                 890                 895
Lys Ser Met Thr Asn Val Arg Val Gln Lys Val Val Val Asp Ala
            900                 905                 910
Pro Lys Glu Trp Gln Gly Arg Thr Ser Val Thr Val Ile Glu Asp Gly
        915                 920                 925
Ala Lys Met Ala Ser Thr Ala Pro Leu Glu Tyr His Ala Gln Gln Ala
    930                 935                 940
Gly Lys Ala Ala Tyr Ala Val Val Lys Lys Pro Asp Val Gly Ile Gly
945                 950                 955                 960
Lys Thr Trp Lys Ile Glu Phe
                965

<210> SEQ ID NO 5
<211> LENGTH: 3167

<212> TYPE: DNA
<213> ORGANISM: Aspergillus fumigatus

<400> SEQUENCE: 5

| | | | | | |
|---|---|---|---|---|---|
| atggccagcg | tcctgggcct | cgtcgccagt | gcctggctcc | tccccacggc | ctatggcgca | 60 |
| agccattcgc | ttgcgcctag | cacgtccgca | acctcagcac | aggcgcaata | cactttacca | 120 |
| tcttctattg | acgttggcgc | tcacttgatc | gccaacatcg | acgatcccct | gccgtcgac | 180 |
| gcgcagtctg | tgtgtccggg | ctacacagcc | tcagatgtgc | accagacatc | ccatggtttc | 240 |
| accgctaacc | tacagctcgc | gggtgaccca | tgcaacgtgt | acgggacaga | cgttgattcg | 300 |
| ctgtctctga | cagtggatta | tttggccaag | gaccgcctga | atatccaagt | tgttcctacc | 360 |
| cacgtggatg | cctccaacgc | ttcttggtac | ctcctctcgg | aagatttggt | gccccgggct | 420 |
| catgccctg | cgtgtccgc | ctctcaaagc | gactttgaag | tgaagtggtc | caacgagcct | 480 |
| tctttcaacc | tcaaggtcat | cgcaaggct | actggagacg | tcctcttcga | taccgagggc | 540 |
| tctgtcttgg | tctttgagaa | ccagtttatc | gagtttgtct | cttcgttgcc | tgagggttac | 600 |
| aacctgtacg | ggctgggaga | gcgcatggcc | cagctgcggc | tcttgagaaa | cgcgacccctg | 660 |
| accacctatg | cagcggatgt | gggagacccg | attgataggt | atgttgctgg | ccatggttga | 720 |
| aatctaatgt | acgaagtcga | caagcttaca | atcggctctc | cacagcaaca | tctatggaca | 780 |
| gcatccgttc | tacctcgaca | ctcgatacta | caccaaaggc | gcgaatgggt | cctactcgct | 840 |
| tgtcaacgcc | gacgaggcgg | acttgtcgga | ggatcatgaa | tcattctccc | acggtgtctt | 900 |
| tctgagaaac | gctcatggtc | aggaagttct | cctgcagccc | cgcaacatta | cctggcgcac | 960 |
| aattggtggt | agcatcgatc | tgactttcta | ctccggtccc | acgcaagcgg | acgtcacaaa | 1020 |
| gagctaccag | ctctccacta | ttggacttcc | tgcaatgcag | cagtacagcg | cccttggata | 1080 |
| ccaccaatgc | cgctggggct | accagaattg | gtctcagctc | gaggaagtag | tcaacaactt | 1140 |
| tgagcgattt | gagattcctc | tggaatacat | ctggtcagtc | gggtttctga | gtttctacat | 1200 |
| attgtcctag | tttcttttat | ttaccttcct | tccaggagcg | acatcgatta | catgcttggc | 1260 |
| taccgggact | ttgagaatga | tcccgaacgg | ttctcctacg | atgaaggcga | ggaatttctg | 1320 |
| aacaaactgc | acaagtcggg | acgacactgg | gttcctatcg | ttgactcggc | aatctatatt | 1380 |
| cccaaccccg | acaatgcatt | ggatgcgtaa | gtccttatta | tcttatcctc | cttgtgagat | 1440 |
| ggtcaagttc | aagttctcac | gaaagtgtga | actccaggta | cgagcctat | gctcgcgggg | 1500 |
| caaaggatga | cgttttatc | aagaaccctg | atggcaccct | ctacatcggt | gcagtgtggc | 1560 |
| cgggctttac | tgtcttcccc | gattggcaca | accccaaggc | atttgactac | tgggccaacg | 1620 |
| aactcgtcat | ctggtcaaag | aaggttgcgt | tcgatggcat | ctggattgat | atgagcgaag | 1680 |
| tatcctcttt | ctgcgtgggc | agctgtgaa | caggaaagct | acatctgaat | ccggttcacc | 1740 |
| caccattcca | gcttcccggt | gaacctggca | atgtcggcta | cgactacccc | gaggccttca | 1800 |
| acgtgacgaa | ctctaccgaa | gcggcctctg | cctccgccgc | ctctgccagt | caggcttcgg | 1860 |
| ctgcttctgc | tacccaagcc | gccacgacgt | caacatctac | atcgtatctg | cggacgacgc | 1920 |
| ccacgccggg | cgtccgcgac | gtcaactacc | ctccatatgt | gattaatcat | gttcaggagg | 1980 |
| gccatgacct | tgccgtgcac | gccatttctc | ccaactccac | ccatgtggac | ggcgtccagg | 2040 |
| aatacgatgt | tcacagtctg | tggggccacc | agatcctcaa | tgctacctac | tacggactgc | 2100 |
| gccaggtctt | cactgagaag | cgacctttca | tcattggccg | gtctacctt | gctggctcgg | 2160 |
| gcaagtgggc | cggtcactgg | ggcggtgata | acaactccaa | atgggggtcc | atgttcctgt | 2220 |

```
ccatctcgca gggtctgtcg ttctcgctat tcggtattcc catgttcggc gtggatacat    2280
gcggttttca cggcaacact gacgaggagc tttgcagccg gtggatgcag ctgtcggcct    2340
tcttcccctt ctaccgcaac cacaatgtcc ttgcggctat ccccaggaa ccctaccgct    2400 gggcctctgt cgcccaagcc tccaaggccg ctatgaagat ccgctattcc ctcctacctt    2460
acttctacac tcttttccac caggcccaca ccaccggctc taccgtcatg cgcgctctcg    2520
cctgggagtt ccccacggac ccgtccctcg ccgccgtcga cactcagttc atggtcggcc    2580
cttccatcat ggtcgtcccc gtgcttgagc ccctcgccga taccgtcaag ggcgtgttcc    2640
caggcgtcgg caaaggcgaa gtctggtacg actggtacac ccagaccgcc gtggacgcca    2700
aacccggcgt caacgccacc attcccgcac cgctgggcca cattcccgtc tatgtccgtg    2760
gaggcagcat cctgcccatg caggagcccg ccctcacgac cagagacgcc cgtaacactc    2820
cctggtctct actcgtcgct ctgagtggca accagactgc cttgggctcg ctgtatcttg    2880
acgacggaag cagcctcaac ccgtcccgca ctctcgatgt cgacttccag gctacagcct    2940
cgagcatcaa ggtctcggtc aagggtacct gggaggagaa gaaccgcctg gataaggtga    3000
ctgtcctcgg cgtgactgag aagccttctg ctgtgacgtt caacggccgc aacgtccacc    3060
ctggctcagt gcactacaat actaccacca aggtgctgtc tgtgcaggga ttgcacagca    3120
tgactcccca tggcgcctgg gctggacact ggattctgaa atggtag                  3167
```

<210> SEQ ID NO 6
<211> LENGTH: 988
<212> TYPE: PRT
<213> ORGANISM: Aspergillus fumigatus

<400> SEQUENCE: 6

Met Ala Ser Val Leu Gly Leu Val Ala Ser Ala Trp Leu Leu Pro Thr
 1               5                  10                  15

Ala Tyr Gly Ala Ser His Ser Leu Ala Pro Ser Thr Ser Ala Thr Ser
            20                  25                  30

Ala Gln Ala Gln Tyr Thr Leu Pro Ser Ser Ile Asp Val Gly Ala His
        35                  40                  45

Leu Ile Ala Asn Ile Asp Asp Pro Leu Ala Val Asp Ala Gln Ser Val
    50                  55                  60

Cys Pro Gly Tyr Thr Ala Ser Asp Val His Gln Thr Ser His Gly Phe
65                  70                  75                  80

Thr Ala Asn Leu Gln Leu Ala Gly Asp Pro Cys Asn Val Tyr Gly Thr
                85                  90                  95

Asp Val Asp Ser Leu Ser Leu Thr Val Asp Tyr Leu Ala Lys Asp Arg
            100                 105                 110

Leu Asn Ile Gln Val Val Pro Thr His Val Asp Ala Ser Asn Ala Ser
        115                 120                 125

Trp Tyr Leu Leu Ser Glu Asp Leu Val Pro Arg Ala His Gly Pro Gly
    130                 135                 140

Val Ser Ala Ser Gln Ser Asp Phe Glu Val Lys Trp Ser Asn Glu Pro
145                 150                 155                 160

Ser Phe Asn Leu Lys Val Ile Arg Lys Ala Thr Gly Asp Val Leu Phe
                165                 170                 175

Asp Thr Glu Gly Ser Val Leu Val Phe Glu Asn Gln Phe Ile Glu Phe
            180                 185                 190

Val Ser Ser Leu Pro Glu Gly Tyr Asn Leu Tyr Gly Leu Gly Glu Arg
        195                 200                 205

```
Met Ala Gln Leu Arg Leu Leu Arg Asn Ala Thr Leu Thr Thr Tyr Ala
    210                 215                 220

Ala Asp Val Gly Asp Pro Ile Asp Arg Asn Ile Tyr Gly Gln His Pro
225                 230                 235                 240

Phe Tyr Leu Asp Thr Arg Tyr Tyr Thr Lys Gly Ala Asn Gly Ser Tyr
                245                 250                 255

Ser Leu Val Asn Ala Asp Glu Ala Asp Leu Ser Glu Asp His Glu Ser
            260                 265                 270

Phe Ser His Gly Val Phe Leu Arg Asn Ala His Gly Gln Glu Val Leu
        275                 280                 285

Leu Gln Pro Arg Asn Ile Thr Trp Arg Thr Ile Gly Gly Ser Ile Asp
    290                 295                 300

Leu Thr Phe Tyr Ser Gly Pro Thr Gln Ala Asp Val Thr Lys Ser Tyr
305                 310                 315                 320

Gln Leu Ser Thr Ile Gly Leu Pro Ala Met Gln Gln Tyr Ser Ala Leu
                325                 330                 335

Gly Tyr His Gln Cys Arg Trp Gly Tyr Gln Asn Trp Ser Gln Leu Glu
            340                 345                 350

Glu Val Val Asn Asn Phe Glu Arg Phe Glu Ile Pro Leu Glu Tyr Ile
        355                 360                 365

Trp Ser Asp Ile Asp Tyr Met Leu Gly Tyr Arg Asp Phe Glu Asn Asp
    370                 375                 380

Pro Glu Arg Phe Ser Tyr Asp Glu Gly Glu Phe Leu Asn Lys Leu
385                 390                 395                 400

His Lys Ser Gly Arg His Trp Val Pro Ile Val Asp Ser Ala Ile Tyr
                405                 410                 415

Ile Pro Asn Pro Asp Asn Ala Leu Asp Ala Tyr Glu Pro Tyr Ala Arg
            420                 425                 430

Gly Ala Lys Asp Asp Val Phe Ile Lys Asn Pro Asp Gly Thr Leu Tyr
        435                 440                 445

Ile Gly Ala Val Trp Pro Gly Phe Thr Val Phe Pro Asp Trp His Asn
    450                 455                 460

Pro Lys Ala Phe Asp Tyr Trp Ala Asn Glu Leu Val Ile Trp Ser Lys
465                 470                 475                 480

Lys Val Ala Phe Asp Gly Ile Trp Ile Asp Met Ser Glu Val Ser Ser
                485                 490                 495

Phe Cys Val Gly Ser Cys Gly Thr Gly Lys Leu His Leu Asn Pro Val
            500                 505                 510

His Pro Pro Phe Gln Leu Pro Gly Glu Pro Gly Asn Val Gly Tyr Asp
        515                 520                 525

Tyr Pro Glu Ala Phe Asn Val Thr Asn Ser Thr Glu Ala Ala Ser Ala
    530                 535                 540

Ser Ala Ala Ser Ala Ser Gln Ala Ser Ala Ala Ser Ala Thr Gln Ala
545                 550                 555                 560

Ala Thr Thr Ser Thr Ser Thr Ser Tyr Leu Arg Thr Pro Thr Pro
                565                 570                 575

Gly Val Arg Asp Val Asn Tyr Pro Pro Tyr Val Ile Asn His Val Gln
            580                 585                 590

Glu Gly His Asp Leu Ala Val His Ala Ile Ser Pro Asn Ser Thr His
        595                 600                 605

Val Asp Gly Val Gln Glu Tyr Asp Val His Ser Leu Trp Gly His Gln
    610                 615                 620
```

```
Ile Leu Asn Ala Thr Tyr Tyr Gly Leu Arg Gln Val Phe Thr Glu Lys
625                 630                 635                 640

Arg Pro Phe Ile Ile Gly Arg Ser Thr Phe Ala Gly Ser Gly Lys Trp
            645                 650                 655

Ala Gly His Trp Gly Gly Asp Asn Asn Ser Lys Trp Gly Ser Met Phe
        660                 665                 670

Leu Ser Ile Ser Gln Gly Leu Ser Phe Ser Leu Phe Gly Ile Pro Met
            675                 680                 685

Phe Gly Val Asp Thr Cys Gly Phe Asn Gly Asn Thr Asp Glu Glu Leu
        690                 695                 700

Cys Ser Arg Trp Met Gln Leu Ser Ala Phe Phe Pro Phe Tyr Arg Asn
705                 710                 715                 720

His Asn Val Leu Ala Ala Ile Pro Gln Glu Pro Tyr Arg Trp Ala Ser
                725                 730                 735

Val Ala Gln Ala Ser Lys Ala Ala Met Lys Ile Arg Tyr Ser Leu Leu
            740                 745                 750

Pro Tyr Phe Tyr Thr Leu Phe His Gln Ala His Thr Thr Gly Ser Thr
            755                 760                 765

Val Met Arg Ala Leu Ala Trp Glu Phe Pro Thr Asp Pro Ser Leu Ala
770                 775                 780

Ala Val Asp Thr Gln Phe Met Val Gly Pro Ser Ile Met Val Val Pro
785                 790                 795                 800

Val Leu Glu Pro Leu Ala Asp Thr Val Lys Gly Val Phe Pro Gly Val
                805                 810                 815

Gly Lys Gly Glu Val Trp Tyr Asp Trp Tyr Thr Gln Thr Ala Val Asp
            820                 825                 830

Ala Lys Pro Gly Val Asn Ala Thr Ile Pro Ala Pro Leu Gly His Ile
            835                 840                 845

Pro Val Tyr Val Arg Gly Gly Ser Ile Leu Pro Met Gln Glu Pro Ala
    850                 855                 860

Leu Thr Thr Arg Asp Ala Arg Asn Thr Pro Trp Ser Leu Leu Val Ala
865                 870                 875                 880

Leu Ser Gly Asn Gln Thr Ala Leu Gly Ser Leu Tyr Leu Asp Asp Gly
                885                 890                 895

Ser Ser Leu Asn Pro Ser Arg Thr Leu Asp Val Asp Phe Gln Ala Thr
            900                 905                 910

Ala Ser Ser Ile Lys Val Ser Val Lys Gly Thr Trp Glu Glu Lys Asn
            915                 920                 925

Arg Leu Asp Lys Val Thr Val Leu Gly Val Thr Glu Lys Pro Ser Ala
            930                 935                 940

Val Thr Phe Asn Gly Arg Asn Val His Pro Gly Ser Val His Tyr Asn
945                 950                 955                 960

Thr Thr Thr Lys Val Leu Ser Val Gln Gly Leu His Ser Met Thr Pro
                965                 970                 975

His Gly Ala Trp Ala Gly His Trp Ile Leu Lys Trp
            980                 985
```

<210> SEQ ID NO 7
<211> LENGTH: 22
<212> TYPE: DNA
<213> ORGANISM: Aspergillus niger

<400> SEQUENCE: 7
gtgccccatg atacgcctcc gg                                              22

<210> SEQ ID NO 8
<211> LENGTH: 26
<212> TYPE: DNA
<213> ORGANISM: Aspergillus niger

<400> SEQUENCE: 8
gagtcgtatt tccaaggctc ctgacc                                    26

<210> SEQ ID NO 9
<211> LENGTH: 24
<212> TYPE: DNA
<213> ORGANISM: Aspergillus niger

<400> SEQUENCE: 9
ggaggccatg aagtggacca acgg                                      24

<210> SEQ ID NO 10
<211> LENGTH: 45
<212> TYPE: DNA
<213> ORGANISM: Aspergillus niger

<400> SEQUENCE: 10
caccgtgaaa gccatgctct ttccttcgtg tagaagacca gacag               45

<210> SEQ ID NO 11
<211> LENGTH: 45
<212> TYPE: DNA
<213> ORGANISM: Aspergillus niger

<400> SEQUENCE: 11
ctggtcttct acacgaagga aagagcatgg ctttcacggt gtctg               45

<210> SEQ ID NO 12
<211> LENGTH: 44
<212> TYPE: DNA
<213> ORGANISM: Aspergillus niger

<400> SEQUENCE: 12
ctatatacac aactggattt accatgggcc cgcggccgca gatc                44

<210> SEQ ID NO 13
<211> LENGTH: 44
<212> TYPE: DNA
<213> ORGANISM: Aspergillus niger

<400> SEQUENCE: 13
gatctgcggc cgcgggccca tggtaaatcc agttgtgtat atag                44

<210> SEQ ID NO 14
<211> LENGTH: 26
<212> TYPE: DNA
<213> ORGANISM: Aspergillus niger

<400> SEQUENCE: 14
gtcgacatgg tgttttgatc attta                                     26

<210> SEQ ID NO 15
<211> LENGTH: 26
<212> TYPE: DNA
<213> ORGANISM: Aspergillus niger

```
<400> SEQUENCE: 15
ccatggccag ttgtgtatat agagga                                          26

<210> SEQ ID NO 16
<211> LENGTH: 29
<212> TYPE: DNA
<213> ORGANISM: Aspergillus fumigatus

<400> SEQUENCE: 16
tacacaactg gccatgttga gatcgctgc                                       29

<210> SEQ ID NO 17
<211> LENGTH: 39
<212> TYPE: DNA
<213> ORGANISM: Aspergillus fumigatus

<400> SEQUENCE: 17
gtcacctcta gttaattaac tagctgaggt caatctcgg                            39

<210> SEQ ID NO 18
<211> LENGTH: 30
<212> TYPE: DNA
<213> ORGANISM: Aspergillus fumigatus

<400> SEQUENCE: 18
gcatggagca gggcatcttc ctgcagactc                                      30

<210> SEQ ID NO 19
<211> LENGTH: 30
<212> TYPE: DNA
<213> ORGANISM: Aspergillus fumigatus

<400> SEQUENCE: 19
gagtctgcag gaagatgccc tgctccatgc                                      30

<210> SEQ ID NO 20
<211> LENGTH: 32
<212> TYPE: DNA
<213> ORGANISM: Aspergillus fumigatus

<400> SEQUENCE: 20
acacaactgg ccatggcccg gagcagctcg tc                                   32

<210> SEQ ID NO 21
<211> LENGTH: 40
<212> TYPE: DNA
<213> ORGANISM: Aspergillus fumigatus

<400> SEQUENCE: 21
agtcacctct agttaattaa ttagaattca atcttccatg                           40

<210> SEQ ID NO 22
<211> LENGTH: 32
<212> TYPE: DNA
<213> ORGANISM: Aspergillus fumigatus

<400> SEQUENCE: 22
cgcgcagctc cagactccag gaaagaaatc ac                                   32

<210> SEQ ID NO 23
<211> LENGTH: 32
<212> TYPE: DNA
```

```
<213> ORGANISM: Aspergillus fumigatus

<400> SEQUENCE: 23
gtacttgaac aagccggtcc accatttgat tg                                     32

<210> SEQ ID NO 24
<211> LENGTH: 32
<212> TYPE: DNA
<213> ORGANISM: Aspergillus fumigatus

<400> SEQUENCE: 24
gcctgcctgc tgggcgtgat actccaaggg tg                                     32

<210> SEQ ID NO 25
<211> LENGTH: 39
<212> TYPE: DNA
<213> ORGANISM: Aspergillus fumigatus

<400> SEQUENCE: 25
tacacaactg gccatggcca gcgtcctggg cctcgtcgc                              39

<210> SEQ ID NO 26
<211> LENGTH: 43
<212> TYPE: DNA
<213> ORGANISM: Aspergillus fumigatus

<400> SEQUENCE: 26
gtcacctcta gttaattaac taccatttca gaatccagtg tcc                         43
```